(12) United States Patent
Templin et al.

(10) Patent No.: US 10,023,863 B2
(45) Date of Patent: Jul. 17, 2018

(54) THERAPEUTICS WITH CONFORMATIONALLY RESTRICTED MONOMERS

(71) Applicant: Marina Biotech, Inc., Bothell, WA (US)

(72) Inventors: Michael V. Templin, Bothell, WA (US); Narendra K. Vaish, Kirkland, WA (US); Kathy L. Fosnaugh, Bellevue, WA (US); Shaguna Seth, Bothell, WA (US); Michael E. Houston, Jr., Sammamish, WA (US)

(73) Assignee: Marina Biotech, Inc., City of Industry, CA (US)

( * ) Notice: Subject to any disclaimer, the term of this patent is extended or adjusted under 35 U.S.C. 154(b) by 0 days.

(21) Appl. No.: 14/623,498

(22) Filed: Feb. 17, 2015

(65) Prior Publication Data

US 2015/0284717 A1    Oct. 8, 2015

Related U.S. Application Data

(63) Continuation of application No. 13/643,180, filed as application No. PCT/US2011/033980 on Apr. 26, 2011, now abandoned.

(60) Provisional application No. 61/467,048, filed on Mar. 24, 2011, provisional application No. 61/328,140, filed on Apr. 26, 2010.

(51) Int. Cl.
| | |
|---|---|
| *C12N 15/113* | (2010.01) |
| *A61K 31/713* | (2006.01) |
| *C12N 15/11* | (2006.01) |

(52) U.S. Cl.
CPC .......... *C12N 15/113* (2013.01); *C12N 15/111* (2013.01); *C12N 15/1135* (2013.01); *C12N 15/1136* (2013.01); *C12N 15/1137* (2013.01); *C12N 15/1138* (2013.01); *C12Y 103/99005* (2013.01); *C12Y 203/0102* (2013.01); *C12Y 207/01153* (2013.01); *C12Y 207/11001* (2013.01); *C12Y 207/11021* (2013.01); *C12Y 207/11024* (2013.01); *C12Y 304/21021* (2013.01); *C12N 2310/11* (2013.01); *C12N 2310/14* (2013.01); *C12N 2310/3231* (2013.01); *C12N 2310/533* (2013.01); *C12N 2320/30* (2013.01); *C12N 2320/51* (2013.01)

(58) Field of Classification Search
None
See application file for complete search history.

(56) References Cited

U.S. PATENT DOCUMENTS

| | | | | |
|---|---|---|---|---|
| 5,929,040 A | * | 7/1999 | Werther | ............ A61K 31/7088 |
| | | | | 514/44 A |
| 2004/0033973 A1 | * | 2/2004 | Manoharan | ............ C07H 19/06 |
| | | | | 514/44 A |

FOREIGN PATENT DOCUMENTS

WO    WO 201001731 A2 *    2/2010    ......... C12N 15/1137

OTHER PUBLICATIONS

Wang et al. Bioorganic & Medicinal Chemistry Letters 1999 vol. 9, pp. 1147-1150.*

* cited by examiner

*Primary Examiner* — Tracy Vivlemore
(74) *Attorney, Agent, or Firm* — Eckman Law Group

(57) ABSTRACT

This invention provides single-stranded and multi-stranded compounds that are useful in various therapeutic modalities to regulate the expression of nucleic acid molecules in a cell. A range of compounds is provided, each containing one or more conformationally restricted nucleomonomers (CRN). In addition, compounds can contain one or more conformationally restricted nucleomonomers and one or more hydroxymethyl substituted nucleomonomers (unlocked nucleomonomers, UNA).

10 Claims, 7 Drawing Sheets

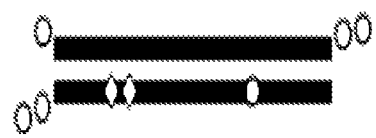

Monomer Q          Monomer R

Monomer E

Monomer F

Monomer G

Monomer H

Monomer I

Monomer J

Monomer K

Monomer L

Monomer M

Monomer N

Monomer O

Monomer P

SEQUENCE LISTING

<160> NUMBER OF SEQ ID NOS: 527

<210> SEQ ID NO 1
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cugccuggca gcccuuucu                                                  19

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cugccuggca gcccuuucuu u                                               21

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ucugccuggc agcccuuucu uu                                              22

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
cugccuggca gcccuuucuu u                                               21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cugccuggca gcccuuucuu u                                               21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cugccuggca gcccuuucuu u                                               21

<210> SEQ ID NO 7
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 7
cugccuggca gcccuuucuu u                                              21

<210> SEQ ID NO 8
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ucugccuggc agcccuuucu uu                                             22

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gaccaccgca ucucuacau                                                 19

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gaccaccgca ucucuacauu u                                              21

<210> SEQ ID NO 11
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ugaccaccgc aucucuacau uu                                             22

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gaccaccgca ucucuacauu u                                              21

<210> SEQ ID NO 13
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 13
gaccaccgca ucucuacauu u                                                    21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gaccaccgca ucucuacauu u                                                    21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gaccaccgca ucucuacauu u                                                    21

<210> SEQ ID NO 16
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ugaccaccgc aucucuacau uu                                                   22

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
cgcaucucua cauucaaga                                                       19

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
cgcaucucua cauucaagau u                                                    21

<210> SEQ ID NO 19
<211> LENGTH: 22
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 19
ucgcaucucu acauucaaga uu                                                    22

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cgcaucucua cauucaagau u                                                     21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
cgcaucucua cauucaagau u                                                     21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cgcaucucua cauucaagau u                                                     21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
cgcaucucua cauucaagau u                                                     21

<210> SEQ ID NO 24
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ucgcaucucu acauucaaga uu                                                    22

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 25
gcccaguguu ucuucugcu                                                19

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gcccaguguu ucuucugcuu u                                             21

<210> SEQ ID NO 27
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ugcccagugu uucuucugcu uu                                            22

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gcccaguguu ucuucugcuu u                                             21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gcccaguguu ucuucugcuu u                                             21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gcccaguguu ucuucugcuu u                                             21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 31
gcccaguguu ucuucugcuu u                                              21

<210> SEQ ID NO 32
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ugcccagugu uucuucugcu uu                                             22

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
cccaguguuu cuucugcuu                                                 19

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
cccaguguuu cuucugcuuu u                                              21

<210> SEQ ID NO 35
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ucccaguguu ucuucugcuu uu                                             22

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
cccaguguuu cuucugcuuu u                                              21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 37
cccaguguuu cuucugcuuu u                                              21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
cccaguguuu cuucugcuuu u                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
cccaguguuu cuucugcuuu u                                              21

<210> SEQ ID NO 40
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ucccaguguu ucuucugcuu uu                                             22

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ccaguguuuc uucugcuuc                                                 19

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ccaguguuuc uucugcuucu u                                              21

<210> SEQ ID NO 43
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
```
uccaguguuu cuucugcuuc uu					22

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ccaguguuuc uucugcuucu u					21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ccaguguuuc uucugcuucu u					21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ccaguguuuc uucugcuucu u					21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
ccaguguuuc uucugcuucu u					21

<210> SEQ ID NO 48
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uccaguguuu cuucugcuuc uu					22

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
caguguuucu ucugcuuca                    19

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
caguguuucu ucugcuucau u                    21

<210> SEQ ID NO 51
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ucaguguuuc uucugcuuca uu                    22

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
caguguuucu ucugcuucau u                    21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
caguguuucu ucugcuucau u                    21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
caguguuucu ucugcuucau u                    21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
caguguuucu ucugcuucau u                    21

```
<210> SEQ ID NO 56
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
ucaguguuuc uucugcuuca uu                                              22

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
aguguuucuu cugcuucaa                                                  19

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
aguguuucuu cugcuucaau u                                               21

<210> SEQ ID NO 59
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uaguguuucu ucugcuucaa uu                                              22

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
aguguuucuu cugcuucaau u                                               21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
aguguuucuu cugcuucaau u                                               21
```

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
aguguuucuu cugcuucaau u                                              21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
aguguuucuu cugcuucaau u                                              21

<210> SEQ ID NO 64
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
uaguguuucu ucugcuucaa uu                                             22

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
gaagaaagaa uuugaggaa                                                 19

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
gaagaaagaa uuugaggaau u                                              21

<210> SEQ ID NO 67
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
ugaagaaaga auuugaggaa uu                                             22

```
<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
gaagaaagaa uuugaggaau u                                              21

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
gaagaaagaa uuugaggaau u                                              21

<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
gaagaaagaa uuugaggaau u                                              21

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gaagaaagaa uuugaggaau u                                              21

<210> SEQ ID NO 72
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
ugaagaaaga auuugaggaa uu                                             22

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
aguggcacca gaggugcuu                                                 19

<210> SEQ ID NO 74
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
aguggcacca gaggugcuuu u                                              21

<210> SEQ ID NO 75
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
uaguggcacc agaggugcuu uu                                             22

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
aguggcacca gaggugcuuu u                                              21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
aguggcacca gaggugcuuu u                                              21

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
aguggcacca gaggugcuuu u                                              21

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
aguggcacca gaggugcuuu u                                              21

<210> SEQ ID NO 80
<211> LENGTH: 22
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
uaguggcacc agaggugcuu uu                                              22

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
agaaagggcu gccaggcag                                                  19

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
agaaagggcu gccaggcagu u                                               21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
agaaagggcu gccaggcagu u                                               21

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
agaaagggcu gccaggcagu u                                               21

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
agaaagggcu gccaggcagu u                                               21

<210> SEQ ID NO 86
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 86
agaaagggcu gccaggcagu u                                            21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
agaaagggcu gccaggcagu u                                            21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
agaaagggcu gccaggcagu u                                            21

<210> SEQ ID NO 89
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
auguagagau gcggugguc                                               19

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
auguagagau gcgguggucu u                                            21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
auguagagau gcgguggucu u                                            21

<210> SEQ ID NO 92
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 92
auguagagau gcgguggucu u                                              21

<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
auguagagau gcgguggucu u                                              21

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
auguagagau gcgguggucu u                                              21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
auguagagau gcgguggucu u                                              21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
auguagagau gcgguggucu u                                              21

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
ucuugaaugu agagaugcg                                                 19

<210> SEQ ID NO 98
<211> LENGTH: 21
<212> TYPE: RNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 98
ucuugaaugu agagaugcgu u                                              21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
ucuugaaugu agagaugcgu u                                              21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ucuugaaugu agagaugcgu u                                              21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
ucuugaaugu agagaugcgu u                                              21

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
ucuugaaugu agagaugcgu u                                              21

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
ucuugaaugu agagaugcgu u                                              21

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
        oligonucleotide

<400> SEQUENCE: 104
ucuugaaugu agagaugcgu u                                              21

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
agcagaagaa acacugggc                                                 19

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
agcagaagaa acacugggcu u                                              21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
agcagaagaa acacugggcu u                                              21

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
agcagaagaa acacugggcu u                                              21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
agcagaagaa acacugggcu u                                              21

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 110
agcagaagaa acacugggcu u                                              21

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
agcagaagaa acacugggcu u                                              21

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
agcagaagaa acacugggcu u                                              21

<210> SEQ ID NO 113
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
aagcagaaga aacacuggg                                                 19

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
aagcagaaga aacacugggu u                                              21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
aagcagaaga aacacugggu u                                              21

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 116
aagcagaaga aacacugggu u                                              21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
aagcagaaga aacacugggu u                                              21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
aagcagaaga aacacugggu u                                              21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
aagcagaaga aacacugggu u                                              21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
aagcagaaga aacacugggu u                                              21

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
gaagcagaag aaacacugg                                                 19

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
```
gaagcagaag aaacacuggu u                                              21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
gaagcagaag aaacacuggu u                                              21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gaagcagaag aaacacuggu u                                              21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
gaagcagaag aaacacuggu u                                              21

<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
gaagcagaag aaacacuggu u                                              21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gaagcagaag aaacacuggu u                                              21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128

```
gaagcagaag aaacacuggu u                                             21

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
ugaagcagaa gaaacacug                                                19

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
ugaagcagaa gaaacacugu u                                             21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
ugaagcagaa gaaacacugu u                                             21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
ugaagcagaa gaaacacugu u                                             21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
ugaagcagaa gaaacacugu u                                             21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
ugaagcagaa gaaacacugu u                                             21
```

```
<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
ugaagcagaa gaaacacugu u                                                     21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
ugaagcagaa gaaacacugu u                                                     21

<210> SEQ ID NO 137
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
uugaagcaga agaaacacu                                                        19

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
uugaagcaga agaaacacuu u                                                     21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
uugaagcaga agaaacacuu u                                                     21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
uugaagcaga agaaacacuu u                                                     21
```

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
uugaagcaga agaaacacuu u                                          21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
uugaagcaga agaaacacuu u                                          21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
uugaagcaga agaaacacuu u                                          21

<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
uugaagcaga agaaacacuu u                                          21

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
uuccucaaau ucuuucuuc                                             19

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
uuccucaaau ucuuucuucu u                                          21

```
<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
uuccucaaau ucuuucuucu u                                              21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
uuccucaaau ucuuucuucu u                                              21

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
uuccucaaau ucuuucuucu u                                              21

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
uuccucaaau ucuuucuucu u                                              21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
uuccucaaau ucuuucuucu u                                              21

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
uuccucaaau ucuuucuucu u                                              21

<210> SEQ ID NO 153
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
aagcaccucu ggugccacu                                                    19

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
aagcaccucu ggugccacuu u                                                 21

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
aagcaccucu ggugccacuu u                                                 21

<210> SEQ ID NO 156
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
aagcaccucu ggugccacuu u                                                 21

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
aagcaccucu ggugccacuu u                                                 21

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
aagcaccucu ggugccacuu u                                                 21

<210> SEQ ID NO 159
<211> LENGTH: 21
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
aagcaccucu ggugccacuu u                                              21

<210> SEQ ID NO 160
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
aagcaccucu ggugccacuu u                                              21

<210> SEQ ID NO 161
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
gagguccuag uggacccacg cagcc                                          25

<210> SEQ ID NO 162
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
agguccuagu ggacccacgc agccg                                          25

<210> SEQ ID NO 163
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
ccuaguggac ccacgcagcc ggcgg                                          25

<210> SEQ ID NO 164
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
guggacccac gcagccggcg gcgcu                                          25

<210> SEQ ID NO 165
<211> LENGTH: 25
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 165
cuccuggagc ugcacaagag gagga                                              25

<210> SEQ ID NO 166
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
ccuggagcug cacaagagga ggaaa                                              25

<210> SEQ ID NO 167
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
ggcugccagu accugcaccg aaacc                                              25

<210> SEQ ID NO 168
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
gaccucaagc ugggcaaccu uuucc                                              25

<210> SEQ ID NO 169
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
gccuaaaaga gaccuaccuc cggau                                              25

<210> SEQ ID NO 170
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
accuaccucc ggaucaagaa gaaug                                              25

<210> SEQ ID NO 171
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 171
auacaguauu cccaagcaca ucaac                                                25

<210> SEQ ID NO 172
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
gccucccuca uccagaagau gcuuc                                                25

<210> SEQ ID NO 173
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
agaagaugcu ucagacagau cccac                                                25

<210> SEQ ID NO 174
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
ucuucugggu cagcaagugg gugga                                                25

<210> SEQ ID NO 175
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
cagccugcag uacauagagc gugac                                                25

<210> SEQ ID NO 176
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
cugcaguaca uagagcguga cggca                                                25

<210> SEQ ID NO 177
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 177
ccuugaugaa gaagaucacc cuccu                                              25

<210> SEQ ID NO 178
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
uauuuccgca auuacaugag cgagc                                              25

<210> SEQ ID NO 179
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
gcccggcugc ccuaccuacg gaccu                                              25

<210> SEQ ID NO 180
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
gccaucaucc ugcaccucag caacg                                              25

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence Combined
      DNA/RNA Molecule: Synthetic oligonucleotide

<400> SEQUENCE: 181
ccuugaugaa gaagaucact t                                                  21

<210> SEQ ID NO 182
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
uuacaguauu cccaagcaca uu                                                 22

<210> SEQ ID NO 183
<211> LENGTH: 22
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 183
uacaguauuc ccaagcacau uu                                            22

<210> SEQ ID NO 184
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
uaccucaagc ugggcaaccu uu                                            22

<210> SEQ ID NO 185
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
uccucaagcu gggcaaccuu uu                                            22

<210> SEQ ID NO 186
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
uaauacagua uucccaagca uu                                            22

<210> SEQ ID NO 187
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
uagaagaugc uucagacaga uu                                            22

<210> SEQ ID NO 188
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
uuccuugaug aagaagauca uu                                            22

<210> SEQ ID NO 189
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 189
uccuugauga agaagaucac uu                                              22

<210> SEQ ID NO 190
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
uauuuccgca auuacaugag uu                                              22

<210> SEQ ID NO 191
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
ggcugcgugg guccacuagg accuccg                                         27

<210> SEQ ID NO 192
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
cggcugcgug gguccacuag gaccucc                                         27

<210> SEQ ID NO 193
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
ccgccggcug cgugggucca cuaggac                                         27

<210> SEQ ID NO 194
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
agcgccgccg gcugcguggg uccacua                                         27

<210> SEQ ID NO 195
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 195
uccuccucuu gugcagcucc aggagag                                        27

<210> SEQ ID NO 196
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
uuuccuccuc uugugcagcu ccaggag                                        27

<210> SEQ ID NO 197
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
gguuucggug cagguacugg cagccaa                                        27

<210> SEQ ID NO 198
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
ggaaaagguu gcccagcuug aggucuc                                        27

<210> SEQ ID NO 199
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
auccggaggu aggucucuuu uaggcaa                                        27

<210> SEQ ID NO 200
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
cauucuucuu gauccggagg uaggucu                                        27

<210> SEQ ID NO 201
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
```
guugaugugc uugggaauac uguauuc 27

<210> SEQ ID NO 202
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
gaagcaucuu cuggaugagg gaggcgg 27

<210> SEQ ID NO 203
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
gugggaucug ucugaagcau cuucugg 27

<210> SEQ ID NO 204
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
uccacccacu ugcugaccca gaagaug 27

<210> SEQ ID NO 205
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
gucacgcucu auguacugca ggcuguc 27

<210> SEQ ID NO 206
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
ugccgucacg cucuauguac ugcaggc 27

<210> SEQ ID NO 207
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
aggaggguga ucuucuucau caaggag        27

<210> SEQ ID NO 208
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
gcucgcucau guaauugcgg aaauauu        27

<210> SEQ ID NO 209
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
agguccguag guagggcagc cgggcga        27

<210> SEQ ID NO 210
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
cguugcugag gugcaggaug auggcgc        27

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence Combined
      DNA/RNA Molecule: Synthetic oligonucleotide

<400> SEQUENCE: 211
gugaucuucu ucaucaaggt t        21

<210> SEQ ID NO 212
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
ugugcuuggg aauacuguau u        21

<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
augugcuugg gaauacuguu u        21

<210> SEQ ID NO 214
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
agguugccca gcuugagguu u                                             21

<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
aagguugccc agcuugaggu u                                             21

<210> SEQ ID NO 216
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
ugcuugggaa uacuguauuu u                                             21

<210> SEQ ID NO 217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
ucugucugaa gcaucuucuu u                                             21

<210> SEQ ID NO 218
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
ugaucuucuu caucaaggau u                                             21

<210> SEQ ID NO 219
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
gugaucuucu ucaucaaggu u                                             21

<210> SEQ ID NO 220
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
cucauguaau ugcggaaauu u                                             21

<210> SEQ ID NO 221
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
guauuuugau gaggaguuca cggcc                                         25

<210> SEQ ID NO 222
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
ggcccagaug aucaccauca cacca                                         25

<210> SEQ ID NO 223
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
gggaagaaaa cuauccugcg gguuu                                         25

<210> SEQ ID NO 224
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
guuuuaauuu auuucaucca guuug                                         25

<210> SEQ ID NO 225
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
acguagggaa auguuaagga cuucu                                         25

```
<210> SEQ ID NO 226
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
ggccgugaac uccucaucaa aauaccu                                              27

<210> SEQ ID NO 227
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
uggugugaug gugaucaucu gggccgu                                              27

<210> SEQ ID NO 228
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
aaacccgcag gauaguuuuc uucccua                                              27

<210> SEQ ID NO 229
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
caaacuggau gaaauaaauu aaaaccc                                              27

<210> SEQ ID NO 230
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
agaaguccuu aacauuuccc uacguga                                              27

<210> SEQ ID NO 231
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
guauuuugau gagg                                                            14

<210> SEQ ID NO 232
```

-continued

```
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
ggcccagaug au                                                              12

<210> SEQ ID NO 233
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
gggaagaaaa cuau                                                            14

<210> SEQ ID NO 234
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
guuuuaauuu auuuc                                                           15

<210> SEQ ID NO 235
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
acguagggaa au                                                              12

<210> SEQ ID NO 236
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
aguucacggc c                                                               11

<210> SEQ ID NO 237
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
caccaucaca cca                                                             13

<210> SEQ ID NO 238
<211> LENGTH: 11
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
ccugcggguu u                                                               11

<210> SEQ ID NO 239
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
auccaguuug                                                                 10

<210> SEQ ID NO 240
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
guuaaggacu ucu                                                             13

<210> SEQ ID NO 241
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
guucacggcc                                                                 10

<210> SEQ ID NO 242
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
accaucacac ca                                                              12

<210> SEQ ID NO 243
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
cugcggguuu                                                                 10

<210> SEQ ID NO 244
<211> LENGTH: 9
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 244 uccaguuug                                                                 9

<210> SEQ ID NO 245
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
uuaaggacuu cu                                                            12

<210> SEQ ID NO 246
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
gcugcuuaug ucucccagca uggcc                                              25

<210> SEQ ID NO 247
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
aaguguuuca gaagcuucuc ccuga                                              25

<210> SEQ ID NO 248
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
gaccaucaau aaggaagaag cccuu                                              25

<210> SEQ ID NO 249
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
ccaucaauaa ggaagaagcc cuuca                                              25

<210> SEQ ID NO 250
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 250
ucaauaagga agaagcccuu cagcg                                           25

<210> SEQ ID NO 251
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
ggccaugcug ggagacauaa gcagcag                                         27

<210> SEQ ID NO 252
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
ucagggagaa gcuucugaaa cacuucu                                         27

<210> SEQ ID NO 253
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
aagggcuucu uccuuauuga uggucag                                         27

<210> SEQ ID NO 254
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
ugaagggcuu cuuccuuauu gaugguc                                         27

<210> SEQ ID NO 255
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
cgcugaaggg cuucuuccuu auugaug                                         27

<210> SEQ ID NO 256
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 256
acuggauuua agcagaguuc aaaag                                              25

<210> SEQ ID NO 257
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
cuggauuuaa gcagaguuca aaagc                                              25

<210> SEQ ID NO 258
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
gauuuaagca gaguucaaaa gcccu                                              25

<210> SEQ ID NO 259
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
auuuaagcag aguucaaaag cccuu                                              25

<210> SEQ ID NO 260
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
uuaagcagag uucaaaagcc cuuca                                              25

<210> SEQ ID NO 261
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
cuuuugaacu cugcuuaaau ccagugg                                            27

<210> SEQ ID NO 262
<211> LENGTH: 27
<212> TYPE: RNA
<213> ORGANISM: Artificial Sequence
<220> FEATURE:
<223> OTHER INFORMATION: Description of Artificial Sequence: Synthetic
```

```
oligonucleotide

<400> SEQUENCE: 262
gcuuuugaac ucugcuuaaa uccagug                                        27

<210> SEQ ID NO 263
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
agggcuuuug aacucugcuu aaaucca                                        27

<210> SEQ ID NO 264
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
aagggcuuuu gaacucugcu uaaaucc                                        27

<210> SEQ ID NO 265
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
ugaagggcuu uugaacucug cuuaaau                                        27

<210> SEQ ID NO 266
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
uuccagccca cauuggauuc aucag                                          25

<210> SEQ ID NO 267
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
cagcugagaa uguggaauac cuaag                                          25

<210> SEQ ID NO 268
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 268
aacguaucuc cuaauuugag gcuca                                         25

<210> SEQ ID NO 269
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
ccuaaaauaa uuucucuaca auugg                                         25

<210> SEQ ID NO 270
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
uggaagauuc agcuaguuag gagcc                                         25

<210> SEQ ID NO 271
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
cugaugaauc caauggggc uggaauc                                        27

<210> SEQ ID NO 272
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
cuuagguauu ccacauucuc agcugug                                       27

<210> SEQ ID NO 273
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
ugagccucaa auuaggagau acguuuu                                       27

<210> SEQ ID NO 274
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 274
ccaauuguag agaaauuauu uuaggaa                                         27

<210> SEQ ID NO 275
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
ggcuccuaac uagcugaauc uuccaau                                         27

<210> SEQ ID NO 276
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
ugaccuguga agcaacaguc aaugg                                           25

<210> SEQ ID NO 277
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
cuaucucaca caucgacaaa ccaau                                           25

<210> SEQ ID NO 278
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
uguccucaau uguacugcua ccacu                                           25

<210> SEQ ID NO 279
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
aaaccguagc uggcaagcgg ucuua                                           25

<210> SEQ ID NO 280
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
```
uagcuggcaa gcggucuuac cggcu                                    25

<210> SEQ ID NO 281
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
ccauugacug uugcuucaca ggucaga                                  27

<210> SEQ ID NO 282
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
auugguuugu cgauguguga gauaguu                                  27

<210> SEQ ID NO 283
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
agugguagca guacaauuga ggacaag                                  27

<210> SEQ ID NO 284
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
uaagaccgcu ugccagcuac gguuuca                                  27

<210> SEQ ID NO 285
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
agccgguaag accgcuugcc agcuacg                                  27

<210> SEQ ID NO 286
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
acuuuggaug uuccaacgca aguug                                              25

<210> SEQ ID NO 287
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
aaugcuucca cuaaacugaa accau                                              25

<210> SEQ ID NO 288
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
gagaaaguuu gacuuuguua aauau                                              25

<210> SEQ ID NO 289
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
aaagaacuac uguauauuaa aaguu                                              25

<210> SEQ ID NO 290
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
uuagaaauac ggguuuugac uuaac                                              25

<210> SEQ ID NO 291
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
caacuugcgu uggaacaucc aaagugu                                            27

<210> SEQ ID NO 292
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
augguuucag uuuaguggaa gcauuua                                            27

<210> SEQ ID NO 293
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
auauuuaaca aagucaaacu uucucac                                             27

<210> SEQ ID NO 294
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
aacuuuuaau auacaguagu ucuuuuc                                             27

<210> SEQ ID NO 295
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
guuaagucaa aacccguauu ucuaaag                                             27

<210> SEQ ID NO 296
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
cuaguccuuc cgauggaagc acuag                                               25

<210> SEQ ID NO 297
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
ccagugaaua uuguuuuuau gugga                                               25

<210> SEQ ID NO 298
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
augaauucaa guuggaauug guaga                                               25

```
<210> SEQ ID NO 299
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
caggacacag auuuagacuu ggaga                                              25

<210> SEQ ID NO 300
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
cucaaagcac aguuacagua uucca                                              25

<210> SEQ ID NO 301
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
cuagugcuuc caucggaagg acuaggu                                            27

<210> SEQ ID NO 302
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
uccacauaaa aacaauauuc acuggga                                            27

<210> SEQ ID NO 303
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
ucuaccaauu ccaacuugaa uucauug                                            27

<210> SEQ ID NO 304
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
ucuccaaguc uaaaucugug uccugag                                            27
```

```
<210> SEQ ID NO 305
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
uggaauacug uaacugugcu uugagga                                            27

<210> SEQ ID NO 306
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
ugagcuauuu aaggaucuau uuaug                                              25

<210> SEQ ID NO 307
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
aaaaggugaa aaagcacuau uauca                                              25

<210> SEQ ID NO 308
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
gaaaaagcac uauuaucagu ucugc                                              25

<210> SEQ ID NO 309
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
ggcugaaaag aaagauuaaa ccuac                                              25

<210> SEQ ID NO 310
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
uaaacccuua uaauaaaauc cuucu                                              25

<210> SEQ ID NO 311
```

```
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
cauaaauaga uccuuaaaua gcucaaa                                          27

<210> SEQ ID NO 312
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
ugauaauagu gcuuuucac cuuuuuc                                           27

<210> SEQ ID NO 313
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
gcagaacuga uaauagugcu uuucac                                           27

<210> SEQ ID NO 314
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
guagguuuaa ucuuucuuuu cagccau                                          27

<210> SEQ ID NO 315
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
agaaggauuu uauuauaagg guuuaau                                          27

<210> SEQ ID NO 316
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
caggaauaaa gauggcugcu gaacc                                            25

<210> SEQ ID NO 317
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
aauuugaaug accaaguucu cuuca                                              25

<210> SEQ ID NO 318
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
auguauaaag auagccagcc uagag                                              25

<210> SEQ ID NO 319
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
ggcuguaacu aucucuguga agugu                                              25

<210> SEQ ID NO 320
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
ucugugaagu gugagaaaau uucaa                                              25

<210> SEQ ID NO 321
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
gguucagcag ccaucuuuau uccugcg                                            27

<210> SEQ ID NO 322
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
ugaagagaac uuggucauuc aaauuuc                                            27

<210> SEQ ID NO 323
<211> LENGTH: 27
<212> TYPE: RNA
```

<213> ORGANISM: Artificial Sequence
<220> FEATURE:
<223> OTHER INFORMATION: Description of Artificial Sequence: Synthetic
    oligonucleotide

<400> SEQUENCE: 323
cucuaggcug gcuaucuuua uacauac                                           27

<210> SEQ ID NO 324
<211> LENGTH: 27
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 324
acacuucaca gagauaguua cagccau                                           27

<210> SEQ ID NO 325
<211> LENGTH: 27
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 325
uugaaauuuu cucacacuuc acagaga                                           27

<210> SEQ ID NO 326
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 326
acgaaagaga agcucuaucu cgccu                                             25

<210> SEQ ID NO 327
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 327
cuccacaagc gccuucgguc caguu                                             25

<210> SEQ ID NO 328
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 328
gagaagauuc caaagaugua gccgc                                             25

<210> SEQ ID NO 329
<211> LENGTH: 25
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 329
aaucuggauu caaugaggag acuug                                              25

<210> SEQ ID NO 330
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
agaacagauu ugagaguagu gagga                                              25

<210> SEQ ID NO 331
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
aggcgagaua gagcuucucu uucguuc                                            27

<210> SEQ ID NO 332
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
aacuggaccg aaggcgcuug uggagaa                                            27

<210> SEQ ID NO 333
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
gcggcuacau cuuuggaauc uucuccu                                            27

<210> SEQ ID NO 334
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
caagucuccu cauugaaucc agauugg                                            27

<210> SEQ ID NO 335
<211> LENGTH: 27
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 335
uccucacuac ucucaaaucu guucugg                                          27

<210> SEQ ID NO 336
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
caugcugcug gcgucuaagu guuug                                            25

<210> SEQ ID NO 337
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
agaugugcau uucaccugug acaaa                                            25

<210> SEQ ID NO 338
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
ucaaaaccug ugccaggcug aauua                                            25

<210> SEQ ID NO 339
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
gaaugugggu agucauucuu acaau                                            25

<210> SEQ ID NO 340
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340 augugguag ucauucuuac aauug                                             25

<210> SEQ ID NO 341
<211> LENGTH: 27
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 341
caaacacuua gacgccagca gcauggg                                    27

<210> SEQ ID NO 342
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
uuugucacag gugaaaugca caucuga                                    27

<210> SEQ ID NO 343
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
uaauucagcc uggcacaggu uuugauc                                    27

<210> SEQ ID NO 344
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
auuguaagaa ugacuaccca cauucac                                    27

<210> SEQ ID NO 345
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
caauuguaag aaugacuacc cacauuc                                    27

<210> SEQ ID NO 346
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
cauauccuug gcuacuaaca ucugg                                      25

<210> SEQ ID NO 347
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 347
uacuaacauc uggagacugu gagcu                                              25

<210> SEQ ID NO 348
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
cauaaguugu gugcuuuuua uuaau                                              25

<210> SEQ ID NO 349
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
gcaucauuuu ggcucuucuu acauu                                              25

<210> SEQ ID NO 350
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
gcucuucuua cauuguaaa aaugu                                               25

<210> SEQ ID NO 351
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
ccagauguua guagccaagg auauggu                                            27

<210> SEQ ID NO 352
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
agcucacagu cuccagaugu uaguagc                                            27

<210> SEQ ID NO 353
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 353
auuaauaaaa agcacacaac uuauggc                                              27

<210> SEQ ID NO 354
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
aauguaagaa gagccaaaau gaugcau                                              27

<210> SEQ ID NO 355
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
acauuuuuac aaauguaaga agagcca                                              27

<210> SEQ ID NO 356
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
ucggaaacaa guuauucucu ucacu                                                25

<210> SEQ ID NO 357
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
acucccaaua acuaaugcua agaaa                                                25

<210> SEQ ID NO 358
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
aaugcuaaga aaugcugaaa aucaa                                                25

<210> SEQ ID NO 359
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
```

```
gucuuucucu aaauaugauu acuuu                                       25
```

<210> SEQ ID NO 360
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360

```
ugaauuucag gcauuuuguu cuaca                                       25
```

<210> SEQ ID NO 361
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361

```
agugaagaga auaacuuguu uccgaag                                     27
```

<210> SEQ ID NO 362
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362

```
uuucuuagca uuaguuauug ggaguga                                     27
```

<210> SEQ ID NO 363
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363

```
uugauuuuca gcauuucuua gcauuag                                     27
```

<210> SEQ ID NO 364
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364

```
aaaguaauca uauuuagaga aagacag                                     27
```

<210> SEQ ID NO 365
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
uguagaacaa aaugccugaa auucagc                                              27

<210> SEQ ID NO 366
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
aaugugacau caaagcaagu auugu                                                25

<210> SEQ ID NO 367
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
caucaaagca aguauuguag cacuc                                                25

<210> SEQ ID NO 368
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
agagagagaa aacaaaacca caaau                                                25

<210> SEQ ID NO 369
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
ucgcuguagu auuuaagccc auaca                                                25

<210> SEQ ID NO 370
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
cgcuguagua uuuaagccca uacag                                                25

<210> SEQ ID NO 371
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
acaauacuug cuuugauguc acauuaa                                              27

<210> SEQ ID NO 372
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
gagugcuaca auacuugcuu ugauguc                                          27

<210> SEQ ID NO 373
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
auuugugguu uuguuucuc ucucucu                                           27

<210> SEQ ID NO 374
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
uguaugggcu uaaauacuac agcgagg                                          27

<210> SEQ ID NO 375
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
cuguaugggc uuaaauacua cagcgag                                          27

<210> SEQ ID NO 376
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
cuguucugau cggccaguuu ucgga                                            25

<210> SEQ ID NO 377
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
aaauaauuug aacuuuggaa caggg                                            25

<210> SEQ ID NO 378
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
ugcgaccuua auuuaacuuu ccagu                                              25

<210> SEQ ID NO 379
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
cugagaaagc uaaaguuugg uuuug                                              25

<210> SEQ ID NO 380
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
aguaaagaug cuacuuccca cugua                                              25

<210> SEQ ID NO 381
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
uccgaaaacu ggccgaucag aacagcc                                            27

<210> SEQ ID NO 382
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
cccuguucca aaguucaaau uauuugu                                            27

<210> SEQ ID NO 383
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
acuggaaagu uaaauuaagg ucgcaau                                            27

```
<210> SEQ ID NO 384
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
caaaaccaaa cuuuagcuuu cucagcc                                          27

<210> SEQ ID NO 385
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
uacaguggga aguagcaucu uuacuuu                                          27

<210> SEQ ID NO 386
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386 cguucugau cggccaguuu ucgga                                             25

<210> SEQ ID NO 387
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
aaauaauuug aacuuuggaa caggg                                            25

<210> SEQ ID NO 388
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
ugcgaccuua auuuaacuuu ccagu                                            25

<210> SEQ ID NO 389
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
cugagaaagc uaaaguuugg uuuug                                            25

<210> SEQ ID NO 390
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
aguaaagaug cuacuuccca cugua                                            25

<210> SEQ ID NO 391
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
uccgaaaacu ggccgaucag aacagcc                                          27

<210> SEQ ID NO 392
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
cccuguucca aaguucaaau uauuugu                                          27

<210> SEQ ID NO 393
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
acuggaaagu uaaauuaagg ucgcaau                                          27

<210> SEQ ID NO 394
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
caaaaccaaa cuuuagcuuu cucagcc                                          27

<210> SEQ ID NO 395
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
uacaguggga aguagcaucu uuacuuu                                          27

<210> SEQ ID NO 396
<211> LENGTH: 25
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
gaauccuagu agaauguuua cuacc                                              25

<210> SEQ ID NO 397
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
gaaagggaag aauuuuuuga ugaaa                                              25

<210> SEQ ID NO 398
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
uaucggcaug ccagugugug aauuu                                              25

<210> SEQ ID NO 399
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
caccucauag uagagcaaug uaugu                                              25

<210> SEQ ID NO 400
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
ccagaauugc caaagcacau auaua                                              25

<210> SEQ ID NO 401
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
gguaguaaac auucuacuag gauucuu                                            27

<210> SEQ ID NO 402
<211> LENGTH: 27
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 402
uuucaucaaa aaauucuucc cuuucug                                           27

<210> SEQ ID NO 403
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
aaauucacac acuggcaugc cgauagc                                           27

<210> SEQ ID NO 404
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
acauacauug cucuacuaug aggugaa                                           27

<210> SEQ ID NO 405
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
uauauaugug cuuuggcaau ucuggug                                           27

<210> SEQ ID NO 406
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
ugcaguucuu acacgagaag aagau                                             25

<210> SEQ ID NO 407
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
acgagaagaa gaucauuuac aggga                                             25

<210> SEQ ID NO 408
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 408
cgagaagaag aucauuuaca gggac                                        25

<210> SEQ ID NO 409
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
aagaagauca uuuacaggga ccuga                                        25

<210> SEQ ID NO 410
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
agaggaagag guguuugacu gcauc                                        25

<210> SEQ ID NO 411
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
aucuucuucu cguguaagaa cugcagc                                      27

<210> SEQ ID NO 412
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
ucccuguaaa ugaucuucuu cucgugu                                      27

<210> SEQ ID NO 413
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
gucccuguaa augaucuucu ucucgug                                      27

<210> SEQ ID NO 414
<211> LENGTH: 27
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 414
ucaggucccu guaaaugauc uucuucu                                              27

<210> SEQ ID NO 415
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
gaugcaguca aacaccucuu ccucugu                                              27

<210> SEQ ID NO 416
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
ugcaguaaag auccuaaagg uuguc                                                25

<210> SEQ ID NO 417
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
aguaaagauc cuaaagguug ucgac                                                25

<210> SEQ ID NO 418
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
ugacaaagga caaccuggca auugu                                                25

<210> SEQ ID NO 419
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
gcaauuguga cccaguggug cgagg                                                25

<210> SEQ ID NO 420
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 420
aacaucaucc auagagacau gaaau                                              25

<210> SEQ ID NO 421
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
gacaaccuuu aggaucuuua cugcaac                                            27

<210> SEQ ID NO 422
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
gucgacaacc uuuaggaucu uuacugc                                            27

<210> SEQ ID NO 423
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
acaauugcca gguuguccuu ugucaug                                            27

<210> SEQ ID NO 424
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
ccucgcacca cugggucaca auugcca                                            27

<210> SEQ ID NO 425
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
auuucauguc ucuauggaug auguucu                                            27

<210> SEQ ID NO 426
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 426
aauggagguu gaauauccua cugug                                              25

<210> SEQ ID NO 427
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
ggagguugaa uauccuacug uguaa                                              25

<210> SEQ ID NO 428
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
auuuugaguu uucccuugua gugua                                              25

<210> SEQ ID NO 429
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
uauccuguuu guucuuuguu gauug                                              25

<210> SEQ ID NO 430
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
ccuguuuguu cuuuguugau ugaaa                                              25

<210> SEQ ID NO 431
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
cacaguagga uauucaaccu ccauuuc                                            27

<210> SEQ ID NO 432
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 432
uuacacagua ggauauucaa ccuccau                                      27

<210> SEQ ID NO 433
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
uacacuacaa gggaaaacuc aaaaucu                                      27

<210> SEQ ID NO 434
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
caaucaacaa agaacaaaca ggauaaa                                      27

<210> SEQ ID NO 435
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
uuucaaucaa caaagaacaa acaggau                                      27

<210> SEQ ID NO 436
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
aagagggaga gaagcaacua cagac                                        25

<210> SEQ ID NO 437
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
cgucuccuac cagaccaagg ucaac                                        25

<210> SEQ ID NO 438
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
```
gaucaaucgg cccgacuauc ucgac                                            25

<210> SEQ ID NO 439
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
ggacgaacau ccaaccuucc caaac                                            25

<210> SEQ ID NO 440
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
agggucggaa cccaagcuua gaacu                                            25

<210> SEQ ID NO 441
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
gucuguaguu gcuucucucc cucuuag                                          27

<210> SEQ ID NO 442
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
guugaccuug gucugguagg agacggc                                          27

<210> SEQ ID NO 443
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
gucgagauag ucgggccgau ugaucuc                                          27

<210> SEQ ID NO 444
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444

```
guuugggaag guuggauguu cguccuc                                       27
```

<210> SEQ ID NO 445
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445

```
aguucuaagc uuggguuccg acccuaa                                       27
```

<210> SEQ ID NO 446
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446

```
aaacacagau aacaggaaau gaucc                                         25
```

<210> SEQ ID NO 447
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447

```
cuuaagaaaa gagaagaaau gaaac                                         25
```

<210> SEQ ID NO 448
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448

```
cugaaggagu guguuccau ccucc                                          25
```

<210> SEQ ID NO 449
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449

```
ucaccgcggg acugaaaauc uuuga                                         25
```

<210> SEQ ID NO 450
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450

```
agcagaaaua agcgugccgu ucagg                                         25
```

<210> SEQ ID NO 451
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
ggaucauuuc cuguuaucug uguuugu                                           27

<210> SEQ ID NO 452
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
guuucauuuc uucucuuuuc uuaaggc                                           27

<210> SEQ ID NO 453
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
ggaggaugga aacacacucc uucaguu                                           27

<210> SEQ ID NO 454
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
ucaaagauuu ucagucccgc ggugaca                                           27

<210> SEQ ID NO 455
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
ccugaacggc acgcuuauuu cugcugu                                           27

<210> SEQ ID NO 456
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
caaagaaaga uagagcaaga caaga                                             25

```
<210> SEQ ID NO 457
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
aagaaagaua gagcaagaca agaaa                                           25

<210> SEQ ID NO 458
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
gaaagcauuu guuuguacaa gaucc                                           25

<210> SEQ ID NO 459
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
ugaguuaaac gaacguacuu gcaga                                           25

<210> SEQ ID NO 460
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
acugauacag aacgaucgau acaga                                           25

<210> SEQ ID NO 461
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
ucuugucuug cucuaucuuu cuuuggu                                         27

<210> SEQ ID NO 462
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
uuucuugucu ugcucuaucu uucuuug                                         27
```

```
<210> SEQ ID NO 463
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
ggaucuugua caaacaaaug cuuucuc                                              27

<210> SEQ ID NO 464
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
ucugcaagua cguucguuua acucaag                                              27

<210> SEQ ID NO 465
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
ucuguaucga ucguucugua ucagucu                                              27

<210> SEQ ID NO 466
<211> LENGTH: 21
<212> TYPE: DNA
<213> ORGANISM: Artificial Sequence
<220> FEATURE:
<223> OTHER INFORMATION: Description of Artificial Sequence Combined
      DNA/RNA Molecule: Synthetic oligonucleotide

<400> SEQUENCE: 466
caucacacug aauaccaaut t                                                    21

<210> SEQ ID NO 467
<211> LENGTH: 21
<212> TYPE: DNA
<213> ORGANISM: Artificial Sequence
<220> FEATURE:
<223> OTHER INFORMATION: Description of Artificial Sequence Combined
      DNA/RNA Molecule: Synthetic oligonucleotide

<400> SEQUENCE: 467
auugguauuc agugugaugt t                                                    21

<210> SEQ ID NO 468
<211> LENGTH: 21
<212> TYPE: DNA
<213> ORGANISM: Artificial Sequence
<220> FEATURE:
<223> OTHER INFORMATION: Description of Artificial Sequence Combined
      DNA/RNA Molecule: Synthetic oligonucleotide

<400> SEQUENCE: 468
caucacacug aauaccaaut t                                                    21

<210> SEQ ID NO 469
```

```
<211> LENGTH: 21
<212> TYPE: DNA
<213> ORGANISM: Artificial Sequence
<220> FEATURE:
<223> OTHER INFORMATION: Description of Artificial Sequence Combined
      DNA/RNA Molecule: Synthetic oligonucleotide

<400> SEQUENCE: 469
auugguauuc agugugaugt t                                              21

<210> SEQ ID NO 470
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
uuguuguugu uguuguugu                                                 19

<210> SEQ ID NO 471
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
acaacaacaa caacaacaa                                                 19

<210> SEQ ID NO 472
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
uuguuguugu uguuguugu                                                 19

<210> SEQ ID NO 473
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
acaacaacaa caacaacaa                                                 19

<210> SEQ ID NO 474
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: um

<400> SEQUENCE: 474
ccauguggaa aaauaccuau u                                              21
```

<210> SEQ ID NO 475
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: um

<400> SEQUENCE: 475
cuggauuucu uacagugauu u                                           21

<210> SEQ ID NO 476
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
aguggcugca aaagcucauu u                                           21

<210> SEQ ID NO 477
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 477
ggcagguccu guuguugguu u                                           21

<210> SEQ ID NO 478
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 478
ccagggucuc ccaguacauu u                                           21

<210> SEQ ID NO 479
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 479
ucgaguggcu gcaaaagcuu u                                              21

<210> SEQ ID NO 480
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 480
gcggcuguga gcaguacugu u                                              21

<210> SEQ ID NO 481
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 481
aggaugacca gcugaucugu u                                              21

<210> SEQ ID NO 482
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 482
cgaugcugac uccauguguu u                                              21

<210> SEQ ID NO 483
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 483
ggcgguuguu uagcucucau u                                              21

<210> SEQ ID NO 484
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
ugucuugguu ucaauuaaau u    21

<210> SEQ ID NO 485
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 485
uagguauuuu uccacauggu u    21

<210> SEQ ID NO 486
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 486
aucacuguaa gaaauccagu u    21

<210> SEQ ID NO 487
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 487
augagcuuuu gcagccacuu u    21

<210> SEQ ID NO 488
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 488
accaacaaca ggaccugccu u    21

<210> SEQ ID NO 489
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 489
auguacuggg agacccuggu u                                              21

<210> SEQ ID NO 490
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 490
agcuuuugca gccacucgau u                                              21

<210> SEQ ID NO 491
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 491
caguacugcu cacagccgcu u                                              21

<210> SEQ ID NO 492
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 492
cagaucagcu ggucauccuu u                                              21

<210> SEQ ID NO 493
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 493
acacauggag ucagcaucgu u                                              21
```

```
<210> SEQ ID NO 494
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: um

<400> SEQUENCE: 494
ugagagcuaa acaaccgccu u                                              21

<210> SEQ ID NO 495
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
uuuaauugaa accaagacau u                                              21

<210> SEQ ID NO 496
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
ggacauucag aacaagaaau u                                              21

<210> SEQ ID NO 497
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 497
acagaguccc ucaaacagau u                                              21

<210> SEQ ID NO 498
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
caucacacug aauaccaauu u                                              21

<210> SEQ ID NO 499
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
```
aagggaaucu uauauuugau ccaaa                                                  25

<210> SEQ ID NO 500
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
acagaguccc ucaaacagac augac                                                  25

<210> SEQ ID NO 501
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
gucucaaaag guuuacuaau auucg                                                  25

<210> SEQ ID NO 502
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
uuucuuguuc ugaauguccu u                                                      21

<210> SEQ ID NO 503
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 503
ucuguuugag ggacucuguu u                                                      21

<210> SEQ ID NO 504
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
auugguauuc agugugaugu u                                                      21

<210> SEQ ID NO 505
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505

```
uuuggaucaa auauaagauu cccuucu                                              27
```

<210> SEQ ID NO 506
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506

```
gucaugucug uuugagggac ucuguga                                              27
```

<210> SEQ ID NO 507
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507

```
cgaauauuag uaaaccuuuu gagacug                                              27
```

<210> SEQ ID NO 508
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508

```
guccucugau ggucaaaguu u                                                    21
```

<210> SEQ ID NO 509
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509

```
gacugguauu ugugucugau u                                                    21
```

<210> SEQ ID NO 510
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510

```
uggacuggua uuugugucuu u                                                    21
```

<210> SEQ ID NO 511
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511

```
cacucauucu uggcaggauu u                                                    21
```

<210> SEQ ID NO 512
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
ccuugcugga cugguauuuu u                                              21

<210> SEQ ID NO 513
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
acuuugacca ucagaggacu u                                              21

<210> SEQ ID NO 514
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
ucagacacaa auaccagucu u                                              21

<210> SEQ ID NO 515
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
agacacaaau accaguccau u                                              21

<210> SEQ ID NO 516
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
auccugccaa gaaugagugu u                                              21

<210> SEQ ID NO 517
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
aaauaccagu ccagcaaggu u                                              21

<210> SEQ ID NO 518
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
ucucugucac cuggcucaau aggdtc                                              26

<210> SEQ ID NO 519
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
cgagacuacu uucccaucca gcugg                                               25

<210> SEQ ID NO 520
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
gaagacacac aaccugcuga ccacc                                               25

<210> SEQ ID NO 521
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
ugaccaccag gaacuauauc uuugg                                               25

<210> SEQ ID NO 522
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
gaccaccagg aacuauaucu uugga                                               25

<210> SEQ ID NO 523
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
gaccuauuga gccaggugac agagaag                                             27

```
<210> SEQ ID NO 524
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
ccagcuggau gggaaaguag ucucgaa                                              27

<210> SEQ ID NO 525
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
gguggucagc agguugugug ucuucac                                              27

<210> SEQ ID NO 526
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
ccaaagauau aguuccuggu ggucagc                                              27

<210> SEQ ID NO 527
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
uccaaagaua uaguuccugg uggucag                                              27
```

THERAPEUTICS WITH CONFORMATIONALLY RESTRICTED MONOMERS

TECHNICAL FIELD

This disclosure relates generally to compounds for use in treating disease by regulating the expression of genes or other cell regulatory systems. More specifically, this disclosure relates to single-stranded and multi-stranded compounds, which can regulate the function or expression of nucleic acid molecules expressed in a cell. This disclosure provides a range of compounds having one or more conformationally restricted nucleomonomers (CRN). This disclosure further provides compounds containing one or more CRNs and one or more unlocked nucleomonomers (UNA).

SEQUENCE LISTING

This application includes a Sequence Listing submitted electronically via EFS as an ASCII file created on Apr. 26, 2011, named MAR238US_SeqList_ST25_fin.txt, which is 126,102 bytes in size, and is hereby incorporated by reference in its entirety.

BACKGROUND

RNA interference (RNAi) refers to the cellular process of sequence specific, post-transcriptional gene silencing in animals mediated by small inhibitory nucleic acid molecules, such as a double-stranded RNA (dsRNA) that is homologous to a portion of a targeted messenger RNA (Fire et al., *Nature* 391:806, 1998; Hamilton et al., *Science* 286:950-951, 1999). RNAi has been observed in a variety of organisms, including mammalians (Fire et al., *Nature* 391:806, 1998; Bahramian and Zarbl, *Mol. Cell. Biol.* 19:274-283, 1999; Wianny and Goetz, *Nature Cell Biol.* 2:70, 1999). RNAi can be induced by introducing an exogenous synthetic 21-nucleotide RNA duplex into cultured mammalian cells (Elbashir et al., *Nature* 411:494, 2001a).

The mechanism by which dsRNA mediates targeted gene-silencing can be described as involving two steps. The first step involves degradation of long dsRNAs by a ribonuclease III-like enzyme, referred to as Dicer, into short interfering RNAs (siRNAs) having from 21 to 23 nucleotides with double-stranded regions of about 19 base pairs and a two nucleotide, generally, overhang at each 3'-end (Berstein et al., *Nature* 409:363, 2001; Elbashir et al., *Genes Dev.* 15:188, 2001b; and Kim et al., *Nature Biotech.* 23:222, 2005). The second step of RNAi gene-silencing involves activation of a multi-component nuclease having one strand (guide or antisense strand) from the siRNA and an Argonaute protein to form an RNA-induced silencing complex ("RISC") (Elbashir et al., *Genes Dev.* 15:188, 2001). Argonaute initially associates with a double-stranded siRNA and then endonucleolytically cleaves the non-incorporated strand (passenger or sense strand) to facilitate its release due to resulting thermodynamic instability of the cleaved duplex (Leuschner et al., *EMBO* 7:314, 2006). The guide strand in the activated RISC binds to a complementary target mRNA, which is then cleaved by the RISC to promote gene silencing. Cleavage of the target RNA occurs in the middle of the target region that is complementary to the guide strand (Elbashir et al., 2001b).

What is needed are alternative effective therapeutic modalities useful for treating or preventing diseases or disorders by regulating the expression of genes and other nucleic acid based regulatory systems in a cell.

A need therefore exists for nucleic acid compounds having enhanced stability that are useful in various therapeutic modalities such as RNA interference.

BRIEF SUMMARY

This disclosure provides single-stranded and multi-stranded compounds, which can have one or more double-stranded regions, and can regulate the function or expression of nucleic acid molecules expressed in a cell and/or cell regulatory system dependent upon a nucleic acid in a cell. The disclosure provides a range of compounds having one or more conformationally restricted nucleomonomers (CRN). In some embodiments, a compound of this invention may have one or more conformationally restricted nucleomonomers and one or more hydroxymethyl substituted nucleomonomers (unlocked nucleomonomers, UNA).

In some embodiments, this disclosure provides a range of nucleic acid compound comprising a first strand having from 10 to 60 nucleomonomers, wherein from 1 to 45 of the nucleomonomers of the first strand are the same or different conformationally restricted nucleomonomers each independently selected from Monomer R having the formula:

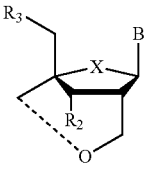

wherein X is independently for each occurrence selected from O, S, $CH_2$, C=O, C=S, $C=CH_2$, CHF or $CF_2$;
$R_2$ and $R_3$ are phosphodiester linkages of the nucleic acid compound; and
B is a nucleobase or nucleobase analog; and
Monomer Q having the formula:

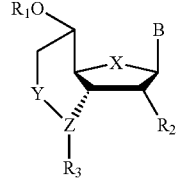

wherein X and Y are independently for each occurrence selected from O, S, $CH_2$, C=O, C=S, $C=CH_2$, CHF, $CF_2$;
Z is independently for each occurrence selected from N or CH;
$R_2$ is independently for each occurrence selected from hydrogen, —F, —OH, —$OCH_3$, —$OCH_3OCH_3$, —$OCH_2CH_3OCH_3$, —$CH_2CH_3OCH_3$, —$CH(OCH_3)$ $CH_3$, and allyl;
$R_1$ and $R_3$ are phosphodiester linkages of the nucleic acid compound; and
B is a nucleobase or nucleobase analog;
wherein each nucleobase or nucleobase analog in the strand is independently selected from adenine, cytosine, guanine, uracil, hypoxanthine, thymine, 7-deazaadenine, inosine, C-phenyl, C-naphthyl, inosine, an azole carboxamide, nebularine, a nitropyrrole, a nitroindole, 2-aminopurine, 2,6-diaminopurine, hypoxanthine, pseudouridine, 5-methyluridine, 5-propynylcytidine, isocytidine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 2-thioribothymidine, 5,6-dihydrouracil, 4-methylindole, ethenoadenine, deoxyuridine, and any existing deoxy analogs of the foregoing.

A compound of this disclosure may contain two or more of the same or different Monomer R. In some embodiments, a compound may contain two or more of the same or different Monomer Q. In certain embodiments, the first strand may have from 19 to 27 nucleomonomers. In some aspects, the compounds of this disclosure RNA, or RNA and DNA.

In certain aspects, a compound of this disclosure may include one or more hydroxymethyl substituted nucleomonomers.

This disclosure further provides a range of compounds having one or two additional strands each having from 7 to 60 nucleomonomers, wherein at least a portion of each of the additional strands is complementary to a portion of the first strand, wherein the first strand and the one or two additional complementary strands can anneal to form one or more duplex portions having a total of from 8 to 60 base pairs in the duplex portions, and wherein one or more of the nucleomonomers of the one or two additional strands is a conformationally restricted nucleomonomer.

A compound of this disclosure may have a sequence targeted for various genes. In some embodiments, a compound of this disclosure may have a sequence targeted for PLK1, a sequence targeted for Survivin BIRC5, a sequence targeted for Factor VII, or a sequence targeted for ApoB.

In certain embodiments, a compound of this disclosure may have conformationally restricted nucleomonomers only present in either of the one or more additional strands, and the first strand does not contain any conformationally restricted nucleomonomers.

In further embodiments, a compound may have a melting temperature increased by at least 1° C. over the same compound that does not contain any conformationally restricted nucleomonomers.

Some compounds of this disclosure are siRNAs, or mdRNAs, or RNA and DNA. In certain embodiments, a compound may have one of the additional strands having one or more nicks. A compound may have one or more duplex gaps that are each independently from 1 to 10 unpaired nucleomonomers in length. A compound may have a blunt end. A compound may have a 3'-end overhang.

This disclosure further contemplates compounds for use in delivering an RNA agent into a cell or an organism. A compound may be used in mediating nucleic acid modification of a target nucleic acid in a cell or an organism. A compound may be used use in decreasing expression levels of a target mRNA in a cell or an organism.

In some embodiments, a compound may be used in inhibiting an endogenous nucleic acid-based regulatory system in a cell or an organism.

In further embodiments, a compound may be used in gene regulation, gene analysis, or RNA interference.

In some aspects, a compound may be used in the manufacture of a medicament for a therapeutic target, including targets for cancers, metabolic diseases, inflammatory diseases, and viral infections.

In certain aspects, a compound may be used in treating a disease, condition or disorder, including cancers, metabolic diseases, inflammatory diseases, and viral infections.

In further aspects, this disclosure contemplates methods for treating a disease, condition or disorder in a subject including cancers, metabolic diseases, inflammatory diseases, and viral infections, the method comprising administering to the subject a compound according to any one of claims 1-23.

BRIEF DESCRIPTION OF THE DRAWINGS

FIG. 1A shows a double-stranded nucleic acid compound.

FIG. 1C shows two nucleic acid compounds having equal length antisense and sense strands, each from 10 to 17 nucleomonomers in length.

FIG. 1D shows a nucleic acid compound complex having a nicked or gapped sense strand and a continuous antisense strand.

FIG. 1E shows a single-stranded nucleic acid compound having from 10 to 40 nucleomonomers.

FIG. 1F shows a single-stranded nucleic acid compound having from 10 to 40 nucleomonomers. The middle region noted as white represents from 4 to 8 deoxynucleotides, and the solid black regions at the 5'-end and 3'-end of the compound are ribonucleotides.

DETAILED DESCRIPTION

This disclosure relates generally to nucleic acid compounds for use in treating disease by gene silencing or modulating the function of a cell regulatory system dependent upon a nucleic acid in a cell and, more specifically, to nucleic acid compounds comprising a single strand of nucleomonomers or double-stranded nucleic acid compound comprising an antisense strand and a continuous or a discontinuous passenger strand, i.e., "sense strand" containing a nick or gap, that decreases expression of a target gene, and to uses of such nucleic acid compound to treat, prevent or manage a disease or condition associated with inappropriate expression of a nucleic acid.

The nuclei acid compounds of this disclosure may further contain one or more conformationally restricted nucleomonomers (CRN), which advantageously enhance the stability of the compound in various therapeutic modalities.

In some embodiments, a nucleic acid compound may contain one or more CRNs and one or more hydroxymethyl substituted nucleomonomers (UNA).

Figure 1A:
FIG. 1A: Example nucleic compounds containing one or more hydroxymethyl substituted nucleomonomer (represented by an "O" in the nucleic acid compound) and/or a conformationally restricted nucleomonomer (represented by a "◊" in the nucleic acid compound).
Figure 1B:
FIG. 1B: The nucleic acid compounds of FIG. 1B have the same configuration as the nucleic acid compound of FIG. 1A, but each has two conformationally restricted nucleomonomers.
Figure 1C:
FIG. 1C.
Figure 1D:
FIG. 1D.
Figure 1E:
FIG. 1E.
Figure 1F:
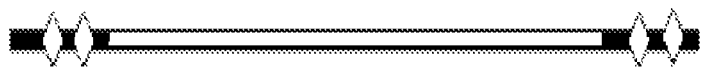
FIG. 1F.

The structures of a range of compounds of this invention are shown in FIG. 1A to FIG. 1F. Example nucleic compounds containing one or more hydroxymethyl substituted nucleomonomers, represented by an "O" in the nucleic acid compound, and/or a conformationally restricted nucleomonomer, represented by a "◇" in the nucleic acid compound. FIG. 1A is a double-stranded nucleic acid compound (e.g., double-stranded RNA (dsRNA) complex) with an antisense strand (bottom strand) and sense strand (top strand) of equal length (e.g., from 18 to 40 nucleomonomers in length) having two hydroxymethyl substituted nucleomonomers at the 3'-end of the sense strand and one hydroxymethyl substituted nucleomonomer at the 5'-end of the sense strand, and two hydroxymethyl substituted nucleomonomers at the 3'-end of the antisense strand. A hydroxymethyl substituted nucleomonomer may also be in the antisense strand of the duplex region. The nucleic acid compounds of FIG. 1B have the same configuration as the nucleic acid compound of FIG. 1A, but each has two conformationally restricted nucleomonomers. In one example, the two conformationally restricted nucleomonomer are in the antisense strand of the duplex region, and in another example, the two conformationally restricted nucleomonomer are in the sense strand of the duplex region. FIG. 1C shows two nucleic acid compounds (double-stranded) having the same modifications as the two nucleic acid compounds of FIG. 1B, but for these two examples, the equal length antisense and sense strands of each are from 10 to 17 nucleomonomers in length. FIG. 1D is a nucleic acid compound complex having a nicked or gapped sense strand (top strand) having two conformationally restricted nucleomonomers that flank the nick or gap in the sense strand (each of the two double-stranded regions of the nucleic acid compound have a conformationally restricted nucleomonomer), and a continuous antisense strand. The two double-stranded regions of the nucleic acid compound are each from 7 to 20 base pairs. The nucleic acid compound has two 3'-end overhangs. FIG. 1E is a Single-Stranded Nucleic Acid compound having from 10 to 40 nucleomonomers and six conformationally restricted nucleomonomers. FIG. 1F is a single-stranded nucleic acid compound having from 10 to 40 nucleomonomers. The middle region (noted as white) represents from 4 to 8 deoxynucleotides, and the solid black regions at the 5'-end and 3'-end of the compound are ribonucleotides, each solid black region has two conformationally restricted nucleomonomers.

Some conformationally restricted nucleomonomers and nucleic acid compounds comprising conformationally restricted nucleomonomers may be found in U.S. Pat. Nos. 6,833,361; 6,403,566 and 6,083,482, each of which is hereby incorporated by reference in its entirety.

In one aspect, this disclosure provides a nucleic acid compound comprising a first strand having from 10 to 60 (or 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60) nucleomonomers, wherein one or more of the nucleomonomers is a conformationally restricted nucleomonomer.

In some embodiments, this disclosure provides a nucleic acid compound comprising a first strand having from 10 to 40 (or 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40) nucleomonomers, wherein one or more of the nucleomonomers is a conformationally restricted nucleomonomer.

In certain embodiments, the melting temperature of the nucleic acid compound is from 40° C. to 100° C., or from 60° C. to 90° C., or from 75° C. to 80° C.

In certain embodiments, from 1% to 75% of the nucleomonomers of the first strand of the nucleic acid compound are conformationally restricted nucleomonomers, or from 20% to 60% of the nucleomonomers of the first strand of the nucleic acid compound are conformationally restricted nucleomonomers, or from 40% to 50% of the nucleomonomers of the first strand of the nucleic acid compound are conformationally restricted nucleomonomers.

In certain embodiments, the nucleic acid compound comprises RNA. In certain embodiments, the nucleic acid compound comprises DNA. In certain embodiments, the nucleic acid compound comprises RNA and DNA.

In other embodiments, the first strand is from 10 to 30 (or 10, 11, 12, 13, 14, 15, 16, 17, 18, 19, 20, 21, 22, 23, 24, 25, 26, 27, 28, 29 or 30) nucleomonomers in length.

Figure 2:
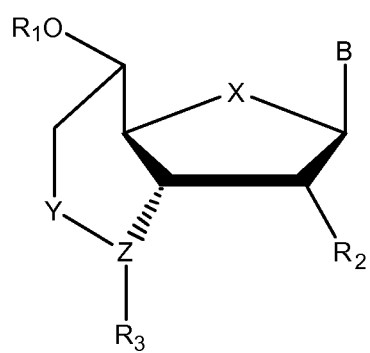
FIG. 2: Examples of conformationally restricted nucleoside analogs that may be incorporated or substituted into nucleic acid compounds.
Figure 2:
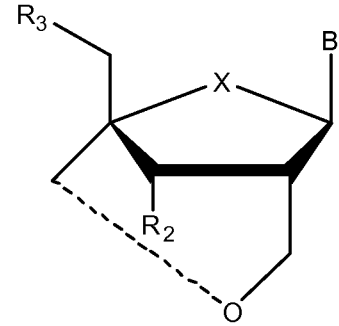

Examples of conformationally restricted nucleoside analogs that may be incorporated or substituted into nucleic acid compounds are shown in FIG. 2. Monomer Q contains a C3'-C5' bridge. Monomer R contains a C2'-C4' bridge. For Monomers Q and R, X may be an —O—, —S—, —CH$_2$, C=O, C=S, C=CH$_2$, CHF or CF$_2$; Z may be an N or CH; R$_2$ may be —H, —OH, —O-alkyl, —F, —SH, —S-alkyl, —S—F, —NH(CH=O), —NH(C=O)—C(1-22) saturated or unsaturated alkyl chain, cycloalkyl, aryl or heterocyclic; and B is a nucleobase or nucleobase analog.

Figure 3:
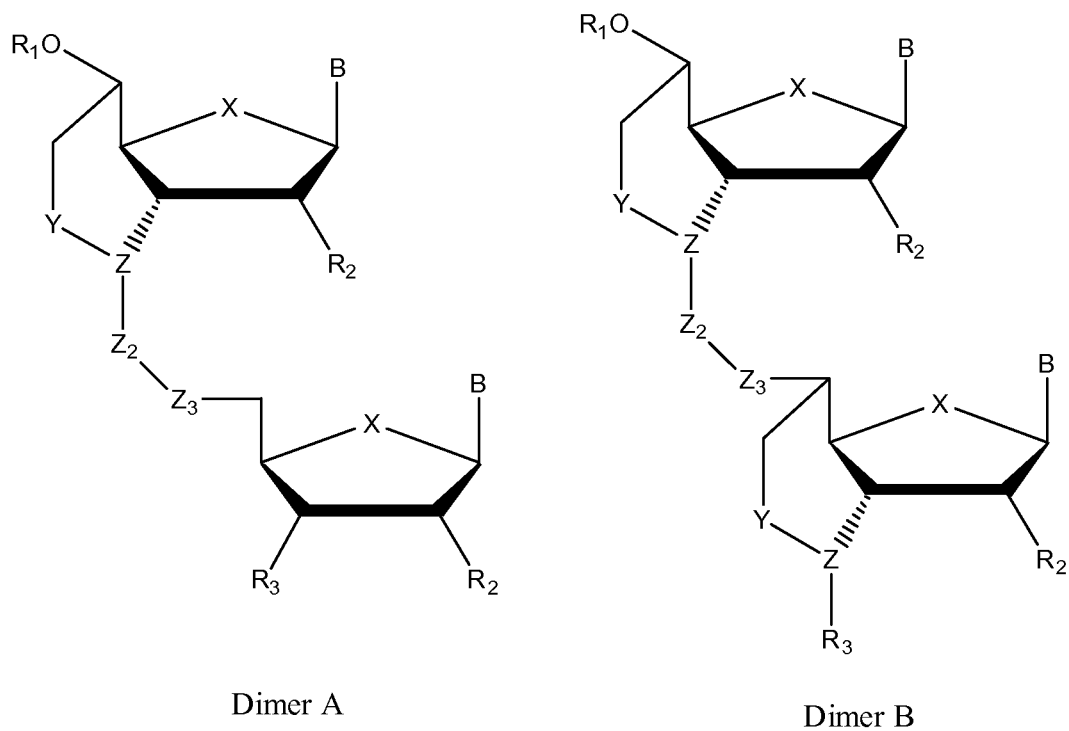
FIG. 3: Dimers A and B represents possible backbone linkages between two Q Monomers.

Dimers A and B shown in FIG. 3 represent possible backbone linkages between two Q Monomers. For Dimers A and B, Z$_2$ and Z$_3$ may be O, S, CO, P(O), P(O)R, P(O)O, CH$_2$; R$_1$ and R$_3$ may be OH, NH, NH2, DMTO, TBDMSO, OP(OR)N(iPr)$_2$, OP(OR)(O)H; and R may be methyl or 2-cyanoethyl.

Embodiments of this invention include a nucleic acid compound comprising a first strand having from 10 to 60 nucleomonomers, wherein from 1 to 45 of the nucleomonomers of the first strand are the same or different conformationally restricted nucleomonomers each independently selected from Monomer R having the formula:

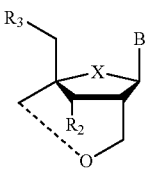

wherein X is independently for each occurrence selected from O, S, CH$_2$, C=O, C=S, C=CH$_2$, CHF or CF$_2$;
R$_2$ and R$_3$ are phosphodiester linkages of the nucleic acid compound; and
B is a nucleobase or nucleobase analog; and
Monomer Q having the formula:

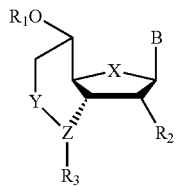

wherein X and Y are independently for each occurrence selected from O, S, $CH_2$, C=O, C=S, C=$CH_2$, CHF, $CF_2$;

Z is independently for each occurrence selected from N or CH;

$R_2$ is independently for each occurrence selected from hydrogen, —F, —OH, —$OCH_3$, —$OCH_3OCH_3$, —$OCH_2CH_3OCH_3$, —$CH_2CH_3OCH_3$, —$CH(OCH_3)CH_3$, allyl;

$R_1$ and $R_3$ are phosphodiester linkages of the nucleic acid compound; and

B is a nucleobase or nucleobase analog;

wherein each nucleobase or nucleobase analog in the strand is independently selected from adenine, cytosine, guanine, uracil, hypoxanthine, thymine, 7-deazaadenine, inosine, C-phenyl, C-naphthyl, inosine, an azole carboxamide, nebularine, a nitropyrrole, a nitroindole, 2-aminopurine, 2,6-diaminopurine, hypoxanthine, pseudouridine, 5-methyluridine, 5-propynylcytidine, isocytidine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 2-thioribothymidine, 5,6-dihydrouracil, 4-methylindole, ethenoadenine, deoxyuridine, and any existing deoxy analogs of the foregoing.

The compound above, wherein the compound contains two or more of the same or different Monomer R.

The compound above, wherein the compound contains two or more of the same or different Monomer Q.

The compound above, wherein the first strand has from 19 to 27 nucleomonomers.

The compound above, wherein the nucleic acid is RNA.

The compound above, wherein the nucleic acid is RNA and DNA.

The compound above, further comprising one or more hydroxymethyl substituted nucleomonomers.

The compound above, further comprising one or two additional strands each having from 7 to 60 nucleomonomers, wherein at least a portion of each of the additional strands is complementary to a portion of the first strand, wherein the first strand and the one or two additional complementary strands can anneal to form one or more duplex portions having a total of from 8 to 60 base pairs in the duplex portions, and wherein one or more of the nucleomonomers of the one or two additional strands is a conformationally restricted nucleomonomer.

The compound above, wherein any one or more of the strands has a sequence for PLK1 selected from SEQ ID NOs:161-220.

The compound above, wherein any one or more of the strands has a sequence for Survivin BIRC5 selected from SEQ ID NOs:1-160.

The compound above, wherein any one or more of the strands has a sequence for Factor VII selected from SEQ ID NOs:474-495.

The compound above, wherein any one or more of the strands has a sequence for ApoB selected from SEQ ID NOs:496-507.

The compound above, wherein any one or more of the strands has a sequence selected from SEQ ID NOs:221-230, 231-245, 246-255, 256-265, 266-275, 276-285, 286-295, 296-305, 306-315, 316-325, 326-335, 336-345, 346-355, 356-365, 366-375, 376-385, 386-395, 396-405, 406-415, 416-425, 426-435, 436-445, 446-455, 456-465, 508-517, and 518-527.

The compound above, wherein the conformationally restricted nucleomonomers are only present in either of the one or more additional strands, and the first strand does not contain any conformationally restricted nucleomonomers.

The compound above, wherein the melting temperature of the compound is increased by at least 1° C. over the same compound that does not contain any conformationally restricted nucleomonomers.

The compound above, wherein the compound is an siRNA.

The compound above, wherein the compound is an mdRNA.

The compound above, wherein the compound is RNA and DNA.

The compound above, wherein one of the additional strands has one or more nicks.

The compound above, wherein the compound has one or more duplex gaps that are each independently from 1 to 10 unpaired nucleomonomers in length.

The compound above, wherein the compound has a blunt end.

The compound above, wherein the compound has a 3'-end overhang.

The compound above, further comprising one or more hydroxymethyl substituted nucleomonomers.

The compound above for use in delivering an RNA agent into a cell or an organism.

The compound above for use in mediating nucleic acid modification of a target nucleic acid in a cell or an organism.

The compound above for use in decreasing expression levels of a target mRNA in a cell or an organism.

The compound above for use in inhibiting an endogenous nucleic acid-based regulatory system in a cell or an organism.

The compound above for use in gene regulation, gene analysis, or RNA interference.

The compound above for use in the manufacture of a medicament for a therapeutic target, including targets for cancers, metabolic diseases, inflammatory diseases, and viral infections.

The compound above for use in treating a disease, condition or disorder, including cancers, metabolic diseases, inflammatory diseases, and viral infections.

A method for treating a disease, condition or disorder in a subject including cancers, metabolic diseases, inflammatory diseases, and viral infections, the method comprising administering to the subject a compound above.

In certain embodiments, the conformationally restricted nucleomonomer is Monomer R and has the following formula:

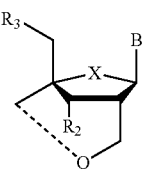

where X is independently for each occurrence selected from O, S, $CH_2$, C=O, C=S, C=$CH_2$, CHF or $CF_2$; $R_2$ and $R_3$ are independently for each occurrence selected from hydrogen, OH, O-alkyl, F, SH, S-alkyl, S—F, CN, $N_3$, $OCH_3$, monophosphate, diphosphate, triphosphate, monophosphate, diphosphonate, triphosphonate, an amino acid ester with an OH group the sugar portion, or a prodrug of the monophosphate, diphosphate, triphosphate, monophosphonate, diphosphonate, or triphosphonate, NH(CH=O), NH(C=O)—C(1-22) saturated or unsaturated alkyl chain, cycloalkyl, aryl or heterocyclic; and B is independently for each occurrence a nucleobase or nucleobase analog.

In certain embodiments, the conformationally restricted nucleomonomer is Monomer Q and has the following formula:

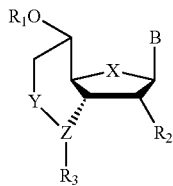

where X and Y are independently for each occurrence selected from O, S, $CH_2$, C=O, C=S, $C=CH_2$, CHF, $CF_2$; Z is independently for each occurrence selected from N or CH; $R_2$ is independently for each occurrence selected from hydrogen, F, OH, or $OCH_3$; $R_1$ and $R_3$ are independently for each occurrence selected from hydrogen, OH, $P(OR)_2$, $P(O)(OR)_2$, $P(S)(OR)_2$, P(O)(SR)OR, acyl, carbobenzoxy, trifluoroacetyl, p-nitrophenyloxycarbonyl, or any suitable protecting group or an activating group for building oligomers; and R is independently for each occurrence selected from H, 2-cyanoethyl, diisopropylamino, alkyl, alkenyl, alkynyl, or a hydrophobic masking group, where R can be same or different from each other in case of $(OR)_2$, or (SR)OR.

In certain embodiments, the nucleic acid compound comprises one or more Monomer R and one or more Monomer Q.

In some embodiments, B represents a nucleobase or nucleobase analog independently selected from adenine, cytosine, guanine, uracil, hypoxanthine, thymine, 7-deazaadenine, inosine, C-phenyl, C-naphthyl, inosine, an azole carboxamide, nebularine, a nitropyrrole, a nitroindole, 2-aminopurine, 2,6-diaminopurine, hypoxanthine, pseudouridine, 5-methyluridine, 5-propynylcytidine, isocytidine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 2-thioribothymidine, 5,6-dihydrouracil, 4-methylindole, ethenoadenine, deoxyuridine, and any existing deoxy analogs of the foregoing.

In some embodiments, B represents a nucleobase or nucleobase analog independently selected from adenine, cytosine, guanine, uracil, and any existing deoxy analogs of the foregoing.

In certain embodiments, the nucleic acid compound further comprises a second strand.

Figure 4:
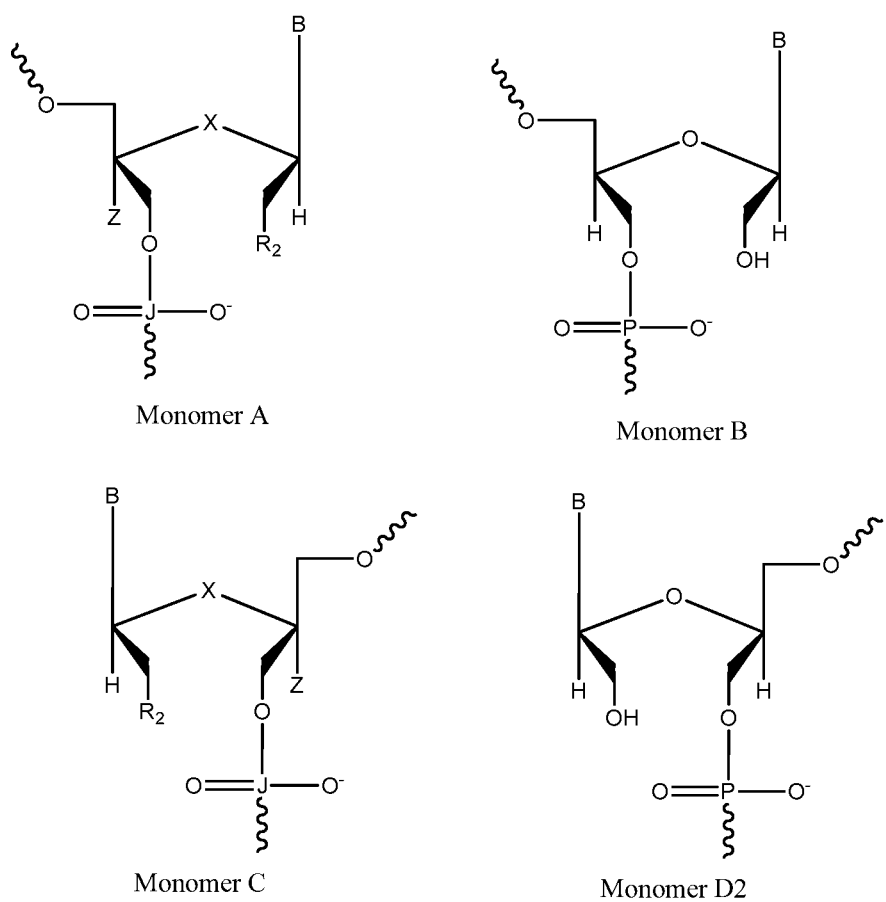
FIG. 4: Monomers A, B, C and D are acyclic non-nucleotide monomers that may be incorporated into nucleic acid compounds.

Monomers A, B, C and D shown in FIG. 4 are acyclic non-nucleotide monomers that may be incorporated into nucleic acid compounds. Monomer B is an exemplary hydroxymethyl substituted nucleomonomer (the hydroxymethyl group is attached at the C1' atom of the acyclic ribose-based scaffold) of Monomer A, and Monomer D is an exemplary hydroxymethyl substituted nucleomonomer (the hydroxymethyl group is attached at the C1' atom of the acyclic-ribose-based scaffold) of Monomer C. Monomers A and B are the D-isoform of an acyclic-ribose-based scaffold, and Monomers C and D are the L-isoform of an acyclic-ribose-based scaffold. For Monomers A and C, X may be an —O—, —S—, or —$CH_2$; Z may be an —H, —OH, —$CH_2OH$, —$CH_3$ or saturated or unsaturated C(2-22) alkyl chain; J may be P or S; $R_2$ may be —H, —OH, —O-alkyl, —F, —SH, —S-alkyl, —S—F, —NH(CH=O), —NH(C=O)—C(1-22) saturated or unsaturated alkyl chain, cycloalkyl, aryl or heterocyclic; and B is a nucleobase or nucleobase analog.

Figure 5:
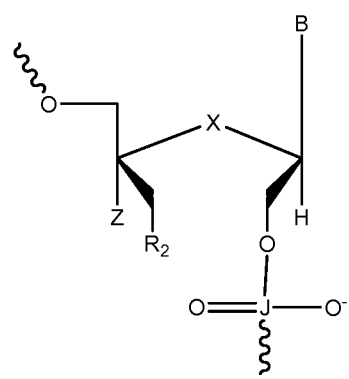
FIG. 5: Monomers E, F, G and H are acyclic non-nucleotide monomers that may be incorporated into nucleic acid compounds.
Figure 5:
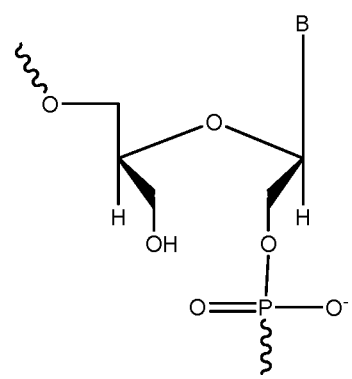
Figure 5:
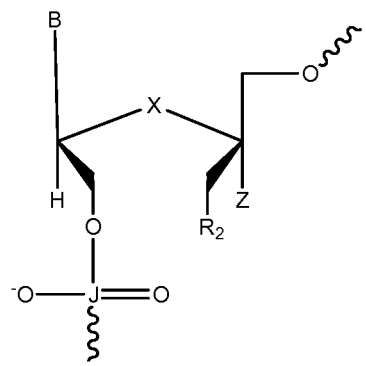
Figure 5:
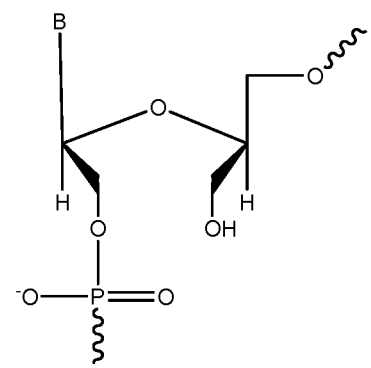

Monomers E, F, G and H shown in FIG. 5 are acyclic non-nucleotide monomers that may be incorporated into nucleic acid compounds. Monomer F is an exemplary hydroxymethyl substituted nucleomonomer (the hydroxymethyl group is attached at the C4' atom of the acyclic ribose-based scaffold) of Monomer E, and Monomer H is an exemplary hydroxymethyl substituted nucleomonomer (the hydroxymethyl group is attached at the C4' atom of the acyclic ribose-based scaffold) of Monomer G. Monomers E and F are the D-isoform of an acyclic-ribose-based scaffold, and Monomers C and D are the L-isoform of an acyclic ribose-based scaffold. For Monomers E and G, X may be an —O—, —S—, or —$CH_2$; Z may be an —H, —OH, —$CH_2OH$, —$CH_3$ or saturated or unsaturated C(2-22) alkyl chain; J may be P or S; $R_2$ may be —H, —OH, —O-alkyl, —F, —SH, —S-alkyl, —S—F, —NH(CH=O), —NH(C=O)—C(1-22) saturated or unsaturated alkyl chain, cycloalkyl, aryl or heterocyclic; and B is a nucleobase or nucleobase analog.

Figure 6:
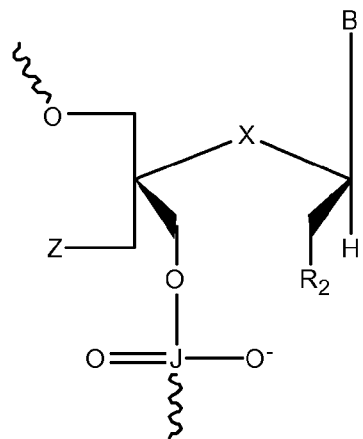
FIG. 6: Monomers I, J, K and L are acyclic non-nucleotide monomers that may be incorporated into nucleic acid compounds.
Figure 6:
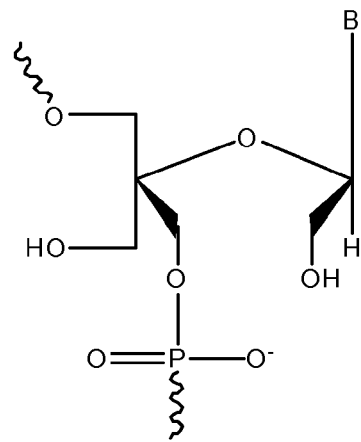
Figure 6:
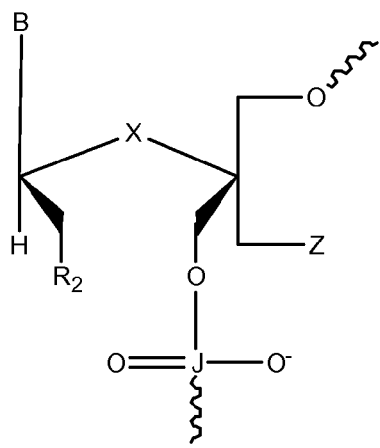
Figure 6:
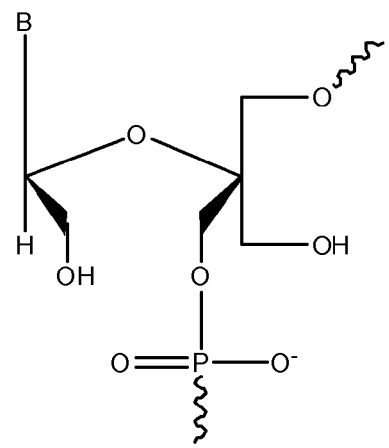

Monomers I, J, K and L shown in FIG. 6 are acyclic non-nucleotide monomers that may be incorporated into nucleic acid compounds. Monomer J is an exemplary hydroxymethyl substituted nucleomonomer (the hydroxymethyl group is attached at the C1' atom of the acyclic ribose-based scaffold) of Monomer I, and Monomer L is an exemplary hydroxymethyl substituted nucleomonomer (the hydroxymethyl group is attached at the C1' atom of the acyclic ribose-based scaffold) of Monomer K. Monomers I and J are the D-isoform of an acyclic-ribose-based scaffold, and Monomers K and L are the L-isoform of an acyclic ribose-based scaffold. For Monomers I and K, X may be an —O—, —S—, or —$CH_2$; Z may be an —H, —OH, —$CH_2OH$, —$CH_3$ or saturated or unsaturated C(2-22) alkyl chain; J may be P or S; $R_2$ may be —H, —OH, —O-alkyl, —F, —SH, —S-alkyl, —S—F, —NH(CH=O), —NH(C=O)—C(1-22) saturated or unsaturated alkyl chain, cycloalkyl, aryl or heterocyclic; and B is a nucleobase or nucleobase analog.

Figure 7:
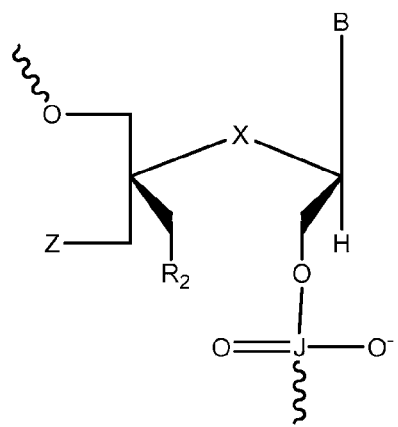
FIG. 7: Monomers M, N, O and P are acyclic non-nucleotide monomers that may be incorporated into nucleic acid compounds.
Figure 7:
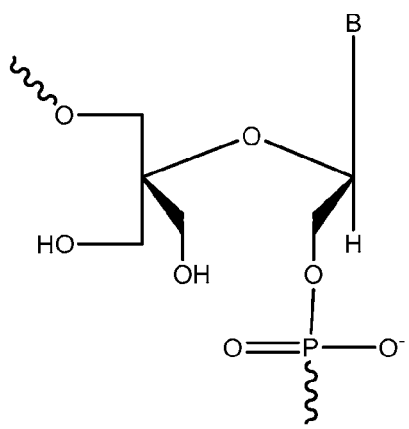
Figure 7:
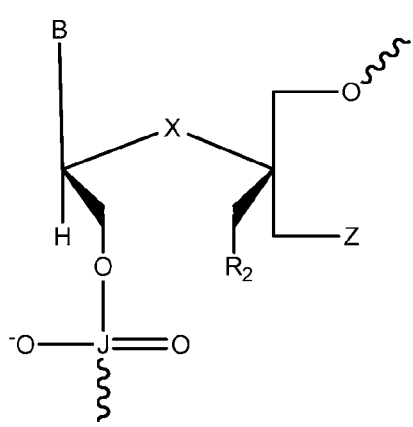
Figure 7:
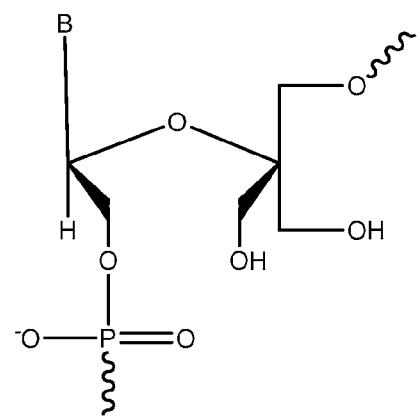

Monomers M, N, O and P shown in FIG. 7 are acyclic non-nucleotide monomers that may be incorporated into nucleic acid compounds. Monomer N is an exemplary hydroxymethyl substituted nucleomonomer (two hydroxymethyl groups are attached at the C4' atom of the acyclic ribose-based scaffold) of Monomer M, and Monomer P is an exemplary hydroxymethyl substituted nucleomonomer (two hydroxymethyl groups are attached at the C4' atom of the acyclic ribose-based scaffold) of Monomer O. Monomers M and N are the D-isoform of an acyclic-ribose-based scaffold, and Monomers O and P are the L-isoform of an acyclic ribose-based scaffold. For Monomers M and O, X may be an —O—, —S—, or —$CH_2$; Z may be an —H, —OH, —$CH_2OH$, —$CH_3$ or saturated or unsaturated C(2-22) alkyl chain; J may be P or S; $R_2$ may be —H, —OH, —O-alkyl, —F, —SH, —S-alkyl, —S—F, —NH(CH=O), —NH(C=O)—C(1-22) saturated or unsaturated alkyl chain, cycloalkyl, aryl or heterocyclic; and B is a nucleobase or nucleobase analog.

Some hydroxymethyl substituted nucleomonomers and nucleic acid compounds comprising hydroxymethyl substituted nucleomonomers may be synthesised using phosphoramidite derivatives using the standard techniques for nucleic acid synthesis. Some methods for synthesis of hydroxymethyl substituted nucleomonomers and hydroxymethyl substituted nucleic acid compounds may be found in PCT International Application PCT/US2008/064417, which is hereby incorporated by reference in its entirety.

In certain embodiments, the nucleic acid compound comprises a hydroxymethyl substituted nucleomonomer. In certain embodiments, the hydroxymethyl substituted nucleomonomer is independently for each occurrence selected from Monomer A, Monomer C, Monomer E, Monomer G, Monomer I, Monomer K, Monomer M, and Monomer O; wherein, X is independently for each occurrence selected from O, S, or —CH$_2$; Z is independently for each occurrence selected from hydrogen, OH, CH$_2$OH, CH$_3$ or saturated or unsaturated C(2-22) alkyl chain; J is independently for each occurrence selected from P or S; R$_2$ is independently for each occurrence selected from hydrogen, OH, O-alkyl, F, SH, S-alkyl, SF, NH(CH=O), NH(C=O)—C(1-22) saturated or unsaturated alkyl chain, cycloalkyl, aryl or heterocyclic; and B is a nucleobase or nucleobase analog.

In certain embodiments, the hydroxymethyl substituted nucleomonomer is independently for each occurrence selected from Monomer B, Monomer D, Monomer F, Monomer H, Monomer J, Monomer L, Monomer N and Monomer P; wherein, B is a nucleobase or nucleobase analog.

In another aspect, the instant disclosure provides a nucleic acid compound comprising a first strand having from 10 to 60 (or 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60) nucleomonomers, and a second strand complementary to the first strand, wherein the first strand and the second strand can anneal to form 8 to 60 (or 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60) base pairs, and wherein one or more of the nucleomonomers of the first strand or the second strand is a conformationally restricted nucleomonomer.

In certain embodiments, the melting temperature of the nucleic acid compound is from 40° C. to 100° C., or from 60° C. to 90° C., or from 75° C. to 80° C.

In certain embodiments, from 1% to 75% of the nucleomonomers of the first strand or second strand of the nucleic acid compound are conformationally restricted nucleomonomers, or from 20% to 60% of the nucleomonomers of the first strand or second strand of the nucleic acid compound are conformationally restricted nucleomonomers, or wherein from 40% to 50% of the nucleomonomers of the first strand or second strand of the nucleic acid compound are conformationally restricted nucleomonomers.

In certain embodiments, the first strand is from 10 to 40 nucleomonomers in length. In other embodiments, the first strand is from 15 to 35 nucleomonomers in length. In yet other embodiments, the first strand is from 18 to 30 nucleomonomers in length. In yet other embodiments, the first strand is from 19 to 23 nucleomonomers in length. In yet another embodiment, the first strand is from 25 to 30 nucleomonomers in length.

In certain embodiments, the second strand is from 8 to 60 nucleomonomers in length. In other embodiments, the second strand is from 10 to 40 nucleomonomers in length. In yet other embodiments, the second strand is from 15 to 35 nucleomonomers in length. In yet other embodiments, the second strand is from 18 to 30 nucleomonomers in length. In yet other embodiments, the second strand is from 19 to 23 nucleomonomers in length. In yet another embodiment, the second strand is from 25 to 30 nucleomonomers in length.

In certain embodiments, any one or more of the last 15 positions at the 3'-end of the first strand is occupied by the same or different conformationally restricted nucleomonomer.

In certain embodiments, any one or more of the last 10 positions at the 3'-end of the first strand is occupied by the same or different conformationally restricted nucleomonomer.

In certain embodiments, two or more of the last 15 positions at the 3'-end of the first strand is occupied by the same or different conformationally restricted nucleomonomer.

In certain embodiments, two or more of the last 10 positions at the 3'-end of the first strand is occupied by the same or different conformationally restricted nucleomonomer.

In certain embodiments, three or more of the last 15 positions at the 3'-end of the first strand is occupied by the same or different conformationally restricted nucleomonomer.

In certain embodiments, three or more of the last 10 positions at the 3'-end of the first strand is occupied by the same or different conformationally restricted nucleomonomer.

In certain embodiments, four or more of the last 15 positions at the 3'-end of the first strand is occupied by the same or different conformationally restricted nucleomonomer.

In certain embodiments, four or more of the last 10 positions at the 3'-end of the first strand is occupied by the same or different conformationally restricted nucleomonomer.

In certain embodiments, five or more of the last 15 positions at the 3'-end of the first strand is occupied by the same or different conformationally restricted nucleomonomer.

In certain embodiments, five or more of the last 10 positions at the 3'-end of the first strand is occupied by the same or different conformationally restricted nucleomonomer.

In certain embodiment, any one or more of the last 15 positions at the 5'-end of the second strand is occupied by the same or different conformationally restricted nucleomonomer.

In certain embodiment, any one or more of the last 10 positions at the 5'-end of the second strand is occupied by the same or different conformationally restricted nucleomonomer.

In certain embodiments, two or more of the last 15 positions at the 5'-end of the second strand is occupied by the same or different conformationally restricted nucleomonomer.

In certain embodiments, two or more of the last 10 positions at the 5'-end of the second strand is occupied by the same or different conformationally restricted nucleomonomer.

In certain embodiments, three or more of the last 15 positions at the 5'-end of the second strand is occupied by the same or different conformationally restricted nucleomonomer.

In certain embodiments, three or more of the last 10 positions at the 5'-end of the second strand is occupied by the same or different conformationally restricted nucleomonomer.

In certain embodiments, four or more of the last 15 positions at the 5'-end of the second strand is occupied by the same or different conformationally restricted nucleomonomer.

In certain embodiments, four or more of the last 10 positions at the 5'-end of the second strand is occupied by the same or different conformationally restricted nucleomonomer.

In certain embodiments, five or more of the last 15 positions at the 5'-end of the second strand is occupied by the same or different conformationally restricted nucleomonomer.

In certain embodiments, five or more of the last 10 positions at the 5'-end of the second strand is occupied by the same or different conformationally restricted nucleomonomer.

In certain embodiments, the nucleic acid compound comprises RNA. In certain embodiments, the nucleic acid compound comprises DNA. In certain embodiments, the nucleic acid compound comprises RNA and DNA.

In certain embodiments, the nucleic acid compound is an siRNA.

In certain embodiments, the conformationally restricted nucleomonomer is Monomer R and has the following formula:

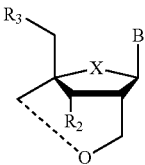

where X is independently for each occurrence selected from O, S, $CH_2$, C=O, C=S, C=$CH_2$, CHF or $CF_2$; $R_2$ and $R_3$ are independently for each occurrence selected from hydrogen, OH, O-alkyl, F, SH, S-alkyl, S—F, CN, $N_3$, $OCH_3$, monophosphate, diphosphate, triphosphate, monophosphate, diphosphate, triphosphonate, an amino acid ester with an OH group the sugar portion, or a prodrug of the monophosphate, diphosphate, triphosphate, monophosphonate, diphosphonate, or triphosphonate, NH(CH=O), NH(C=O)—C(1-22) saturated or unsaturated alkyl chain, cycloalkyl, aryl or heterocyclic; and B is independently for each occurrence a nucleobase or nucleobase analog.

In certain embodiments, the conformationally restricted nucleomonomer is Monomer Q and has the following formula:

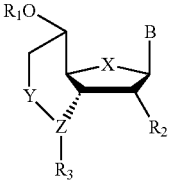

where X and Y are independently for each occurrence selected from O, S, $CH_2$, C=O, C=S, C=$CH_2$, CHF, $CF_2$; Z is independently for each occurrence selected from N or CH; $R_2$ is independently for each occurrence selected from hydrogen, F, OH, or $OCH_3$; $R_1$ and $R_3$ are independently for each occurrence selected from hydrogen, OH, $P(OR)_2$, $P(O)(OR)_2$, $P(S)(OR)_2$, $P(O)(SR)OR$, acyl, carbobenzoxy, trifluoroacetyl, p-nitrophenyloxycarbonyl, or any suitable protecting group or an activating group for building oligomers; and R is independently for each occurrence selected from H, 2-cyanoethyl, diisopropylamino, alkyl, alkenyl, alkynyl, or a hydrophobic masking group, where R can be same or different from each other in case of $(OR)_2$, or (SR)OR.

In certain embodiments, the nucleic acid compound comprises one or more Monomer R and one or more Monomer Q.

In certain embodiments, the first and second strands are a contiguous strand of nucleomonomers. In certain embodiments, the second strand has one or more nicks. In certain embodiments, the second strand has one or more gaps. In a related embodiment, the one or more gaps, independently for each occurrence, comprise from 1 to 10 (or 1, 2, 3, 4, 5, 6, 7, 8, 9 or 10) unpaired nucleomonomers.

In certain embodiments, the nucleic acid comprises two or more conformationally restricted nucleomonomers, wherein the two or more conformationally restricted nucleomonomers flank the one or more gaps of the second strand of the nucleic acid.

In certain embodiments, the nucleic acid comprises two or more conformationally restricted nucleomonomers, wherein the two or more conformationally restricted nucleomonomers flank the one or more nicks of the second strand of the nucleic acid.

In certain embodiments, the nucleic acid compound has a blunt end. In certain embodiments, the nucleic acid compound has a 3'-end overhang.

In certain embodiments, the nucleic acid compound comprises a hydroxymethyl substituted nucleomonomer. In certain embodiments, the hydroxymethyl substituted nucleomonomer is independently for each occurrence selected from Monomer A, Monomer C, Monomer E, Monomer G, Monomer I, Monomer K, Monomer M, and Monomer O; wherein, X is independently for each occurrence selected from O, S, or —$CH_2$; Z is independently for each occurrence selected from hydrogen, OH, $CH_2OH$, $CH_3$ or saturated or unsaturated C(2-22) alkyl chain; J is independently for each occurrence selected from P or S; $R_2$ is independently for each occurrence selected from hydrogen, OH, O-alkyl, F, SH, S-alkyl, SF, NH(CH=O), NH(C=O)—C(1-22) saturated or unsaturated alkyl chain, cycloalkyl, aryl or heterocyclic; and B is a nucleobase or nucleobase analog.

In certain embodiments, the hydroxymethyl substituted nucleomonomer is independently for each occurrence selected from Monomer B, Monomer D, Monomer F, Monomer H, Monomer J, Monomer L, Monomer N and Monomer P; wherein, B is a nucleobase or nucleobase analog.

In another aspect, the instant disclosure provides a use of a nucleic acid compound as described herein for the manufacture of a medicament for use in the therapy of disease.

In another aspect, the instant disclosure provides a method for reducing the expression of a gene or reducing the function an endogenous nucleic acid based regulatory system of a cell, comprising administering a nucleic acid compound as described herein to a cell, wherein the nucleic acid compound reduces the expression of the gene in the cell.

In another aspect, the instant disclosure provides a method for reducing the function of an endogenous nucleic acid based regulatory system of a cell, comprising administering a nucleic acid compound described herein to a cell, wherein the nucleic acid compound reduces the function of the endogenous nucleic acid based regulatory system in the cell.

In certain embodiments, the cell is a human cell.

In another aspect, the instant disclosure provides a method for treating or managing a disease or condition in a subject associated, linked, and/or resulting from aberrant nucleic acid expression, comprising administering to the subject in need of treatment or management a nucleic acid compound as disclosed herein, wherein the nucleic acid compound reduces the expression or function of the nucleic acid thereby treating or managing the disease or condition.

In further embodiments, the nucleic acid compound is a single stranded nucleic acid comprising from 10 to 40 (or 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40) nucleomonomers, wherein one or more of the from 10 to 40 nucleomonomers is a conformationally restricted nucleomonomer.

In certain embodiments, the minimum percent occurrence of conformationally restricted nucleomonomers of the nucleic acid compound is greater than 0% and less than 95%, or greater than 0% and less than 85%, or greater than 0% and less than 75%, or greater than 10% and less than 70%, or greater than 20% and less than 60%, or greater than 30% and less than 55%, or greater than 40% and less than 60%.

In certain embodiments, the percent of nucleomonomers of the from 10 to 40 nucleomonomers of nucleic acid compound that are conformationally restricted nucleomonomers is from 1% to 95%, or from 5% to 90%, or from 10% to 85%, or from 15% to 80%, or from 20% to 75%, or from 25% to 70%, or from 30% to 65%, or from 35% to 60%, or from 40% to 55%, or from 45% to 50%.

In certain embodiments, every other nucleomonomer of the nucleic acid compound is a conformationally locked nucleomonomer.

In certain embodiments, every third nucleomonomer counting from the 5'-end of the nucleic acid compound is a conformationally locked nucleomonomer.

In certain embodiments, every forth nucleomonomer counting from the 5'-end of the nucleic acid compound is a conformationally locked nucleomonomer.

In certain embodiments, every fifth nucleomonomer counting from the 5'-end of the nucleic acid compound is a conformationally locked nucleomonomer.

In certain embodiments, every sixth nucleomonomer counting from the 5'-end of the nucleic acid compound is a conformationally locked nucleomonomer.

In certain embodiments, every seventh nucleomonomer counting from the 5'-end of the nucleic acid compound is a conformationally locked nucleomonomer.

In certain embodiments, every eight nucleomonomer counting from the 5'-end of the nucleic acid compound is a conformationally locked nucleomonomer.

In certain embodiments, every ninth nucleomonomer counting from the 5'-end of the nucleic acid compound is a conformationally locked nucleomonomer.

In certain embodiments, every tenth nucleomonomer counting from the 5'-end of the nucleic acid compound is a conformationally locked nucleomonomer.

In certain embodiments, the conformationally restricted nucleomonomer is Monomer R and has the following formula:

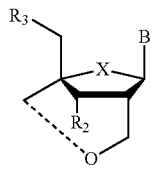

wherein X is independently for each occurrence selected from O, S, $CH_2$, C=O, C=S, $C=CH_2$, CHF or $CF_2$; $R_2$ and $R_3$ are independently for each occurrence selected from hydrogen, OH, O-alkyl, F, SH, S-alkyl, S—F, CN, $N_3$, $OCH_3$, monophosphate, diphosphate, triphosphate, monophosphate, diphosphonate, triphosphonate, an amino acid ester with an OH group the sugar portion, or a prodrug of the monophosphate, diphosphate, triphosphate, monophosphonate, diphosphonate, or triphosphonate, NH(CH=O), NH(C=O)—C(1-22) saturated or unsaturated alkyl chain, cycloalkyl, aryl or heterocyclic; and B is independently for each occurrence a nucleobase or nucleobase analog.

In certain embodiments, the conformationally restricted nucleomonomer is Monomer Q and has the following formula:

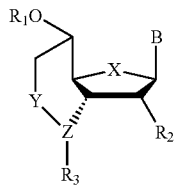

wherein X and Y are independently for each occurrence selected from O, S, $CH_2$, C=O, C=S, $C=CH_2$, CHF, $CF_2$; Z is independently for each occurrence selected from N or CH; $R_2$ is independently for each occurrence selected from hydrogen, F, OH, or $OCH_3$; $R_1$ and $R_3$ are independently for each occurrence selected from hydrogen, OH, $P(OR)_2$, $P(O)(OR)_2$, $P(S)(OR)_2$, P(O)(SR)OR, acyl, carbobenzoxy, trifluoroacetyl, p-nitrophenyloxycarbonyl, or any suitable protecting group or an activating group for building oligomers; and R is independently for each occurrence selected from H, 2-cyanoethyl, diisopropylamino, alkyl, alkenyl, alkynyl, or a hydrophobic masking group, where R can be same or different from each other in case of $(OR)_2$, or (SR)OR.

In certain embodiments, the nucleic acid compound comprises one or more of the same or different Monomer R and one or more of the same or different Monomer Q.

In certain embodiments, the nucleic acid compound comprises one or more hydroxymethyl substituted nucleomonomer that are independently for each occurrence selected from Monomer A, Monomer C, Monomer E, Monomer G, Monomer I, Monomer K, Monomer M, and Monomer O; wherein, X is independently for each occurrence selected from O, S, or —$CH_2$; Z is independently for each occurrence selected from hydrogen, OH, $CH_2OH$, $CH_3$ or saturated or unsaturated C(2-22) alkyl chain; J is independently for each occurrence selected from P or S; $R_2$ is independently for each occurrence selected from hydrogen, OH, O-alkyl, F, SH, S-alkyl, SF, NH(CH=O), NH(C=O)—C(1-22) saturated or unsaturated alkyl chain, cycloalkyl, aryl or heterocyclic; and B is a nucleobase or nucleobase analog.

In certain embodiments, the nucleic acid compound comprises one or more hydroxymethyl substituted nucleomonomers that are independently for each occurrence selected from Monomer B, Monomer D, Monomer F, Monomer H, Monomer J, Monomer L, Monomer N and Monomer P; wherein, B is a nucleobase or nucleobase analog.

In certain embodiments, the nucleic acid compound comprises one or more RNA nucleomonomers.

In certain embodiments, the nucleic acid compound comprises one or more DNA nucleomonomers.

In certain embodiments, the nucleic acid compound comprises RNA and DNA nucleomonomers.

In certain embodiments, the nucleic acid compound comprises one or more hydroxymethyl substituted nucleomonomers.

In certain embodiments, the nucleic acid compound has the following formula:

5' A-B-A 3' wherein, A is independently, for each occurrence, a sequence of from 3 to 16 (or 3, 4, 5, 6, 7, 8, 9, 10, 11, 12, 13, 14, 15, or 16) nucleomonomers, wherein the minimum percent occurrence of conformationally restricted nucleomonomers of the sequence is greater than 0% and less than 95%, or greater than 0% and less than 85%, or greater than 0% and less than 75%, or greater than 10% and less than 70%, or greater than 20% and less than 60%, or greater than 30% and less than 55%, or greater than 40% and less than 60%; and wherein B is independently, for each occurrence, is a sequence of from 4 to 8 (or 4, 5, 6, 7, or 8) nucleomonomers.

In certain embodiments, the nucleic acid compound is from 10 to 40 nucleomonomers in length, from 12 to 30 nucleomonomers in length or from 12 to 14 nucleomonomers in length.

In certain embodiments, the conformationally restricted nucleomonomer is Monomer R and has the following formula:

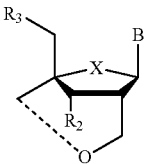

wherein X is independently for each occurrence selected from O, S, CH$_2$, C=O, C=S, C=CH$_2$, CHF or CF$_2$; R$_2$ and R$_3$ are independently for each occurrence selected from hydrogen, OH, O-alkyl, F, SH, S-alkyl, S—F, CN, N$_3$, OCH$_3$, monophosphate, diphosphate, triphosphate, monophosphate, diphosphonate, triphosphonate, an amino acid ester with an OH group the sugar portion, or a prodrug of the monophosphate, diphosphate, triphosphate, monophosphonate, diphosphonate, or triphosphonate, NH(CH=O), NH(C=O)—C(1-22) saturated or unsaturated alkyl chain, cycloalkyl, aryl or heterocyclic; and B is independently for each occurrence a nucleobase or nucleobase analog.

In certain embodiments, the conformationally restricted nucleomonomer is Monomer Q and has the following formula:

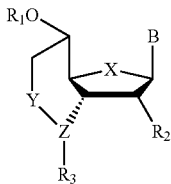

wherein X and Y are independently for each occurrence selected from O, S, CH$_2$, C=O, C=S, C=CH$_2$, CHF, CF$_2$; Z is independently for each occurrence selected from N or CH; R$_2$ is independently for each occurrence selected from hydrogen, F, OH, or OCH$_3$; R$_1$ and R$_3$ are independently for each occurrence selected from hydrogen, OH, P(OR)$_2$, P(O)(OR)$_2$, P(S)(OR)$_2$, P(O)(SR)OR, acyl, carbobenzoxy, trifluoroacetyl, p-nitrophenyloxycarbonyl, or any suitable protecting group or an activating group for building oligomers; and R is independently for each occurrence selected from H, 2-cyanoethyl, diisopropylamino, alkyl, alkenyl, alkynyl, or a hydrophobic masking group, where R can be same or different from each other in case of (OR)$_2$, or (SR)OR.

In certain embodiments, the nucleic acid compound comprises one or more of the same or different Monomer R and one or more of the same or different Monomer Q.

In certain embodiments, the nucleic acid compound comprises one or more hydroxymethyl substituted nucleomonomers that are independently for each occurrence selected from Monomer A, Monomer C, Monomer E, Monomer G, Monomer I, Monomer K, Monomer M, and Monomer O; wherein, X is independently for each occurrence selected from O, S, or —CH$_2$; Z is independently for each occurrence selected from hydrogen, OH, CH$_2$OH, CH$_3$ or saturated or unsaturated C(2-22) alkyl chain; J is independently for each occurrence selected from P or S; R$_2$ is independently for each occurrence selected from hydrogen, OH, O-alkyl, F, SH, S-alkyl, SF, NH(CH=O), NH(C=O)—C(1-22) saturated or unsaturated alkyl chain, cycloalkyl, aryl or heterocyclic; and B is a nucleobase or nucleobase analog.

In certain embodiments, the one or more hydroxymethyl substituted nucleomonomers are independently for each occurrence selected from Monomer B, Monomer D, Monomer F, Monomer H, Monomer J, Monomer L, Monomer N and Monomer P; wherein, B is a nucleobase or nucleobase analog.

In certain embodiments, B does not contain a conformationally restricted nucleomonomer.

In certain embodiments, the nucleomonomers of B are DNA, phosphorothioates or a combination thereof.

In certain embodiments, the nucleomonomers of A are RNA.

In certain embodiments, the nucleic acid compound functions as an antisense RNA, microRNA or antagomir.

In another embodiment, the nucleic acid compound is single stranded and has no double stranded region.

In another aspect, the instant disclosure provides a nucleic acid compound comprising a first strand having from 10 to 60 (or 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60) nucleomonomers, and a second strand complementary to the first strand, wherein the first strand and the second strand can anneal to form 8 to 60 base pairs, and wherein one or more of the nucleomonomers of the first strand or the second strand is a conformationally restricted nucleomonomer.

In certain embodiments, the melting temperature of the nucleic acid compound is from 40° C. to 100° C., or from 60° C. to 90° C., or from 75° C. to 80° C.

In certain embodiments, from 1% to 75% of the nucleomonomers of the first strand or second strand of the nucleic acid compound are conformationally restricted nucleomonomers, or from 20% to 60% of the nucleomonomers of the first strand or second strand of the nucleic acid compound are conformationally restricted nucleomonomers, or wherein from 40% to 50% of the nucleomonomers of the first strand or second strand of the nucleic acid compound are conformationally restricted nucleomonomers.

In certain embodiments, the first strand is from 10 to 40 nucleomonomers in length. In other embodiments, the first strand is from 15 to 35 nucleomonomers in length. In yet other embodiments, the first strand is from 18 to 30 nucleomonomers in length. In yet other embodiments, the first strand is from 19 to 23 nucleomonomers in length. In yet another embodiment, the first strand is from 25 to 30 nucleomonomers in length.

In certain embodiments, the second strand is from 8 to 60 nucleomonomers in length. In other embodiments, the second strand is from 10 to 40 nucleomonomers in length. In yet other embodiments, the second strand is from 15 to 35 nucleomonomers in length. In yet other embodiments, the second strand is from 18 to 30 nucleomonomers in length. In yet other embodiments, the second strand is from 19 to 23 nucleomonomers in length. In yet another embodiment, the second strand is from 25 to 30 nucleomonomers in length.

In certain embodiments, any one or more of positions 1, 2, 3, 4, 5, 6, 7, 8, 9, 10, 11, 12, 13, 14, and 15 counting from the 3'-end of the first strand is occupied by the same or different conformationally restricted nucleomonomer.

In certain embodiments, any one or more of positions 1, 2, 3, 4, 5, 6, 7, 8, 9, and 10 counting from the 3'-end of the first strand is occupied by the same or different conformationally restricted nucleomonomer.

In certain embodiments, any one or more of positions 1, 2, 3, 4, 5, 6, 7, 8, 9, 10, 11, 12, 13, 14, and 15 counting from the 5'-end of the second strand is occupied by the same or different conformationally restricted nucleomonomer.

In certain embodiments, any one or more of positions 1, 2, 3, 4, 5, 6, 7, 8, 9, and 10 counting from the 5'-end of the second strand is occupied by the same or different conformationally restricted nucleomonomer.

In certain embodiments, the nucleic acid compound comprises RNA. In certain embodiments, the nucleic acid compound comprises DNA. In certain embodiments, the nucleic acid compound comprises RNA and DNA.

In certain embodiments, the nucleic acid compound is an siRNA.

In certain embodiments, the conformationally restricted nucleomonomer is Monomer R and has the following formula:

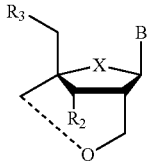

where X is independently for each occurrence selected from O, S, CH$_2$, C=O, C=S, C=CH$_2$, CHF or CF$_2$; R$_2$ and R$_3$ are independently for each occurrence selected from hydrogen, OH, O-alkyl, F, SH, S-alkyl, S—F, CN, N$_3$, OCH$_3$, monophosphate, diphosphate, triphosphate, monophosphate, diphosphonate, triphosphonate, an amino acid ester with an OH group the sugar portion, or a prodrug of the monophosphate, diphosphate, triphosphate, monophosphonate, diphosphonate, or triphosphonate, NH(CH=O), NH(C=O)—C(1-22) saturated or unsaturated alkyl chain, cycloalkyl, aryl or heterocyclic; and B is independently for each occurrence a nucleobase or nucleobase analog.

In certain embodiments, the conformationally restricted nucleomonomer is Monomer Q and has the following formula:

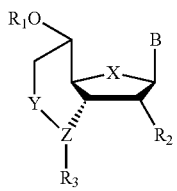

where X and Y are independently for each occurrence selected from O, S, CH$_2$, C=O, C=S, C=CH$_2$, CHF, CF$_2$; Z is independently for each occurrence selected from N or CH; R$_2$ is independently for each occurrence selected from hydrogen, F, OH, or OMe; R$_1$ and R$_3$ are independently for each occurrence selected from hydrogen, OH, P(OR)$_2$, P(O)(OR)$_2$, P(S)(OR)$_2$, P(O)(SR)OR, acyl, carbobenzoxy, trifluoroacetyl, p-nitrophenyloxycarbonyl, or any suitable protecting group or an activating group for building oligomers; and R is independently for each occurrence selected from H, 2-cyanoethyl, diisopropylamino, alkyl, alkenyl, alkynyl, or a hydrophobic masking group, where R can be same or different from each other in case of (OR)$_2$, or (SR)OR.

In certain embodiments, the nucleic acid compound comprises one or more Monomer R and one or more Monomer Q.

In certain embodiments, the first and second strands are a contiguous strand of nucleomonomers. In certain embodiments, the second strand has one or more nicks. In certain embodiments, the second strand has one or more gaps. In a related embodiment, the one or more gaps, independently for each occurrence, comprise from 1 to 10 (or 1, 2, 3, 4, 5, 6, 7, 8, 9 or 10) unpaired nucleomonomers.

In certain embodiments, the nucleic acid compound has a blunt end. In certain embodiments, the nucleic acid compound has a 3'-end overhang.

In certain embodiments, the nucleic acid compound comprises a hydroxymethyl substituted nucleomonomer. In certain embodiments, the hydroxymethyl substituted nucleomonomer is independently for each occurrence selected from Monomer A, Monomer C, Monomer E, Monomer G, Monomer I, Monomer K, Monomer M, and Monomer O; wherein, X is independently for each occurrence selected from O, S, or —CH$_2$; Z is independently for each occurrence selected from hydrogen, OH, CH$_2$OH, CH$_3$ or saturated or unsaturated C(2-22) alkyl chain; J is independently for each occurrence selected from P or S; R$_2$ is independently for each occurrence selected from hydrogen, OH, O-alkyl, F, SH, S-alkyl, SF, NH(CH=O), NH(C=O)—C(1-22) saturated or unsaturated alkyl chain, cycloalkyl, aryl or heterocyclic; and B is a nucleobase or nucleobase analog.

In certain embodiments, the hydroxymethyl substituted nucleomonomer is independently for each occurrence selected from Monomer B, Monomer D, Monomer F, Monomer H, Monomer J, Monomer L, Monomer N and Monomer P; wherein, B is a nucleobase or nucleobase analog.

In one aspect, the disclosure provide for a nucleic acid compound comprising a sense strand and an antisense strand, and a double-stranded region having from 10 to 24 (or 10, 11, 12, 13, 14, 15, 16, 17, 18, 19, 20, 21, 22, 23 or 24) base pairs, wherein any one or more of the last three positions at the 5'-end of the sense strand is occupied by the same or different hydroxymethyl substituted nucleomonomer, and wherein any one or more of the last 10 positions at the 3'-end of the antisense strand is occupied by the same or different conformationally restricted nucleomonomer.

In one aspect, the disclosure provide for a nucleic acid compound comprising a sense strand and an antisense strand, and a double-stranded region having from 10 to 24 (or 10, 11, 12, 13, 14, 15, 16, 17, 18, 19, 20, 21, 22, 23 or 24) base pairs, wherein any one or more of the last three positions at the 5'-end of the sense strand is occupied by the same or different hydroxymethyl substituted nucleomonomer, and wherein any one or more of the last 10 positions at the 5'-end of the sense strand is occupied by the same or different conformationally restricted nucleomonomer.

In another aspect, the antisense strand is from 10 to 24 nucleomonomers in length.

In another aspect, the senses strand is from 10 to 24 nucleomonomers in length.

In another aspect, no more than two conformationally restricted nucleomonomers are adjacent to one another.

In another aspect, the nucleic acid compound further comprises that one or both of the last two positions of the 3'-end of the sense strand are occupied by the same or different hydroxymethyl substituted nucleomonomer.

In yet another aspect, the nucleic acid compound further comprises that one or both of the last two positions of the 3'-end of the antisense strand is occupied by the same or different hydroxymethyl substituted nucleomonomer.

In another aspect, the nucleic acid compound further comprises that one or more of positions 5, 6, 7 and 8 of the antisense strand are occupied by the same or different hydroxymethyl substituted nucleomonomer, wherein the positions of the antisense strand are numbered beginning with position 1 at the 5' end of the antisense strand.

In another aspect, the nucleic acid compound further comprises that one or both of the last two positions of the 3'-end of the sense strand are occupied by the same or different hydroxymethyl substituted nucleomonomer.

In yet another aspect, the nucleic acid compound further comprises that one or both of the last two positions of the 3'-end of the antisense strand is occupied by the same or different hydroxymethyl substituted nucleomonomer.

In certain embodiments, the conformationally restricted nucleomonomer is Monomer R and has the following formula:

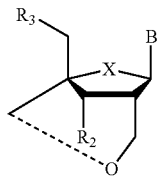

wherein X is independently for each occurrence selected from O, S, $CH_2$, C=O, C=S, $C=CH_2$, CHF or $CF_2$; $R_2$ and $R_3$ are independently for each occurrence selected from hydrogen, OH, O-alkyl, F, SH, S-alkyl, S—F, CN, $N_3$, $OCH_3$, monophosphate, diphosphate, triphosphate, monophosphate, diphosphate, triphosphate, monophosphonate, diphosphonate, or triphosphonate, NH(CH=O), NH(C=O)—C(1-22) saturated or unsaturated alkyl chain, cycloalkyl, aryl or heterocyclic; and B is independently for each occurrence a nucleobase or nucleobase analog.

In certain embodiments, the conformationally restricted nucleomonomer is Monomer Q and has the following formula:

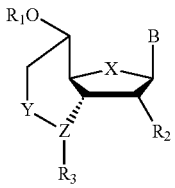

wherein X and Y are independently for each occurrence selected from O, S, $CH_2$, C=O, C=S, $C=CH_2$, CHF, $CF_2$; Z is independently for each occurrence selected from N or CH; $R_2$ is independently for each occurrence selected from hydrogen, F, OH, or OMe; $R_1$ and $R_3$ are independently for each occurrence selected from hydrogen, OH, $P(OR)_2$, $P(O)(OR)_2$, $P(S)(OR)_2$, P(O)(SR)OR, acyl, carbobenzoxy, trifluoroacetyl, p-nitrophenyloxycarbonyl, or any suitable protecting group or an activating group for building oligomers; and R is independently for each occurrence selected from H, 2-cyanoethyl, diisopropylamino, alkyl, alkenyl, alkynyl, or a hydrophobic masking group, where R can be same or different from each other in case of $(OR)_2$, or (SR)OR.

In certain embodiments, the nucleic acid compound comprises one or more of the same or different Monomer R and one or more of the same or different Monomer Q.

In certain embodiments, the nucleic acid compound comprises one or more hydroxymethyl substituted nucleomonomers that are independently for each occurrence selected from Monomer A, Monomer C, Monomer E, Monomer G, Monomer I, Monomer K, Monomer M, and Monomer O; wherein, X is independently for each occurrence selected from O, S, or —$CH_2$; Z is independently for each occurrence selected from hydrogen, OH, $CH_2OH$, $CH_3$ or saturated or unsaturated C(2-22) alkyl chain; J is independently for each occurrence selected from P or S; $R_2$ is independently for each occurrence selected from hydrogen, OH, O-alkyl, F, SH, S-alkyl, SF, NH(CH=O), NH(C=O)—C(1-22) saturated or unsaturated alkyl chain, cycloalkyl, aryl or heterocyclic; and B is a nucleobase or nucleobase analog.

In certain embodiments, the one or more hydroxymethyl substituted nucleomonomers are independently for each occurrence selected from Monomer B, Monomer D, Monomer F, Monomer H, Monomer J, Monomer L, Monomer N and Monomer P; wherein, B is a nucleobase or nucleobase analog.

In another aspect, the nucleic acid compound has a double-stranded region of 10 to 23 base pairs. In another aspect, the nucleic acid compound has a double-stranded region of 12 to 21 base pairs. In another aspect, the nucleic acid compound has a double-stranded region of 14 to 21 base pairs. In another aspect, the nucleic acid compound has a double-stranded region of 15 to 21 base pairs. In another aspect, the nucleic acid compound has a double-stranded region of 16 to 21 base pairs.

In another aspect, the nucleic acid compound has a blunt end.

In another aspect, the nucleic acid compound further comprises a 3'-end overhang. In another aspect, the 3'-end overhang comprises nucleotides. In another aspect, the 3'-end overhang comprises non-nucleotide monomers. In another aspect, the 3'-end overhang comprise both nucleotides and non-nucleotide monomers.

In another aspect, the 3'-end overhang is from 1 to 20 (or 1, 2, 3, 4, 5, 6, 7, 8, 9, 10, 11, 12, 13, 14, 15, 16, 17 or 18) nucleomonomers in length. In another aspect, the 3'-end overhang is from 3 to 18 (or 3, 4, 5, 6, 7, 8, 9, 10, 11, 12, 13, 14, 15, 16, 17, 18, 19 or 20) nucleomonomers in length. In another aspect, the 3'-end overhang is from 5 to 16 (or 5, 6, 7, 8, 9, 10, 11, 12, 13, 14, 15 or 16) nucleomonomers in length.

In any aspect disclosed herein, the 3'-end overhang is an overhang of the sense strand.

In any aspect disclosed herein, the 3'-end overhang is an overhang of the antisense strand. In any aspect disclosed herein, the sense strand has a 3'-overhang and the antisense strand has a 3'-end overhang, which may be the same or different. In another aspect, the 3'-end overhang is from 1 to 5 (or 1, 2, 3, 4 or 5) nucleomonomers in length.

In another aspect, the 3'-end overhang is selected from the group of overhangs with a length of 1 nucleotide, 2 nucleotides, 3 nucleotides, 4 nucleotides, 5 nucleotides, 6 nucleotides, 7 nucleotides and 8 nucleotides, and/or 1 hydroxymethyl substituted nucleomonomer, 2 hydroxymethyl substituted nucleomonomers, 3 hydroxymethyl substituted nucleomonomers, 4 hydroxymethyl substituted nucleomonomers, 5 hydroxymethyl substituted nucleomonomers, 6 hydroxymethyl substituted nucleomonomers, 7 hydroxymethyl substituted nucleomonomers and 8 hydroxymethyl substituted nucleomonomers, and combinations thereof.

In one aspect, this disclosure provides for a nucleic acid compound comprising a sense strand and an antisense strand, and a double-stranded region having from 25 to 60 (or 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60) base pairs, wherein the last position of the 3'-end of the antisense strand and the last position of the 3'-end of the sense strand are occupied by the same or different hydroxymethyl substituted nucleomonomer, and wherein any one or more of the last 15 positions at the 3'-end of the antisense strand is occupied by the same or different conformationally restricted nucleomonomer.

In one aspect, this disclosure provides for a nucleic acid compound comprising a sense strand and an antisense strand, and a double-stranded region having from 25 to 60 (or 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60) base pairs, wherein the last position of the 3'-end of the antisense strand and the last position of the 3'-end of the sense strand are occupied by the same or different hydroxymethyl substituted nucleomonomer, and wherein any one or more of the last 15 positions at the 5'-end of the sense strand is occupied by the same or different conformationally restricted nucleomonomer.

In another aspect, the antisense strand is from 25 to 60 (or 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60) nucleomonomers in length.

In another aspect, the senses strand is from 25 to 60 (or 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60) nucleomonomers in length.

In some embodiments, no more than two conformationally restricted nucleomonomers are adjacent to one another.

In another aspect, the last two positions of the 3'-end of the antisense strand are occupied by the same or different hydroxymethyl substituted nucleomonomer.

In certain embodiments, the conformationally restricted nucleomonomer is Monomer R and has the following formula:

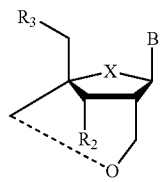

wherein X is independently for each occurrence selected from O, S, CH$_2$, C=O, C=S, C=CH$_2$, CHF or CF$_2$; R$_2$ and R$_3$ are independently for each occurrence selected from hydrogen, OH, O-alkyl, F, SH, S-alkyl, S—F, CN, N$_3$, OCH$_3$, monophosphate, diphosphate, triphosphate, monophosphate, diphosphonate, triphosphonate, an amino acid ester with an OH group the sugar portion, or a prodrug of the monophosphate, diphosphate, triphosphate, monophosphonate, diphosphonate, or triphosphonate, NH(CH=O), NH(C=O)—C(1-22) saturated or unsaturated alkyl chain, cycloalkyl, aryl or heterocyclic; and B is independently for each occurrence a nucleobase or nucleobase analog.

In certain embodiments, the conformationally restricted nucleomonomer is Monomer Q and has the following formula:

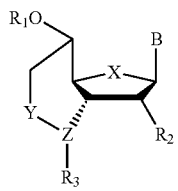

wherein X and Y are independently for each occurrence selected from O, S, CH$_2$, C=O, C=S, C=CH$_2$, CHF, CF$_2$; Z is independently for each occurrence selected from N or CH; R$_2$ is independently for each occurrence selected from hydrogen, F, OH, or OMe; R$_1$ and R$_3$ are independently for each occurrence selected from hydrogen, OH, P(OR)$_2$, P(O)(OR)$_2$, P(S)(OR)$_2$, P(O)(SR)OR, acyl, carbobenzoxy, trifluoroacetyl, p-nitrophenyloxycarbonyl, or any suitable protecting group or an activating group for building oligomers; and R is independently for each occurrence selected from H, 2-cyanoethyl, diisopropylamino, alkyl, alkenyl, alkynyl, or a hydrophobic masking group, where R can be same or different from each other in case of (OR)$_2$, or (SR)OR.

In certain embodiments, the nucleic acid compound comprises one or more of the same or different Monomer R and one or more of the same or different Monomer Q.

In certain embodiments, the nucleic acid compound comprises one or more hydroxymethyl substituted nucleomonomers that are independently for each occurrence selected from Monomer A, Monomer C, Monomer E, Monomer G, Monomer I, Monomer K, Monomer M, and Monomer O; wherein, X is independently for each occurrence selected from O, S, or —CH$_2$; Z is independently for each occurrence selected from hydrogen, OH, CH$_2$OH, CH$_3$ or saturated or unsaturated C(2-22) alkyl chain; J is independently for each occurrence selected from P or S; R$_2$ is independently for each occurrence selected from hydrogen, OH, O-alkyl, F, SH, S-alkyl, SF, NH(CH=O), NH(C=O)—C(1-22) saturated or unsaturated alkyl chain, cycloalkyl, aryl or heterocyclic; and B is a nucleobase or nucleobase analog.

In certain embodiments, the one or more hydroxymethyl substituted nucleomonomers are independently for each occurrence selected from Monomer B, Monomer D, Monomer F, Monomer H, Monomer J, Monomer L, Monomer N and Monomer P; wherein, B is a nucleobase or nucleobase analog.

In another aspect, the nucleic acid compound has a double-stranded region of 25 to 40 base pairs. In another aspect, the nucleic acid compound has a double-stranded region of 25 to 35 base pairs. In another aspect, the nucleic acid compound has a double-stranded region of 25 to 30 base pairs. In another aspect, the nucleic acid compound has a double-stranded region of 25 to 27 base pairs.

In another aspect, the nucleic acid compound has a blunt end.

In another aspect, the nucleic acid compound further comprises a 3'-end overhang. In another aspect, the 3'-end overhang comprises nucleotides. In another aspect, the 3'-end overhang comprises non-nucleotide monomers. In another aspect, the 3'-end overhang comprise both nucleotides and non-nucleotide monomers.

In another aspect, the 3'-end overhang is from 1 to 20 (or 1, 2, 3, 4, 5, 6, 7, 8, 9, 10, 11, 12, 13, 14, 15, 16, 17 or 18) nucleomonomers in length. In another aspect, the 3'-end overhang is from 3 to 18 (or 3, 4, 5, 6, 7, 8, 9, 10, 11, 12, 13, 14, 15, 16, 17, 18, 19 or 20) nucleomonomers in length.

In another aspect, the 3'-end overhang is from 5 to 16 (or 5, 6, 7, 8, 9, 10, 11, 12, 13, 14, 15 or 16) nucleomonomers in length. In any aspect disclosed herein, the 3'-end overhang is an overhang of the sense strand. In any aspect disclosed herein, the 3'-end overhang is an overhang of the antisense strand. In any aspect disclosed herein, the sense strand has a 3'-overhang and the antisense strand has a 3'-end overhang, which may be the same or different. In another aspect, the 3'-end overhang is from 1 to 5 (or 1, 2, 3, 4 or 5) nucleomonomers in length.

In another aspect, the 3'-end overhang is selected from the group of overhangs with a length of 1 nucleotide, 2 nucleotides, 3 nucleotides, 4 nucleotides, 5 nucleotides, 6 nucleotides, 7 nucleotides and 8 nucleotides, and/or 1 hydroxymethyl substituted nucleomonomer, 2 hydroxymethyl substituted nucleomonomers, 3 hydroxymethyl substituted nucleomonomers, 4 hydroxymethyl substituted nucleomonomers, 5 hydroxymethyl substituted nucleomonomers, 6 hydroxymethyl substituted nucleomonomers, 7 hydroxymethyl substituted nucleomonomers and 8 hydroxymethyl substituted nucleomonomers, and combinations thereof.

In one aspect, this disclosure provide for a nucleic acid compound comprising a sense strand and an antisense strand, and a double-stranded region having from 25 to 60 (or 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60) base pairs, wherein one or more of positions 21, 22 and 23 of the sense strand is occupied by the same or different hydroxymethyl substituted nucleomonomer, wherein the positions of the sense strand are numbered beginning with position 1 at the 5'-end of the sense strand, and wherein any one or more of the last 15 positions at the 3'-end of the antisense strand is occupied by the same or different conformationally restricted nucleomonomer.

In one aspect, this disclosure provide for a nucleic acid compound comprising a sense strand and an antisense strand, and a double-stranded region having from 25 to 60 (or 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60) base pairs, wherein one or more of positions 21, 22 and 23 of the sense strand is occupied by the same or different hydroxymethyl substituted nucleomonomer, wherein the positions of the sense strand are numbered beginning with position 1 at the 5'-end of the sense strand, and wherein any one or more of the last 15 positions at the 5'-end of the sense strand is occupied by the same or different conformationally restricted nucleomonomer.

In one aspect, this disclosure provide for a nucleic acid compound comprising a sense strand and an antisense strand, and a double-stranded region having from 25 to 60 (or 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60) base pairs, wherein one or more of positions 18, 19, 20, 21, and 22 of the antisense strand are occupied by the same or different hydroxymethyl substituted nucleomonomer, wherein the positions of the sense strand are numbered beginning with position 1 at the 3'-end of the antisense strand, and wherein any one or more of the last 15 positions at the 3'-end of the antisense strand is occupied by the same or different conformationally restricted nucleomonomer.

In another aspect, the nucleic acid compound further comprises that one or both of the last two positions of the 3'-end of the antisense strand are occupied by the same or different hydroxymethyl substituted nucleomonomer.

In another aspect, the nucleic acid compound further comprises that one or both of the last two positions of the 3'-end of the sense strand are occupied by the same or different hydroxymethyl substituted nucleomonomer.

In another aspect, the hydroxymethyl substituted nucleomonomer is a 2'-3'-seco-nucleomonomer.

In another aspect, the hydroxymethyl substituted nucleomonomer is selected from:

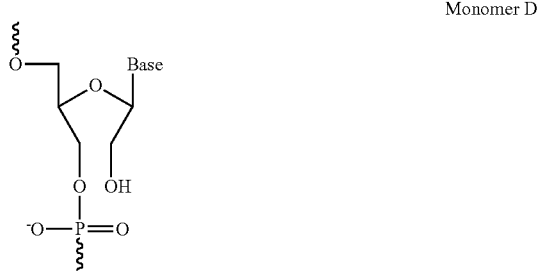

Monomer D

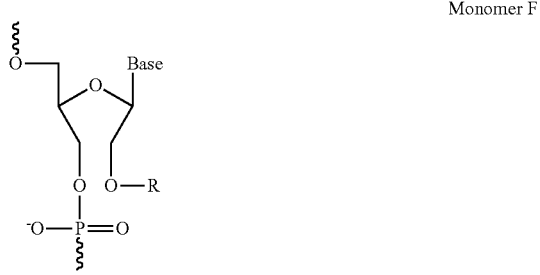

Monomer F

Monomer G

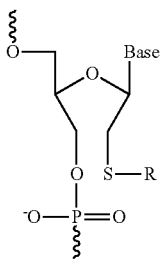

Monomer H

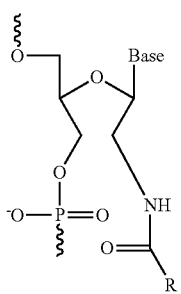

Monomer I

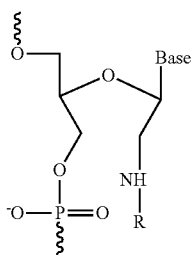

Monomer J

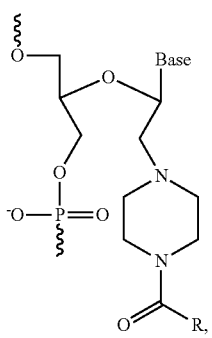

wherein R is selected from the group consisting of a hydrogen, an alkyl group, a cholesterol derivative, a fluorophore, a polyamine, a fatty acid, an amino acid, a saccharide, and a polypeptide, wherein Base is any purine, pyrimidine, or derivative or analogue thereof.

In certain embodiments, the conformationally restricted nucleomonomer is Monomer R and has the following formula:

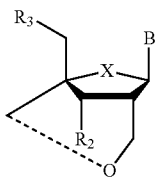

wherein X is independently for each occurrence selected from O, S, $CH_2$, C=O, C=S, C=$CH_2$, CHF or $CF_2$; $R_2$ and $R_3$ are independently for each occurrence selected from hydrogen, OH, O-alkyl, F, SH, S-alkyl, S—F, CN, $N_3$, $OCH_3$, monophosphate, diphosphate, triphosphate, monophosphate, diphosphonate, triphosphonate, an amino acid ester with an OH group the sugar portion, or a prodrug of the monophosphate, diphosphate, triphosphate, monophosphonate, diphosphonate, or triphosphonate, NH(CH=O), NH(C=O)—C(1-22) saturated or unsaturated alkyl chain, cycloalkyl, aryl or heterocyclic; and B is independently for each occurrence a nucleobase or nucleobase analog.

In certain embodiments, the conformationally restricted nucleomonomer is Monomer Q and has the following formula:

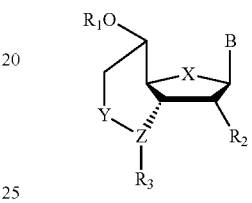

wherein X and Y are independently for each occurrence selected from O, S, $CH_2$, C=O, C=S, C=$CH_2$, CHF, $CF_2$; Z is independently for each occurrence selected from N or CH; $R_2$ is independently for each occurrence selected from hydrogen, F, OH, or OMe; $R_1$ and $R_3$ are independently for each occurrence selected from hydrogen, OH, $P(OR)_2$, $P(O)(OR)_2$, $P(S)(OR)_2$, P(O)(SR)OR, acyl, carbobenzoxy, trifluoroacetyl, p-nitrophenyloxycarbonyl, or any suitable protecting group or an activating group for building oligomers; and R is independently for each occurrence selected from H, 2-cyanoethyl, diisopropylamino, alkyl, alkenyl, alkynyl, or a hydrophobic masking group, where R can be same or different from each other in case of $(OR)_2$, or (SR)OR.

In certain embodiments, the nucleic acid compound comprises one or more of the same or different Monomer R and one or more of the same or different Monomer Q.

In certain embodiments, the one or more hydroxymethyl substituted nucleomonomer are independently for each occurrence selected from Monomer A, Monomer C, Monomer E, Monomer G, Monomer I, Monomer K, Monomer M, and Monomer O; wherein, X is independently for each occurrence selected from O, S, or —$CH_2$; Z is independently for each occurrence selected from hydrogen, OH, $CH_2OH$, $CH_3$ or saturated or unsaturated C(2-22) alkyl chain; J is independently for each occurrence selected from P or S; $R_2$ is independently for each occurrence selected from hydrogen, OH, O-alkyl, F, SH, S-alkyl, SF, NH(CH=O), NH(C=O)—C(1-22) saturated or unsaturated alkyl chain, cycloalkyl, aryl or heterocyclic; and B is a nucleobase or nucleobase analog.

In certain embodiments, the one or more hydroxymethyl substituted nucleomonomers are independently for each occurrence selected from Monomer B, Monomer D, Monomer F, Monomer H, Monomer J, Monomer L, Monomer N and Monomer P; wherein, B is a nucleobase or nucleobase analog.

In another aspect, the nucleic acid compound further comprises a nucleotide analogue selected from the group consisting of 2'-O-alkyl-RNA monomers, 2'-amino-DNA monomers, 2'-fluoro-DNA monomers, LNA monomers, PNA monomers, HNA monomers, ANA monomers, FANA monomers, CeNA monomers, ENA monomers, DNA monomers, and INA monomers.

In another aspect, the instant disclosure provides for the use of a nucleic acid compound as disclosed herein for the manufacture of a medicament for use in the therapy of cancer.

In a related aspect, one or more hydroxymethyl substituted nucleomonomer(s) are at one or more of positions 5, 6, 7 or 8 counting from the 5'-end of the antisense strand.

In a related aspect, one or more hydroxymethyl substituted nucleomonomer(s) are at position 7 counting from the 5'-end of the antisense strand.

In a related aspect, the double-stranded region has 19 or 20 base pairs.

In a related aspect, the sense strand and the antisense strand each have 21 or 22 nucleomonomers.

In a related aspect, the dsRNA has a 3'-end overhang.

In a related aspect, the dsRNA has a blunt end.

In another aspect, the disclosure provides a nucleic acid compound (e.g., dsRNA) that downregulates the expression of a gene, the nucleic acid compound comprising a sense strand and an antisense strand, a double-stranded region having from 25 to 60 base pairs, and wherein the last two nucleomonomers of the 3'-end of the antisense strand and the last nucleomonomer of the 3'-end of the sense strand are hydroxymethyl substituted nucleomonomers, and wherein any one or more of the last 15 positions at the 3'-end of the antisense strand is occupied by the same or different conformationally restricted nucleomonomer.

In another aspect, the disclosure provides a nucleic acid compound (e.g., dsRNA) that downregulates the expression of a gene, the nucleic acid compound comprising a sense strand and an antisense strand, a double-stranded region having from 25 to 60 base pairs, and wherein the last two nucleomonomers of the 3'-end of the antisense strand and the last nucleomonomer of the 3'-end of the sense strand are hydroxymethyl substituted nucleomonomers, and wherein any one or more of the last 15 positions at the 5'-end of the sense strand is occupied by the same or different conformationally restricted nucleomonomer.

In another aspect, the disclosure provides a nucleic acid compound (e.g., dsRNA) that downregulates the expression of a gene, the nucleic acid compound comprising a sense strand and an antisense strand, a double-stranded region having from 25 to 60 base pairs, and wherein one or more hydroxymethyl substituted nucleomonomer(s) are at one or more positions of the sense strand that inhibit processing of the dsRNA by a Dicer enzyme, and wherein any one or more of the last 15 positions at the 3'-end of the antisense strand is occupied by the same or different conformationally restricted nucleomonomer.

In another aspect, the disclosure provides a nucleic acid compound (e.g., dsRNA) that downregulates the expression of a gene, the nucleic acid compound comprising a sense strand and an antisense strand, a double-stranded region having from 25 to 60 base pairs, and wherein one or more hydroxymethyl substituted nucleomonomer(s) are at one or more positions of the sense strand that inhibit processing of the dsRNA by a Dicer enzyme, and wherein any one or more of the last 15 positions at the 5'-end of the sense strand is occupied by the same or different conformationally restricted nucleomonomer.

In a related aspect, one or more hydroxymethyl substituted nucleomonomer(s) are at one or more of positions 21, 22 or 23 of the sense strand counting from the 5'-end of the sense strand.

In a related aspect, one or more hydroxymethyl substituted nucleomonomer(s) are at one or more of positions 18, 19, 20 21 or 22 of the antisense strand counting from the 3'-end of the antisense strand.

In one aspect, the instant disclosure provides for a nucleic acid compound comprising at least three strands, designated herein as A, S1 and S2 (A:S1S2), wherein the S1 strand and the S2 strand are complementary to, and form base pairs (bp) with, non-overlapping regions of the A strand. Thus, for the nucleic acid compounds described herein; the double-stranded region (or a duplex) formed by the annealing of the S1 strand and the A strand is distinct from the double-stranded region formed by the annealing of the S2 strand and the A strand. An A:S1 duplex may be separated from an A:S2 duplex by a "gap" resulting from at least one unpaired nucleomonomer in the A strand that is positioned between the A:S1 duplex and the A: S2 duplex and that is distinct from any one or more unpaired nucleomonomer at the 3' end of either or both of the A, S1, and/or S2 strand. Alternatively, an A:S1 duplex may be separated from an A:S2 duplex by a "nick" (lack of a phosphodiester bond between adjacent nucleomonomers) such that there are no unpaired nucleotides in the A strand that are positioned between the A:S1 duplex and the A:S2 duplex such that the only unpaired nucleotide, if any, is at the 3' end of either or both of the A, S1, and/or S2 strand.

In one aspect, the nucleic acid compound comprises a first strand that is complementary to a target nucleic acid (e.g., mRNA or other nucleic acid molecule), and a second strand and a third strand that are each complementary to non-overlapping regions of the first strand, wherein the second strand and third strands can anneal with the first strand to form at least two double-stranded regions separated by a gap of from 1 to 10 (or 1, 2, 3, 4, 5, 6, 7, 8, 9, or 10) nucleomonomers or nick, wherein the total number of base pairs of the double-stranded is from about 10 base pairs to about 60 base pairs, and wherein one or more of the nucleomonomers is a conformationally restricted nucleomonomer.

In certain embodiments, the minimum percent occurrence of conformationally restricted nucleomonomers of the nucleic acid compound is greater than 0% and less than 95%, or greater than 0% and less than 85%, or greater than 0% and less than 75%, or greater than 10% and less than 70%, or greater than 20% and less than 60%, or greater than 30% and less than 55%, or greater than 40% and less than 60%.

In certain embodiments, the percent of nucleomonomers that are conformationally restricted nucleomonomers is from 1% to 95%, or from 5% to 90% (or 5%, 10%, 15%, 20%, 25%, 30%, 35%, 40%, 45%, 50%, 55%, 60%, 65%, 70%, 75%, 80%, 85% or 90%), or from 10% to 85% (or 10%, 15%, 20%, 25%, 30%, 35%, 40%, 45%, 50%, 55%, 60%, 65%, 70%, 75%, 80%, or 85%), or from 15% to 80%, or from 20% to 75%, or from 25% to 70%, or from 30% to 65%, or from 35% to 60%, or from 40% to 55%, or from 45% to 50%.

In certain embodiments, from 1% to 75% of the nucleomonomers of the first strand of the nucleic acid compound are conformationally restricted nucleomonomers, or from 20% to 60% of the nucleomonomers of the first strand of the nucleic acid compound are conformationally restricted nucleomonomers, or wherein from 40% to 50% of the nucleomonomers of the first strand of the nucleic acid compound are conformationally restricted nucleomonomers.

In certain embodiments, from 1% to 75% of the nucleomonomers of the second strand of the nucleic acid compound are conformationally restricted nucleomonomers, or from 20% to 60% of the nucleomonomers of the second strand of the nucleic acid compound are conformationally restricted nucleomonomers, or wherein from 40% to 50% of the nucleomonomers of the second strand of the nucleic acid compound are conformationally restricted nucleomonomers.

In certain embodiments, from 1% to 75% of the nucleomonomers of the second strand or the third strand of the nucleic acid compound are conformationally restricted nucleomonomers, or from 20% to 60% of the nucleomonomers of the second strand or the third strand of the nucleic acid compound are conformationally restricted nucleomonomers, or wherein from 40% to 50% of the nucleomonomers of the second strand or the third strand of the nucleic acid compound are conformationally restricted nucleomonomers.

In certain embodiments, every other nucleomonomer of the nucleic acid compound is a conformationally locked nucleomonomer.

In certain embodiments, every third nucleomonomer counting from the 5'-end of the nucleic acid compound is a conformationally locked nucleomonomer.

In certain embodiments, every forth nucleomonomer counting from the 5'-end of the nucleic acid compound is a conformationally locked nucleomonomer.

In certain embodiments, every fifth nucleomonomer counting from the 5'-end of the nucleic acid compound is a conformationally locked nucleomonomer.

In certain embodiments, every sixth nucleomonomer counting from the 5'-end of the nucleic acid compound is a conformationally locked nucleomonomer.

In certain embodiments, every seventh nucleomonomer counting from the 5'-end of the nucleic acid compound is a conformationally locked nucleomonomer.

In certain embodiments, every eight nucleomonomer counting from the 5'-end of the nucleic acid compound is a conformationally locked nucleomonomer.

In certain embodiments, every ninth nucleomonomer counting from the 5'-end of the nucleic acid compound is a conformationally locked nucleomonomer.

In certain embodiments, every tenth nucleomonomer counting from the 5'-end of the nucleic acid compound is a conformationally locked nucleomonomer.

In certain embodiments, each double-stranded region comprises an equal number of the same or different conformationally restricted nucleomonomers.

In certain embodiments, each double-stranded region comprises one or more conformationally restricted nucleomonomers, wherein the one or more conformationally restricted nucleomonomers may be the same or different.

In certain embodiments, the conformationally restricted nucleomonomer is Monomer R and has the following formula:

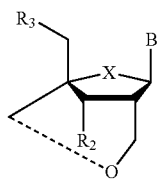

wherein X is independently for each occurrence selected from O, S, $CH_2$, C=O, C=S, C=$CH_2$, CHF or $CF_2$; $R_2$ and $R_3$ are independently for each occurrence selected from hydrogen, OH, O-alkyl, F, SH, S-alkyl, S—F, CN, $N_3$, $OCH_3$, monophosphate, diphosphate, triphosphate, monophosphate, diphosphonate, triphosphonate, an amino acid ester with an OH group the sugar portion, or a prodrug of the monophosphate, diphosphate, triphosphate, monophosphonate, diphosphonate, or triphosphonate, NH(CH=O), NH(C=O)—C(1-22) saturated or unsaturated alkyl chain, cycloalkyl, aryl or heterocyclic; and B is independently for each occurrence a nucleobase or nucleobase analog.

In certain embodiments, the conformationally restricted nucleomonomer is Monomer Q and has the following formula:

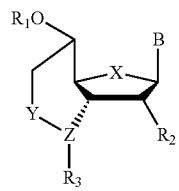

wherein X and Y are independently for each occurrence selected from O, S, $CH_2$, C=O, C=S, C=$CH_2$, CHF, $CF_2$; Z is independently for each occurrence selected from N or CH; $R_2$ is independently for each occurrence selected from hydrogen, F, OH, or OMe; $R_1$ and $R_3$ are independently for each occurrence selected from hydrogen, OH, $P(OR)_2$, $P(O)(OR)_2$, $P(S)(OR)_2$, $P(O)(SR)OR$, acyl, carbobenzoxy, trifluoroacetyl, p-nitrophenyloxycarbonyl, or any suitable protecting group or an activating group for building oligomers; and R is independently for each occurrence selected from H, 2-cyanoethyl, diisopropylamino, alkyl, alkenyl, alkynyl, or a hydrophobic masking group, where R can be same or different from each other in case of $(OR)_2$, or $(SR)OR$.

In certain embodiments, the nucleic acid compound comprises one or more of the same or different Monomer R and one or more of the same or different Monomer Q.

In certain embodiments the hydroxymethyl substituted nucleomonomer is independently for each occurrence selected from Monomer A, Monomer C, Monomer E, Monomer G, Monomer I, Monomer K, Monomer M, and Monomer O; wherein, X is independently for each occurrence selected from O, S, or —$CH_2$; Z is independently for each occurrence selected from hydrogen, OH, $CH_2OH$, $CH_3$ or saturated or unsaturated C(2-22) alkyl chain; J is independently for each occurrence selected from P or S; $R_2$ is independently for each occurrence selected from hydrogen, OH, O-alkyl, F, SH, S-alkyl, SF, NH(CH=O), NH(C=O)—C(1-22) saturated or unsaturated alkyl chain, cycloalkyl, aryl or heterocyclic; and B is a nucleobase or nucleobase analog.

In certain embodiments, the hydroxymethyl substituted nucleomonomer is independently for each occurrence selected from Monomer B, Monomer D, Monomer F, Monomer H, Monomer J, Monomer L, Monomer N and Monomer P; wherein, B is a nucleobase or nucleobase analog.

In certain embodiments, the nucleic acid compound comprises one or more RNA nucleomonomers.

In certain embodiments, the nucleic acid compound comprises one or more DNA nucleomonomers.

In certain embodiments, the nucleic acid compound comprises RNA and DNA nucleomonomers.

In certain embodiments, the nucleic acid compound comprises one or more hydroxymethyl substituted nucleomonomers.

In certain embodiments, at least one double-stranded region is from about 5 base pairs up to 13 base pairs.

In certain embodiments, the double-stranded regions combined total from about 15 base pairs to about 40 base pairs.

In certain embodiments, the first strand is from about 10 to about 40 nucleomonomers in length, and the second and third strands are each, individually, from about 5 to about 20 nucleomonomers, wherein the combined length of the second and third strands is about 10 nucleomonomers to about 40 nucleomonomers.

In other embodiments, the nucleic acid compound is a RISC activator (e.g., the first strand has about 15 nucleotides to about 25 nucleotides) or a Dicer substrate (e.g., the first strand has about 26 nucleotides to about 40 nucleotides).

In some embodiments, the gap comprises at least one to ten unpaired nucleomonomers in the first strand positioned between the double-stranded regions formed by the second and third strands when annealed to the first strand.

In some embodiments, the double-stranded regions are separated by a nick.

In certain embodiments, the nick or gap is located 10 nucleomonomers from the 5'-end of the first (antisense) strand or at the Argonaute cleavage site.

In another embodiment, the nick or gap is positioned such that the thermal stability is maximized for the first and second strand duplex and for the first and third strand duplex as compared to the thermal stability of such meroduplexes having a nick or gap in a different position.

In one aspect of the disclosure, the number of hydroxymethyl substituted nucleomonomers in the antisense strand is 10. In other embodiments of the disclosure, the number of hydroxymethyl substituted nucleomonomer(s) in the antisense strand is 9, 8, 7, 6, 5, 4, 3, 2 or 1, respectively.

In another aspect, all nucleomonomers of the antisense strand are hydroxymethyl substituted nucleomonomers.

In one aspect of the disclosure, all hydroxymethyl substituted nucleomonomers in the antisense strand are present in positions 1, 2, 3, 4, 5, 6, 7, and/or 8, wherein the positions are counted from the 5' end of the antisense strand. Even more preferably, the hydroxymethyl substituted nucleomonomers in the antisense strand are present in positions 2, 3, 4, 5, 6, and/or 7, counted from the 5' end of the antisense strand or in the corresponding to the so-called seed region of a microRNA. In another aspect, the hydroxymethyl substituted nucleomonomers in the antisense strand are present in positions 4, 5, 6, 7 and/or 8, counted from the 5' end of the antisense strand. In another aspect, the hydroxymethyl substituted nucleomonomers in the antisense strand are present in positions 6, 7 and/or 8, counted from the 5' end of the antisense strand. In another aspect, the hydroxymethyl substituted nucleomonomers in the antisense strand are present in positions in the antisense strand that reduce the microRNA activity of the nucleic acid compound compared to the same nucleic acid compound without hydroxymethyl substituted nucleomonomers. Thus, presence of hydroxymethyl substituted nucleomonomers in the aforementioned regions may prevent the antisense strand from acting as a microRNA, which reduces off target effects when the antisense strand is intended to function as siRNA.

In a preferred embodiment, at least one hydroxymethyl substituted nucleomonomer is present in any one of positions 9, 10, 11, 12, 13, 14, 15, and/or 16, wherein the positions are counted from the 5'-end of the antisense strand. Even more preferred is hydroxymethyl substituted nucleomonomers present in any one of positions 9, 10, 11, 12, 13, 14, 15, and/or 16, wherein the positions are counted from the 5' end of the antisense strand. In another embodiment, hydroxymethyl substituted nucleomonomers in the antisense strand is present in all of positions 9, 10, 11, 12, 13, 14, 15, and/or 16. In one embodiment, hydroxymethyl substituted nucleomonomer are only present in regions 9, 10, 11, 12, 13, 14, 15, and/or 16 and not in the rest of the antisense strand.

Even more preferably, the hydroxymethyl substituted nucleomonomers in the antisense strand is present in position 9, 10, and/or 11, counted from the 5' end of the antisense strand, and preferably, not in the rest of the oligonucleotide. In another aspect, the hydroxymethyl substituted nucleomonomers in the antisense strand are present in positions in the antisense strand that enhance the microRNA activity of the nucleic acid compound compared to the same nucleic acid compound without hydroxymethyl substituted nucleomonomers. The presence of hydroxymethyl substituted nucleomonomers in the aforementioned regions may induce the antisense strand to act as a microRNA, i.e. ensure that the siRNA effect will be minimal and the microRNA effect much higher.

In another embodiment of the disclosure, the number of hydroxymethyl substituted nucleomonomers in the passenger strand of a nucleic acid compound of the disclosure is 10. In other embodiments of the disclosure, the number of hydroxymethyl substituted nucleomonomers in the passenger strand of a nucleic acid compound of the disclosure is 9, 8, 7, 6, 5, 4, 3, 2 or 1, respectively.

In another embodiment, all nucleomonomers of the passenger strand of a nucleic acid compound of the disclosure are hydroxymethyl substituted nucleomonomers.

In certain aspects, the sense (passenger strand) of a nucleic acid compound comprises one or more hydroxymethyl substituted nucleomonomer(s). In certain aspects, the sense (passenger strand) of a nucleic acid compound comprises 1, 2, 3, 4, 5, 6, 7, 8, 9 or 10 hydroxymethyl substituted nucleomonomer(s). In certain aspects, the entire sense (passenger strand) of a nucleic acid compound comprises hydroxymethyl substituted nucleomonomer(s).

In certain aspects, a hydroxymethyl substituted nucleomonomer in the sense strand is present in positions 1, 2, 3, 4, 5, 6, 7, and/or 8 wherein the positions are counted from the 5'-end of the sense strand. In certain aspects, a hydroxymethyl substituted nucleomonomer in the sense strand is present in positions 1, 2, 3, and/or 4 wherein the positions are counted from the 5'-end of the sense strand. In certain aspects, a hydroxymethyl substituted nucleomonomer in the sense strand is present in positions 1, 2 and/or 3 wherein the positions are counted from the 5'-end of the sense strand. In certain aspects, a hydroxymethyl substituted nucleomonomer in the sense strand is present in positions 5, 6, 7, and/or 8 wherein the positions are counted from the 5'-end of the sense strand. In certain aspects, a hydroxymethyl substituted nucleomonomer in the sense strand is present in positions 7 and/or 8 wherein the positions are counted from the 5'-end of the sense strand. In certain aspects, hydroxymethyl substituted nucleomonomers in the sense strand are present in positions in the sense strand of an nucleic acid compound that reduce the RNAi activity of the sense strand of the nucleic acid compound compared to the same nucleic acid compound without hydroxymethyl substituted nucleomonomers.

In certain aspects, a hydroxymethyl substituted nucleomonomer in the sense strand is present in positions 9, 10, 11, 12, 13, 14, 15, and/or 16 wherein the positions are counted from the 5'-end of the sense strand. In certain aspects, a hydroxymethyl substituted nucleomonomer in the sense strand is present in positions 9, 10, and/or 11, wherein the positions are counted from the 5'-end of the sense strand.

In certain aspects, a hydroxymethyl substituted nucleomonomer in the sense strand is present in positions 19, 20, 21, 22, 23, 24, 25, 26, 27, 28, 29, 30, 31 and/or 32 wherein the positions are counted from the 5'-end of the sense strand. In certain aspects, a hydroxymethyl substituted nucleomonomer in the sense strand is present in positions 1, 2, 3, 4, 5, 6, 7, 8, 9 and/or 10, wherein the positions are counted from the 3'-end of the sense strand.

In one embodiment, both the antisense strand and the passenger strand of a nucleic acid compound of the disclosure contain one or more hydroxymethyl substituted nucleomonomer(s).

In certain embodiments, one or both of the last two positions at the 3'-end of the sense strand are occupied by the same or different hydroxymethyl substituted nucleomonomer. In certain embodiments, one or both of the last two positions at the 3'-end of the antisense strand are occupied by the same or different hydroxymethyl substituted nucleomonomer. In certain embodiments, any one or more of the last three positions at the 5'-end of the sense strand is occupied by the same or different hydroxymethyl substituted nucleomonomer. In certain embodiments, at least one hydroxymethyl substituted nucleomonomer is in a double-stranded region of the nucleic acid compound.

In yet another embodiment, the core double stranded region of a nucleic acid compound of the disclosure is shorter than 10 base pairs and thus comprises from one to nine base pairs.

In one aspect, the present disclosure provides a nucleic acid compound capable of mediating nucleic acid modifications of a target nucleic acid. Such nucleic acid compound may, for example, be an siRNA, microRNA or microRNA precursor (pre-microRNA).

In any of the aspects of this disclosure, some embodiments provide a nucleic acid comprising one or more 5-methyluridine (ribothymidine), a 2-thioribothymidine, or 2'-O-methyl-5-methyluridine, deoxyuridine, locked nucleic acid (LNA) molecule, or a universal-binding nucleotide, or a G clamp. Exemplary universal-binding nucleotides include C-phenyl, C-naphthyl, inosine, azole carboxamide, 1-β-D-ribofuranosyl-4-nitroindole, 1-β-D-ribofuranosyl-5-nitroindole, 1-β-D-ribofuranosyl-6-nitroindole, or 1-β-D-ribofuranosyl-3-nitropyrrole. In some embodiments, the nucleic acid further comprises a 2'-sugar substitution, such as a 2'-O-methyl, 2'-O-methoxyethyl, 2'-O-2-methoxyethyl, 2'-O-allyl, or halogen (e.g., 2'-fluoro).

In certain embodiments, the nucleic acid further comprises a terminal cap substituent on one or both ends of one or more of the first strand, second strand, or third strand, such as independently an alkyl, abasic, deoxy abasic, glyceryl, dinucleotide, acyclic nucleotide, or inverted deoxynucleotide moiety. In other embodiments, the nucleic acid further comprises at least one modified internucleoside linkage, such as independently a phosphorothioate, chiral phosphorothioate, phosphorodithioate, phosphotriester, aminoalkylphosphotriester, methyl phosphonate, alkyl phosphonate, 3'-alkylene phosphonate, 5'-alkylene phosphonate, chiral phosphonate, phosphonoacetate, thiophosphonoacetate, phosphinate, phosphoramidate, 3'-amino phosphoramidate, aminoalkylphosphoramidate, thionophosphoramidate, thionoalkylphosphonate, thionoalkylphosphotriester, selenophosphate, or boranophosphate linkage.

In any of the aspects disclosed herein, the nucleic acid compound comprises a 2'-O-methyl nucleomonomer. In a related aspect, the nucleic acid compound comprises from zero to twelve 2'-O-methyl nucleomonomer(s) (or 0, 1, 2, 3, 4, 5, 6, 7, 8, 9, 10, 11 or 12 2'-O-methyl nucleomonomer(s)).

In a related aspect, the passenger strand of the nucleic acid compound comprises from zero to twelve 2'-O-methyl nucleomonomer(s) (or 0, 1, 2, 3, 4, 5, 6, 7, 8, 9, 10, 11 or 12 2'-O-methyl nucleomonomer(s)). In a related aspect, the guide strand of the nucleic acid compound comprises from zero to six 2'-O-methyl nucleomonomer(s) (or 0, 1, 2, 3, 4, 5 or 6 2'-O-methyl nucleomonomer(s)). In certain aspects, the hydroxymethyl substituted monomer is a 2'-O-methyl nucleomonomer.

In any of the aspects of this disclosure, some embodiments provide nucleic acid compound comprising an overhang of one to five (or 1, 2, 3, 4, 5) nucleomonomers on at least one 3'-end that is not part of the gap. In any of the aspects of this disclosure, some embodiments provide a nucleic acid compound has a blunt end at one or both ends. In other embodiments, the 5'-terminal of the sense strand, antisense strand or both strands is a hydroxyl or a phosphate.

In one embodiment, the nucleic acid compound may be a bifunctional nucleic acid compound having two blunt-ends and a hydroxymethyl substituted nucleomonomer at position(s) 5, 6, 7, and/or 8 from the 5'-end of each of the guide strand and passenger strand, and wherein nucleic acid compound comprises one or more conformationally restricted nucleomonomers.

In one embodiment, the bifunctional nucleic acid compound comprise two blunt-ends, a sense strand and a anti-sense strand, wherein the sense strand comprises an hydroxymethyl substituted nucleomonomer at position(s) 5, 6, 7, and/or 8 from the 5'-end of the sense strand, and the antisense strand comprises an hydroxymethyl substituted nucleomonomer at position(s) 5, 6, 7, and/or 8 from the 5'-end of antisense strand, and wherein the sense strand is complementary to a first region of a target nucleic acid and the antisense region is complementary to a second region of the target nucleic acid, wherein the first region and the second region are non-overlapping regions of the target nucleic acid. In a related embodiment, the first and second regions of the target nucleic acid partially overlap.

In one embodiment, the bifunctional nucleic acid compound comprise two blunt-ends, a sense strand and a anti-sense strand, wherein the sense strand comprises an hydroxymethyl substituted nucleomonomer at position(s) 5, 6, 7, and/or 8 from the 5'-end of the sense strand, and the antisense strand comprises an hydroxymethyl substituted nucleomonomer at position(s) 5, 6, 7, and/or 8 from the 5'-end of antisense strand, and wherein the sense strand is complementary to a first region of a first target nucleic acid and the antisense region is complementary to a second region of a second target nucleic acid, wherein the first target nucleic acid and the second target nucleic acid are different target nucleic acid molecules, or have less than 95% homology, or 90% homology, or 85% homology, or 80% homology, or 75% homology, or 70% homology, or 65% homology, or 60% homology, or 55% homology or 50% homology. In a related embodiment, the first and second target nucleic acid molecules are in the same cellular pathway.

In one aspect, the present disclosure provides a nucleic acid compound comprising a first strand and a second strand complementary to the first strand, wherein the first strand and the second strand can anneal to form a double-stranded region, and wherein the double-stranded region comprises one or more mismatches, and wherein one or more of the nucleomonomers of the first strand or the second strand is a conformationally restricted nucleomonomer In certain embodiments, the first strand has from 10 to 60 (or 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60) nucleomonomers.

In certain embodiments, the double-stranded region comprises from 8 to 60 (or 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60) base pairs.

In certain embodiments, the double-stranded region comprises two mismatches. In certain embodiments, the double-stranded region comprises three mismatches. In certain embodiments, the double-stranded region comprises four mismatches. In certain embodiments, the double-stranded region comprises five mismatches. In certain embodiments, the double-stranded region comprises six mismatches. In certain embodiments, the double-stranded region comprises seven mismatches. In certain embodiments, the double-stranded region comprises eight mismatches.

In certain embodiments, the first and second strands are joined by a non-pairing region of nucleomonomers.

In certain embodiments, the nucleic compound comprises a short hairpin structure.

In certain embodiments, the nucleic compound is a short hairpin RNA (shRNA).

In certain embodiments, the conformationally restricted nucleomonomer reduces or eliminates the microRNA acidity of the nucleic acid compound.

In one aspect, the instant disclosure provides a nucleic acid compound comprising a strand having from 10 to 100 (or 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleomonomers, two or more double-strand regions, wherein the double-stranded regions are separated by mismatches, wherein the nucleic acid compound comprises a hairpin turn, and wherein one or more of the nucleomonomers is a conformationally restricted nucleomonomer.

In one aspect, the instant disclosure provides a nucleic acid compound comprising a strand having from 10 to 100 (or 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleomonomers, a double-strand region, a hairpin turn, and wherein one or more of the nucleomonomers is a conformationally restricted nucleomonomer.

In certain embodiments, the double-stranded region comprises one mismatch. In certain embodiments, the double-stranded region comprises two mismatches. In certain embodiments, the double-stranded region comprises three mismatches. In certain embodiments, the double-stranded region comprises four mismatches. In certain embodiments, the double-stranded region comprises five mismatches. In certain embodiments, the double-stranded region comprises six mismatches. In certain embodiments, the double-stranded region comprises seven mismatches. In certain embodiments, the double-stranded region comprises eight mismatches.

In certain embodiments, the conformationally restricted nucleomonomer reduces or eliminates the microRNA activity of the nucleic acid compound.

In certain embodiments, the conformationally restricted nucleomonomer is located in the seed region of the nucleic acid compound.

In certain embodiments, the melting temperature of the nucleic acid compound is from 40° C. to 100° C., or from 60° C. to 90° C., or from 75° C. to 80° C.

In certain embodiments, from 1% to 75% of the nucleomonomers of the first strand of the nucleic acid compound are conformationally restricted nucleomonomers, or from 20% to 60% of the nucleomonomers of the first strand of the nucleic acid compound are conformationally restricted nucleomonomers, or from 40% to 50% of the nucleomonomers of the first strand of the nucleic acid compound are conformationally restricted nucleomonomers.

In certain embodiments, the nucleic acid compound comprises RNA. In certain embodiments, the nucleic acid compound comprises DNA. In certain embodiments, the nucleic acid compound comprises RNA and DNA.

In other embodiments, the first strand is from 10 to 40 (or 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40) nucleomonomers in length. In other embodiments, the first strand is from 10 to 30 nucleomonomers in length.

In certain embodiments, the conformationally restricted nucleomonomer is Monomer R and has the following formula:

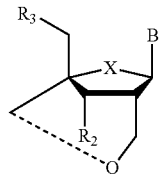

where X is independently for each occurrence selected from O, S, $CH_2$, C=O, C=S, C=$CH_2$, CHF or $CF_2$; $R_2$ and $R_3$ are independently for each occurrence selected from hydrogen, OH, O-alkyl, F, SH, S-alkyl, S—F, CN, $N_3$, $OCH_3$, monosphosphate, diphosphate, triphosphate, monophosphate, diphosphonate, triphosphonate, an amino acid ester with an OH group the sugar portion, or a prodrug of the monophosphate, diphosphate, triphosphate, monophosphonate, diphosphonate, or triphosphonate, NH(CH=O), NH(C=O)—C(1-22) saturated or unsaturated alkyl chain, cycloalkyl, aryl or heterocyclic; and B is independently for each occurrence a nucleobase or nucleobase analog.

In certain embodiments, the conformationally restricted nucleomonomer is Monomer Q and has the following formula:

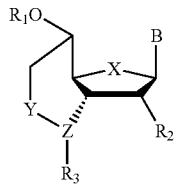

where X and Y are independently for each occurrence selected from O, S, $CH_2$, C=O, C=S, C=$CH_2$, CHF, $CF_2$; Z is independently for each occurrence selected from N or CH;

$R_2$ is independently for each occurrence selected from hydrogen, F, OH, or OMe; $R_1$ and $R_3$ are independently for each occurrence selected from hydrogen, OH, P(OR)$_2$, P(O)(OR)$_2$, P(S)(OR)$_2$, P(O)(SR)OR, acyl, carbobenzoxy, trifluoroacetyl, p-nitrophenyloxycarbonyl, or any suitable protecting group or an activating group for building oligomers; and R is independently for each occurrence selected from H, 2-cyanoethyl, diisopropylamino, alkyl, alkenyl, alkynyl, or a hydrophobic masking group, where R can be same or different from each other in case of (OR)$_2$, or (SR)OR.

In certain embodiments, the nucleic acid compound comprises one or more Monomer R and one or more Monomer Q.

In certain embodiments, the nucleic acid compound further comprises a second strand.

In certain embodiments, the second strand comprises one or more conformationally restricted nucleomonomers.

In certain embodiments, the nucleic acid compound further comprises a hydroxymethyl substituted nucleomonomer. In certain embodiments, the hydroxymethyl substituted nucleomonomer is independently for each occurrence selected from Monomer A, Monomer C, Monomer E, Monomer G, Monomer I, Monomer K, Monomer M, and Monomer O; wherein, X is independently for each occurrence selected from O, S, or —CH$_2$; Z is independently for each occurrence selected from hydrogen, OH, CH$_2$OH, CH$_3$ or saturated or unsaturated C(2-22) alkyl chain; J is independently for each occurrence selected from P or S; $R_2$ is independently for each occurrence selected from hydrogen, OH, O-alkyl, F, SH, S-alkyl, SF, NH(CH=O), NH(C=O)—C(1-22) saturated or unsaturated alkyl chain, cycloalkyl, aryl or heterocyclic; and B is a nucleobase or nucleobase analog.

In certain embodiments, the hydroxymethyl substituted nucleomonomer is independently for each occurrence selected from Monomer B, Monomer D, Monomer F, Monomer H, Monomer J, Monomer L, Monomer N and Monomer P; wherein, B is a nucleobase or nucleobase analog.

In certain embodiments, the first strand is from 10 to 40 nucleomonomers in length or from 10 to 30 nucleomonomers in length Synthesis of Nucleic Acid Molecules Exemplary molecules of the instant disclosure are recombinantly produced, chemically synthesized, or a combination thereof. Oligonucleotides (e.g., certain modified oligonucleotides or portions of oligonucleotides lacking ribonucleotides) are synthesized using protocols known in the art, for example as described in Caruthers et al., *Methods in Enzymol.* 211:3-19, 1992; Thompson et al., PCT Publication No. WO 99/54459, Wincott et al., *Nucleic Acids Res.* 23:2677-2684, 1995; Wincott et al., *Methods Mol. Bio.* 74:59, 1997; Brennan et al., *Biotechnol Bioeng.* 61:33-45, 1998; and Brennan, U.S. Pat. No. 6,001,311. Synthesis of RNA, including certain dsRNA molecules and analogs thereof of this disclosure, can be made using the procedure as described in Usman et al., *J. Am. Chem. Soc.* 109:7845, 1987; Scaringe et al., *Nucleic Acids Res.* 18:5433, 1990; and Wincott et al., *Nucleic Acids Res.* 23:2677-2684, 1995; Wincott et al., *Methods Mol. Bio.* 74:59, 1997.

In certain embodiments, the nucleic acid molecules of the present disclosure can be synthesized separately and joined together post-synthetically, for example, by ligation (Moore et al., *Science* 256:9923, 1992; Draper et al., PCT Publication No. WO 93/23569; Shabarova et al., *Nucleic Acids Res.* 19:4247, 1991; Bellon et al., *Nucleosides & Nucleotides* 16:951, 1997; Bellon et al., *Bioconjugate Chem.* 8:204, 1997), or by hybridization following synthesis or deprotection.

In certain embodiments, double-stranded portions of dsRNAs, in which two or more strands pair up, are not limited to completely paired nucleotide segments, and may contain non-pairing portions due to a mismatch (the corresponding nucleotides are not complementary), bulge (lacking in the corresponding complementary nucleotide on one strand), overhang, or the like. Non-pairing portions can be contained to the extent that they do not interfere with dsRNA formation and function. In certain embodiments, a "bulge" may comprise 1 to 2 non-pairing nucleotides, and the double-stranded region of dsRNAs in which two strands pair up may contain from about 1 to 7, or about 1 to 5 bulges. In addition, "mismatch" portions contained in the double-stranded region of dsRNAs may include from about 1 to 7, or about 1 to 5 mismatches. In other embodiments, the double-stranded region of dsRNAs of this disclosure may contain both bulge and mismatched portions in the approximate numerical ranges specified herein.

A dsRNA or analog thereof of this disclosure may be further comprised of a nucleotide, non-nucleotide, or mixed nucleotide/non-nucleotide linker that joins the sense region of the dsRNA to the antisense region of the dsRNA. In one embodiment, a nucleotide linker can be a linker of more than about 2 nucleotides length up to about 10 nucleotides in length. In another embodiment, the nucleotide linker can be a nucleic acid aptamer.

A non-nucleotide linker may be comprised of an abasic nucleotide, polyether, polyamine, polyamide, peptide, carbohydrate, lipid, polyhydrocarbon, or other polymeric compounds (e.g., polyethylene glycols such as those having between 2 and 100 ethylene glycol units). Specific examples include those described by Seela and Kaiser, *Nucleic Acids Res.* 18:6353, 1990, and *Nucleic Acids Res.* 15:3113, 1987; Cload and Schepartz, *J. Am. Chem. Soc.* 113:6324, 1991; Richardson and Schepartz, *J. Am. Chem. Soc.* 113:5109, 1991; Ma et al., *Nucleic Acids Res.* 21:2585, 1993, and *Biochemistry* 32:1751, 1993; Durand et al., *Nucleic Acids Res.* 18:6353, 1990; McCurdy et al., *Nucleosides & Nucleotides* 10:287, 1991; Jaschke et al., *Tetrahedron Lett.* 34:301, 1993; Ono et al., *Biochemistry* 30:9914, 1991; Arnold et al., PCT Publication No. WO 89/02439; Usman et al., PCT Publication No. WO 95/06731; Dudycz et al., PCT Publication No. WO 95/11910 and Ferentz and Verdine, *J. Am. Chem. Soc.* 113:4000, 1991. The synthesis of a dsRNA molecule of this disclosure, which can be further modified, comprises: (a) synthesis of a first (antisense) strand and synthesis of a second (sense) strand and a third (sense) strand that are each complementary to non-overlapping regions of the first strand; and (b) annealing the first, second and third strands together under conditions suitable to obtain a dsRNA molecule. In another embodiment, synthesis of the first, second and third strands of a dsRNA molecule is by solid phase oligonucleotide synthesis. In yet another embodiment, synthesis of the first, second, and third strands of a dsRNA molecule is by solid phase tandem oligonucleotide synthesis.

Chemically synthesizing nucleic acid molecules with substitutions or modifications (base, sugar, phosphate, or any combination thereof) can prevent their degradation by serum ribonucleases, which may lead to increased potency. See, e.g., Eckstein et al., PCT Publication No. WO 92/07065; Perrault et al., *Nature* 344:565, 1990; Pieken et al., *Science* 253:314, 1991; Usman and Cedergren, Trends in *Biochem. Sci.* 17:334, 1992; Usman et al., *Nucleic Acids Symp. Ser.*

31:163, 1994; Beigelman et al., *J. Biol. Chem.* 270:25702, 1995; Burgin et al., *Biochemistry* 35:14090, 1996; Burlina et al., *Bioorg. Med. Chem.* 5:1999, 1997; Thompson et al., Karpeisky et al., *Tetrahedron Lett.* 39:1131, 1998; Earnshaw and Gait, *Biopolymers (Nucleic Acid Sciences)* 48:39-55, 1998; Verma and Eckstein, *Annu. Rev. Biochem.* 67:99-134, 1998; Herdewijn, *Antisense Nucleic Acid Drug Dev.* 10:297, 2000; Kurreck, *Eur. J. Biochem.* 270:1628, 2003; Dorsett and Tuschl, *Nature Rev. Drug Discov.* 3:318, 2004; PCT Publication Nos. WO 91/03162; WO 93/15187; WO 97/26270; WO 98/13526; U.S. Pat. Nos. 5,334,711; 5,627,053; 5,716,824; 5,767,264; 6,300,074. Each of the above references discloses various substitutions and chemical modifications to the base, phosphate, or sugar moieties of nucleic acid molecules, which can be used in the dsRNAs described herein. For example, oligonucleotides can be modified at the sugar moiety to enhance stability or prolong biological activity by increasing nuclease resistance. Representative sugar modifications include 2'-amino, 2'-C-allyl, 2'-fluoro, 2'-O-methyl, 2'-O-allyl, or 2'-H. Other modifications to enhance stability or prolong biological activity can be internucleoside linkages, such as phosphorothioate, or base-modifications, such as locked nucleic acids (see, e.g., U.S. Pat. Nos. 6,670,461; 6,794,499; 6,268,490), or 5-methyluridine or 2'-O-methyl-5-methyluridine in place of uridine (see, e.g., U.S. Patent Application Publication No. 2006/0142230). Hence, dsRNA molecules of the instant disclosure can be modified to increase nuclease resistance or duplex stability while substantially retaining or having enhanced RNAi activity as compared to unmodified dsRNA.

In one embodiment, this disclosure features substituted or modified dsRNA molecules, such as phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, or alkylsilyl substitutions. For a review of oligonucleotide backbone modifications, see Hunziker and Leumann, *Nucleic Acid Analogues: Synthesis and Properties, in Modern Synthetic Methods, VCH,* 331-417, 1995; and Mesmaeker et al., *ACS,* 24-39, 1994.

In another embodiment, a conjugate molecule can be optionally attached to a dsRNA or analog thereof that decreases expression of a target gene by RNAi. For example, such conjugate molecules may be polyethylene glycol, human serum albumin, polyarginine, Gln-Asn polymer, or a ligand for a cellular receptor that can, for example, mediate cellular uptake (e.g., HIV TAT, see Vocero-Akbani et al., *Nature Med.* 5:23, 1999; see also U.S. Patent Application Publication No. 2004/0132161). Examples of specific conjugate molecules contemplated by the instant disclosure that can be attached to a dsRNA or analog thereof of this disclosure are described in Vargeese et al., U.S. Patent Application Publication No. 2003/0130186, and U.S. Patent Application Publication No. 2004/0110296.

In another embodiment, a conjugate molecule is covalently attached to a nucleic acid compound (e.g., dsRNA) or analog thereof that decreases expression of a target gene by RNAi via a biodegradable linker. In certain embodiments, a conjugate molecule can be attached at the 3'-end of either the sense strand, the antisense strand, or both strands of a dsRNA molecule provided herein. In another embodiment, a conjugate molecule can be attached at the 5'-end of either the sense strand, the antisense strand, or both strands of the dsRNA or analog thereof. In yet another embodiment, a conjugate molecule is attached at both the 3'-end and 5'-end of either the sense strand, the antisense strand, or both strands of a dsRNA molecule, or any combination thereof. In further embodiments, a conjugate molecule of this disclosure comprises a molecule that facilitates delivery of a dsRNA or analog thereof into a biological system, such as a cell. A person of skill in the art can screen dsRNA of this disclosure having various conjugates to determine whether the dsRNA-conjugate possesses improved properties (e.g., pharmacokinetic profiles, bioavailability, stability) while maintaining the ability to mediate RNAi in, for example, an animal model as described herein or generally known in the art.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated.

As used herein, "about" or "consisting essentially of" mean±20% of the indicated range, value, or structure, unless otherwise indicated.

As used herein, the terms "include" and "comprise" are open ended and are used synonymously.

It should be understood that the terms "a" and "an" as used herein refer to "one or more" of the enumerated components.

The use of the alternative (e.g., "or") should be understood to mean either one, both, or any combination thereof of the alternatives.

As used herein, the term "linked" encompasses a covalent linkage either directly between two chemical entities (e.g., RNA and a hydroxymethyl substituted nucleomonomer), or indirectly between two chemical entities, for example via a linker.

As used herein, the term "overhang" (e.g., 3'-end overhang or 3' overhang) means an unpaired region of a nucleic acid compound which may contain all nucleotides, non-nucleotides (e.g., hydroxymethyl substituted nucleomonomers), or a combination of nucleotides and non-nucleotides.

As used herein, the term "nucleobase analog" refers to a substituted or unsubstituted nitrogen-containing parent heteroaromatic ring that is capable of forming Watson-Crick hydrogen bonds with a complementary nucleobase or nucleobase analog. Exemplary nucleobase analogs include, but are not limited to, 7-deazaadenine, inosine, nebularine, nitropyrrole, nitroindole, 2-aminopurine, 2,6-diaminopurine, hypoxanthine, pseudouridine, 5-propynylcytidine, isocytidine, isoguanine, 7-deazaguanine, 2-thiopyrimidine, 6-thioguanine, 4-thiothymine, 4-thiouracil, $O^6$-methyl guanine, $N^6$-methyl adenine, $O^4$-methyl thymine, 5,6-dihydrothymine, 5,6-dihydrouracil, 4-methylindole, ethenoadenine. Additional exemplary nucleobase analogs can be found in Fasman, 1989, Practical Handbook of Biochemistry and Molecular Biology, pp. 385-394, CRC Press, Boca Raton, Fla., and the references cited therein, incorporated herein by reference.

As used herein, the term "nucleomonomer" means a moiety comprising (1) a base covalently linked to (2) a second moiety. Nucleomonomers can be linked to form oligomers that bind to target or complementary base sequences in nucleic acids in a sequence specific manner. Nucleomonomers may be nucleosides, nucleotides, non-nucleotides or non-nucleosides (e.g. hydroxymethyl substituted nucleomonomer).

As used herein, the terms "hydroxymethyl substituted nucleomonomer", "hydroxymethyl nucleomonomer", "hydroxymethyl monomer", "acyclic nucleomonomer", "acyclic monomer", "acyclic hydroxymethyl substituted nucleomonomer" may be used interchangeably throughout.

As used herein, the terms "conformationally restricted nucleomonomer", "conformationally restricted nucleotide" may be used interchangeably and refer to a nucleomonomer that has a bicyclic sugar moiety (e.g. bicyclic ribose) wherein the C2' and C4' of the sugar moiety are bridged (e.g., Monomer R) or the C3' and C5' are bridged (e.g., Monomer Q). Additional examples may be found in U.S. Pat. No. 6,833,361; U.S. Pat. No. 6,403,566 and U.S. Pat. No. 6,083,482, which are hereby incorporated by reference in their entirety.

As used herein, the terms "RISC length" or "RISC length RNA complex" means a nucleic acid molecule having less than 25 base pairs.

As used herein the terms "Dicer length" or "Dicer length RNA complex" means a nucleic acid molecule have 25 or more base pairs, generally, from 25 to 40 base pairs.

As used herein the term "bifunctional nucleic acid compound" or "bifunctional RNA complex" or "bifunctional dsRNA" means a nucleic acid compound having a sense strand and antisense strand, wherein the sense strand and the antisense strand are each complementary to different regions of the same target RNA (i.e., a first region and a second region), or are each complementary to a region of at least two different target RNAs.

As used herein, the terms "seed region" or "seed sequence" refer to the region of a microRNA that is implicated in gene regulation by inhibition of translation and/or mRNA degradation, or the portion of the guide strand in a siRNA that is analogous to the seed region of a microRNA As used herein, the term "isolated" means that the referenced material (e.g., nucleic acid molecules of the instant disclosure), is removed from its original environment, such as being separated from some or all of the co-existing materials in a natural environment (e.g., a natural environment may be a cell).

As used herein, "complementary" refers to a nucleic acid molecule that can form hydrogen bond(s) with another nucleic acid molecule or itself by either traditional Watson-Crick base pairing or other non-traditional types of pairing (e.g., Hoogsteen or reversed Hoogsteen hydrogen bonding) between complementary nucleosides or nucleotides. In reference to the nucleic molecules of the present disclosure, the binding free energy for a nucleic acid molecule with its complementary sequence is sufficient to allow the relevant function of the nucleic acid molecule to proceed, for example, RNAi activity, and there is a sufficient degree of complementarity to avoid non-specific binding of the nucleic acid molecule (e.g., dsRNA) to non-target sequences under conditions in which specific binding is desired, i.e., under physiological conditions in the case of in vivo assays or therapeutic treatment, or under conditions in which the assays are performed in the case of in vitro assays (e.g., hybridization assays). Determination of binding free energies for nucleic acid molecules is well known in the art (see, e.g., Turner et al., *CSH Symp. Quant. Biol. LII*:123, 1987; Frier et al., *Proc. Nat'l. Acad. Sci. USA* 83:9373, 1986; Turner et al., *J. Am. Chem. Soc.* 109:3783, 1987). Thus, "complementary" or "specifically hybridizable" or "specifically binds" are terms that indicate a sufficient degree of complementarity or precise pairing such that stable and specific binding occurs between a nucleic acid molecule (e.g., dsRNA) and a DNA or RNA target. It is understood in the art that a nucleic acid molecule need not be 100% complementary to a target nucleic acid sequence to be specifically hybridizable or to specifically bind. That is, two or more nucleic acid molecules may be less than fully complementary and is indicated by a percentage of contiguous residues in a nucleic acid molecule that can form hydrogen bonds with a second nucleic acid molecule.

For example, a first nucleic acid molecule may have 10 nucleotides and a second nucleic acid molecule may have 10 nucleotides, then base pairing of 5, 6, 7, 8, 9, or 10 nucleotides between the first and second nucleic acid molecules, which may or may not form a contiguous double-stranded region, represents 50%, 60%, 70%, 80%, 90%, and 100% complementarity, respectively. In certain embodiments, complementary nucleic acid molecules may have wrongly paired bases—that is, bases that cannot form a traditional Watson-Crick base pair or other non-traditional types of pair (i.e., "mismatched" bases). For instance, complementary nucleic acid molecules may be identified as having a certain number of "mismatches," such as zero or about 1, about 2, about 3, about 4 or about 5.

"Perfectly" or "fully" complementary nucleic acid molecules means those in which a certain number of nucleotides of a first nucleic acid molecule hydrogen bond (anneal) with the same number of residues in a second nucleic acid molecule to form a contiguous double-stranded region. For example, two or more fully complementary nucleic acid molecule strands can have the same number of nucleotides (i.e., have the same length and form one double-stranded region, with or without an overhang) or have a different number of nucleotides (e.g., one strand may be shorter than but fully contained within another strand or one strand may overhang the other strand).

By "ribonucleic acid" or "RNA" is meant a nucleic acid molecule comprising at least one ribonucleotide molecule. As used herein, "ribonucleotide" refers to a nucleotide with a hydroxyl group at the 2'-position of a β-D-ribofuranose moiety. The term RNA includes double-stranded (ds) RNA, single-stranded (ss) RNA, isolated RNA (such as partially purified RNA, essentially pure RNA, synthetic RNA, recombinantly produced RNA), altered RNA (which differs from naturally occurring RNA by the addition, deletion, substitution or alteration of one or more nucleotides), or any combination thereof. For example, such altered RNA can include addition of non-nucleotide material, such as at one or both ends of an RNA molecule, internally at one or more nucleotides of the RNA, or any combination thereof. Nucleotides in RNA molecules of the instant disclosure can also comprise non-standard nucleotides, such as naturally occurring nucleotides, non-naturally occurring nucleotides, chemically-modified nucleotides, deoxynucleotides, or any combination thereof. These altered RNAs may be referred to as analogs or analogs of RNA containing standard nucleotides (i.e., standard nucleotides, as used herein, are considered to be adenine, cytidine, guanidine, thymidine, and uridine).

The term "dsRNA" and "RNA complex" as used herein, refers to any nucleic acid molecule comprising at least one ribonucleotide molecule and capable of inhibiting or down regulating gene expression, for example, by promoting RNA interference ("RNAi") or gene silencing in a sequence-specific manner. The dsRNAs (mdRNAs) of the instant disclosure may be suitable substrates for Dicer or for association with RISC to mediate gene silencing by RNAi. Examples of dsRNA molecules of this disclosure are provided in the Sequence Listing identified herein. One or both strands of the dsRNA can further comprise a terminal phosphate group, such as a 5'-phosphate or 5',3'-diphosphate. As used herein, dsRNA molecules, in addition to at least one ribonucleotide, can further include substitutions, chemically-modified nucleotides, and non-nucleotides. In certain embodiments, dsRNA molecules comprise ribonucleotides up to about 100% of the nucleotide positions.

The nucleic acid compounds disclosed herein may comprise two strands that together constitute an RNA duplex composed of an antisense strand (the antisense strand is also herein referred to as the guide strand or first strand) and a passenger strand (the passenger strand is also herein referred to as the sense strand or second strand), a single stranded RNA molecule (e.g. antisense RNA), a functional RNA (fRNA), or non-coding RNA (ncRNA), such as small temporal RNA (stRNA), microRNA (miRNA), small nuclear RNA (snRNA), short interfering RNA (siRNA), small nucleolar RNA (snRNA), ribosomal RNA (rRNA), transfer RNA (tRNA) and precursor RNAs thereof, an RNAa molecule, a microRNA mimicking molecule is also considered herein as an RNA complex of the disclosure, as is a single stranded antisense molecule that for example is useful for targeting microRNAs.

In addition, as used herein, the term dsRNA is meant to be equivalent to other terms used to describe nucleic acid molecules that are capable of mediating sequence specific RNAi, for example, meroduplex RNA (mdRNA), nicked dsRNA (ndsRNA), gapped dsRNA (gdsRNA), short interfering nucleic acid (siNA), siRNA, micro-RNA (miRNA), short hairpin RNA (shRNA), short interfering oligonucleotide, short interfering substituted oligonucleotide, short interfering modified oligonucleotide, chemically-modified dsRNA, post-transcriptional gene silencing RNA (ptgsRNA), or the like.

In some respects, dsRNA molecules described herein form a meroduplex RNA (mdRNA) having three or more strands, for example, an 'A' (first or antisense) strand, 'S1' (second) strand, and 'S2' (third) strand in which the 'S1' and 'S2' strands are complementary to and form base pairs (bp) with non-overlapping regions of the 'A' strand (e.g., an mdRNA can have the form of A:S1S2). The 51, S2, or more strands together essentially comprise a sense strand to the 'A' strand. The double-stranded region formed by the annealing of the 'S1' and 'A' strands is distinct from and non-overlapping with the double-stranded region formed by the annealing of the 'S2' and 'A' strands. An mdRNA molecule is a "gapped" molecule, meaning a "gap" ranging from 0 nucleotides up to about 10 nucleotides. In some embodiments, the A:S1 duplex is separated from the A:S2 duplex by a gap resulting from at least one unpaired nucleotide (up to about 10 unpaired nucleotides) in the 'A' strand that is positioned between the A:S1 duplex and the A:S2 duplex and that is distinct from any one or more unpaired nucleotide at the 3'-end of one or more of the 'A', 'S1', or 'S2' strands. In some embodiments, the A:S1 duplex is separated from the A:B2 duplex by a gap of zero nucleotides (i.e., a nick in which only a phosphodiester bond between two nucleotides is broken or missing in the polynucleotide molecule) between the A:S1 duplex and the A:S2 duplex—which can also be referred to as nicked dsRNA (ndsRNA). For example, A:S1S2 may be comprised of a dsRNA having at least two double-stranded regions that combined total about 14 base pairs to about 40 base pairs and the double-stranded regions are separated by a gap of about 0 to about 10 nucleotides, optionally having blunt ends, or A:S1S2 may comprise a dsRNA having at least two double-stranded regions separated by a gap of up to 10 nucleotides wherein at least one of the double-stranded regions comprises between about 5 base pairs and 13 base pairs.

The term "large double-stranded RNA" ("large dsRNA") refers to any double-stranded RNA longer than about 40 base pairs (bp) to about 100 bp or more, particularly up to about 300 bp to about 500 bp. The sequence of a large dsRNA may represent a segment of an mRNA or an entire mRNA. A double-stranded structure may be formed by a self-complementary nucleic acid molecule or by annealing of two or more distinct complementary nucleic acid molecule strands.

In addition, as used herein, the term "RNAi" is meant to be equivalent to other terms used to describe sequence specific RNA interference, such as post transcriptional gene silencing, translational inhibition, or epigenetics. For example, dsRNA molecules of this disclosure can be used to epigenetically silence genes at the post-transcriptional level or the pre-transcriptional level or any combination thereof.

As used herein, the term "nucleic acid based regulatory system" or "cell regulatory system dependent upon a nucleic acid" refers to any cell regulatory system that is regulated, modified, controlled, or modulated, in full or part, by the presence and/or function of a nucleomonomer, nucleotide, nucleoside, and/or oligonucleotide.

As used herein, "target nucleic acid" refers to any nucleic acid sequence whose expression or activity is to be altered. The target nucleic acid can be DNA, RNA, or analogs thereof, and includes single, double, and multi-stranded forms.

By "target site" or "target sequence" is meant a sequence within a target nucleic acid (e.g., mRNA) that, when present in an RNA molecule, is "targeted" for cleavage by RNAi and mediated by a dsRNA construct of this disclosure containing a sequence within the antisense strand that is complementary to the target site or sequence.

As used herein, "off-target effect" or "off-target profile" refers to the observed altered expression pattern of one or more genes in a cell or other biological sample not targeted, directly or indirectly, for gene silencing by an mdRNA or dsRNA. For example, an off-target effect can be quantified by using a DNA microarray to determine how many non-target genes have an expression level altered by about two-fold or more in the presence of a candidate mdRNA or dsRNA, or analog thereof specific for a target sequence. A "minimal off-target effect" means that an mdRNA or dsRNA affects expression by about two-fold or more of about 25% to about 1% of the non-target genes examined or it means that the off-target effect of substituted or modified mdRNA or dsRNA (e.g., having at least one uridine substituted with a 5-methyluridine or 2-thioribothymidine and optionally having at least one nucleotide modified at the 2'-position), is reduced by at least about 1% to about 80% or more as compared to the effect on non-target genes of an unsubstituted or unmodified mdRNA or dsRNA.

By "sense region" or "sense strand" or "second strand" is meant one or more nucleotide sequences of a nucleic acid compound having complementarity to one or more antisense regions of the nucleic acid compound. In addition, the sense region of a nucleic acid compound comprises a nucleic acid sequence having homology or identity to a target sequence.

By "antisense region" or "antisense strand" or "first strand" is meant a nucleotide sequence of a dsRNA molecule having complementarity to a target nucleic acid sequence. In addition, the antisense region of a dsRNA molecule can comprise nucleic acid sequence region having complementarity to one or more sense strands of the dsRNA molecule.

"Analog" as used herein refers to a compound that is structurally similar to a parent compound (e.g., a nucleic acid molecule), but differs slightly in composition (e.g., one atom or functional group is different, added, or removed). The analog may or may not have different chemical or physical properties than the original compound and may or may not have improved biological or chemical activity. For example, the analog may be more hydrophilic or it may have altered activity as compared to a parent compound. The analog may mimic the chemical or biological activity of the parent compound (i.e., it may have similar or identical activity), or, in some cases, may have increased or decreased activity. The analog may be a naturally or non-naturally occurring (e.g., chemically-modified or recombinant) variant of the original compound. An example of an RNA analog is an RNA molecule having a non-standard nucleotide, such as 5-methyuridine or 5-methylcytidine or 2-thioribothymidine, which may impart certain desirable properties (e.g., improve stability, bioavailability, minimize off-target effects or interferon response).

As used herein, the term "universal base" refers to nucleotide base analogs that form base pairs with each of the standard DNA/RNA bases with little discrimination between them. A universal base is thus interchangeable with all of the standard bases when substituted into a nucleotide duplex (see, e.g., Loakes et al., *J. Mol. Bio.* 270:426, 1997). Exemplary universal bases include C-phenyl, C-naphthyl and other aromatic derivatives, inosine, azole carboxamides, or nitroazole derivatives such as 3-nitropyrrole, 4-nitroindole, 5-nitroindole, and 6-nitroindole (see, e.g., Loakes, *Nucleic Acids Res.* 29:2437, 2001).

The term "gene" as used herein, especially in the context of "target gene" or "gene target" for RNAi, means a nucleic acid molecule that encodes an RNA or a transcription product of such gene, including a messenger RNA (mRNA, also referred to as structural genes that encode for a polypeptide), an mRNA splice variant of such gene, a functional RNA (fRNA), or non-coding RNA (ncRNA), such as small temporal RNA (stRNA), microRNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for dsRNA mediated RNAi to alter the activity of the target RNA involved in functional or regulatory cellular processes.

As used herein, "gene silencing" refers to a partial or complete loss-of-function through targeted inhibition of gene expression in a cell, which may also be referred to as RNAi "knockdown," "inhibition," "down-regulation," or "reduction" of expression of a target gene. Depending on the circumstances and the biological problem to be addressed, it may be preferable to partially reduce gene expression. Alternatively, it might be desirable to reduce gene expression as much as possible. The extent of silencing may be determined by methods described herein and known in the art (see, e.g., PCT Publication No. WO 99/32619; Elbashir et al., *EMBO J.* 20:6877, 2001). Depending on the assay, quantification of gene expression permits detection of various amounts of inhibition that may be desired in certain embodiments of this disclosure, including prophylactic and therapeutic methods, which will be capable of knocking down target gene expression, in terms of mRNA level or protein level or activity, for example, by equal to or greater than 10%, 30%, 50%, 75% 90%, 95% or 99% of baseline (i.e., normal) or other control levels, including elevated expression levels as may be associated with particular disease states or other conditions targeted for therapy.

As used herein, the term "therapeutically effective amount" means an amount of dsRNA that is sufficient to result in a decrease in severity of disease symptoms, an increase in frequency or duration of disease symptom-free periods, or a prevention of impairment or disability due to the disease, in the subject (e.g., human) to which it is administered. For example, a therapeutically effective amount of dsRNA directed against an mRNA of a target gene can inhibit the deposition of lipoproteins in the walls of arteries by at least about 20%, at least about 40%, at least about 60%, or at least about 80% relative to untreated subjects. A therapeutically effective amount of a therapeutic compound can decrease, for example, atheromatous plaque size or otherwise ameliorate symptoms in a subject. One of ordinary skill in the art would be able to determine such therapeutically effective amounts based on such factors as the subject's size, the severity of symptoms, and the particular composition or route of administration selected. The nucleic acid molecules of the instant disclosure, individually, or in combination or in conjunction with other drugs, can be used to treat diseases or conditions discussed herein. For example, to treat a particular disease, disorder, or condition, the dsRNA molecules can be administered to a patient or can be administered to other appropriate cells evident to those skilled in the art, individually or in combination with one or more drugs, under conditions suitable for treatment.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure. As described herein, all value ranges are inclusive over the indicated range. Thus, a range of $C_1$-$C_4$ will be understood to include the values of 1, 2, 3, and 4, such that $C_1$, $C_2$, $C_3$ and $C_4$ are included.

The term "alkyl" as used herein refers to a saturated, branched or unbranched, substituted or unsubstituted aliphatic group containing from 1-22 carbon atoms (1, 2, 3, 4, 5, 6, 7, 8, 9, 10, 11, 12, 13, 14, 15, 16, 17, 18, 19, 20, 21, or 22 carbon atoms). This definition applies to the alkyl portion of other groups such as, for example, alkoxy, alkanoyl, aralkyl, and other groups defined below. The term "cycloalkyl" as used herein refers to a saturated, substituted or unsubstituted cyclic alkyl ring containing from 3 to 12 carbon atoms.

The term "alkenyl" as used herein refers to an unsaturated, branched or unbranched, substituted or unsubstituted alkyl or cycloalkyl having 2 to 22 carbon atoms and at least one carbon-carbon double bond. The term "alkynyl" as used herein refers to an unsaturated, branched or unbranched, substituted or unsubstituted alkyl or cycloalkyl having 2 to 22 carbon atoms and at least one carbon-carbon triple bond.

The term "alkoxy" as used herein refers to an alkyl, cycloalkyl, alkenyl, or alkynyl group covalently bonded to an oxygen atom. The term "alkanoyl" as used herein refers to —C(═O)-alkyl, which may alternatively be referred to as "acyl." The term "alkanoyloxy" as used herein refers to —O—C(═O)-alkyl groups. The term "alkylamino" as used herein refers to the group —NRR', where R and R' are each either hydrogen or alkyl, and at least one of R and R' is alkyl. Alkylamino includes groups such as piperidino wherein R and R' form a ring. The term "alkylaminoalkyl" refers to -alkyl-NRR'.

The term "aryl" as used herein refers to any stable monocyclic, bicyclic, or polycyclic carbon ring system of from 4 to 12 atoms in each ring, wherein at least one ring is aromatic. Some examples of an aryl include phenyl, naphthyl, tetrahydro-naphthyl, indanyl, and biphenyl. Where an aryl substituent is bicyclic and one ring is non-aromatic, it is understood that attachment is to the aromatic ring. An aryl may be substituted or unsubstituted.

The term "heteroaryl" as used herein refers to any stable monocyclic, bicyclic, or polycyclic carbon ring system of from 4 to 12 atoms in each ring, wherein at least one ring is aromatic and contains from 1 to 4 heteroatoms selected from oxygen, nitrogen and sulfur. Some examples of a heteroaryl include acridinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, and tetrahydroquinolinyl. A heteroaryl includes the N-oxide derivative of a nitrogen-containing heteroaryl.

The term "heterocycle" or "heterocyclyl" as used herein refers to an aromatic or nonaromatic ring system of from five to twenty-two atoms, wherein from 1 to 4 of the ring atoms are heteroatoms selected from oxygen, nitrogen, and sulfur. Thus, a heterocycle may be a heteroaryl or a dihydro or tetrathydro version thereof.

The term "aroyl" as used herein refers to an aryl radical derived from an aromatic carboxylic acid, such as a substituted benzoic acid. The term "aralkyl" as used herein refers to an aryl group bonded to an alkyl group, for example, a benzyl group.

The term "carboxyl" as used herein represents a group of the formula —C(=O)OH or —C(=O)O$^-$. The terms "carbonyl" and "acyl" as used herein refer to a group in which an oxygen atom is double-bonded to a carbon atom >C=O. The term "hydroxyl" as used herein refers to —OH or —O$^-$. The term "nitrile" or "cyano" as used herein refers to —CN. The term "halogen" or "halo" refers to fluoro (—F), chloro (—Cl), bromo (—Br), and iodo (—I).

The term "cycloalkyl" as used herein refers to a saturated cyclic hydrocarbon ring system containing from 3 to 12 carbon atoms that may be optionally substituted. Exemplary embodiments include, but are not limited to, cyclopropyl, cyclobutyl, cyclopentyl and cyclohexyl. In certain embodiments, the cycloalkyl group is cyclopropyl. In another embodiment, the (cycloalkyl)alkyl groups contain from 3 to 12 carbon atoms in the cyclic portion and 1 to 6 carbon atoms in the alkyl portion. In certain embodiments, the (cycloalkyl)alkyl group is cyclopropylmethyl. The alkyl groups are optionally substituted with from one to three substituents selected from the group consisting of halogen, hydroxy and amino.

The terms "alkanoyl" and "alkanoyloxy" as used herein refer, respectively, to —C(O)-alkyl groups and —O—C(=O)— alkyl groups, each optionally containing 2 to 10 carbon atoms. Specific embodiments of alkanoyl and alkanoyloxy groups are acetyl and acetoxy, respectively.

The term "alkynyl" as used herein refers to an unsaturated branched, straight-chain, or cyclic alkyl group having 2 to 10 carbon atoms and having at least one carbon-carbon triple bond derived by the removal of one hydrogen atom from a single carbon atom of a parent alkyne. Exemplary alkynyls include ethynyl, 1-propynyl, 2-propynyl, 1-butynyl, 2-butynyl, 3-butynyl, 1-pentynyl, 2-pentynyl, 4-pentynyl, 1-octynyl, 6-methyl-1-heptynyl, 2-decynyl, or the like. The alkynyl group may be substituted or unsubstituted.

The term "hydroxyalkyl" alone or in combination, refers to an alkyl group as previously defined, wherein one or several hydrogen atoms, preferably one hydrogen atom has been replaced by a hydroxyl group. Examples include hydroxymethyl, hydroxyethyl and 2-hydroxyethyl.

The term "aminoalkyl" as used herein refers to the group —NRR', where R and R' may independently be hydrogen or ($C_1$-$C_4$) alkyl.

The term "alkylaminoalkyl" refers to an alkylamino group linked via an alkyl group (i.e., a group having the general structure -alkyl-NH-alkyl or -alkyl-N(alkyl)(alkyl)). Such groups include, but are not limited to, mono- and di-($C_1$-$C_8$ alkyl)amino$C_1$-$C_8$ alkyl, in which each alkyl may be the same or different.

The term "dialkylaminoalkyl" refers to alkylamino groups attached to an alkyl group. Examples include, but are not limited to, N,N-dimethylaminomethyl, N,N-dimethylaminoethyl N,N-dimethylaminopropyl, and the like. The term dialkylaminoalkyl also includes groups where the bridging alkyl moiety is optionally substituted.

The term "haloalkyl" refers to an alkyl group substituted with one or more halo groups, for example chloromethyl, 2-bromoethyl, 3-iodopropyl, trifluoromethyl, perfluoropropyl, 8-chlorononyl, or the like.

The term "carboxyalkyl" as used herein refers to the substituent —$R^{10}$—COOH, wherein $R^{10}$ is alkylene; and "carbalkoxyalkyl" refers to —$R^{10}$—C(=O)O$R^{11}$, wherein $R^{10}$ and $R^{11}$ are alkylene and alkyl respectively. In certain embodiments, alkyl refers to a saturated straight- or branched-chain hydrocarbyl radical of 1 to 6 carbon atoms such as methyl, ethyl, n-propyl, isopropyl, n-butyl, t-butyl, n-pentyl, 2-methylpentyl, n-hexyl, and so forth. Alkylene is the same as alkyl except that the group is divalent.

The term "alkoxy" includes substituted and unsubstituted alkyl, alkenyl, and alkynyl groups covalently linked to an oxygen atom. In one embodiment, the alkoxy group contains 1 to about 10 carbon atoms. Embodiments of alkoxy groups include, but are not limited to, methoxy, ethoxy, isopropyloxy, propoxy, butoxy, and pentoxy groups. Embodiments of substituted alkoxy groups include halogenated alkoxy groups. In a further embodiment, the alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Exemplary halogen substituted alkoxy groups include, but are not limited to, fluoromethoxy, difluoromethoxy, trifluoromethoxy, chloromethoxy, dichloromethoxy, and trichloromethoxy.

The term "alkoxyalkyl" refers to an alkylene group substituted with an alkoxy group. For example, methoxyethyl ($CH_3OCH_2CH_2$—) and ethoxymethyl ($CH_3CH_2OCH_2$—) are both $C_3$ alkoxyalkyl groups.

The term "aroyl," as used alone or in combination herein, refers to an aryl radical derived from an aromatic carboxylic acid, such as optionally substituted benzoic or naphthoic acids.

The term "aralkyl" as used herein refers to an aryl group bonded to the 2-pyridinyl ring or the 4-pyridinyl ring through an alkyl group, preferably one containing 1 to 10 carbon atoms. A preferred aralkyl group is benzyl.

The term "carboxy," as used herein, represents a group of the formula —C(=O)OH or —C(=O)O$^-$.

The term "carbonyl" as used herein refers to a group in which an oxygen atom is double-bonded to a carbon atom —C=O.

The term "trifluoromethyl" as used herein refers to —CF$_3$.

The term "trifluoromethoxy" as used herein refers to —OCF$_3$.

The term "hydroxyl" as used herein refers to —OH or -O$^-$.

The term "nitrile" or "cyano" as used herein refers to the group —CN.

The term "nitro," as used herein alone or in combination refers to a —NO$_2$ group.

The term "amino" as used herein refers to the group —NR$^9$R$^9$, wherein R$^9$ may independently be hydrogen, alkyl, aryl, alkoxy, or heteroaryl. The term "aminoalkyl" as used herein represents a more detailed selection as compared to "amino" and refers to the group —NR'R', wherein R' may independently be hydrogen or (C$_1$-C$_4$) alkyl. The term "dialkylamino" refers to an amino group having two attached alkyl groups that can be the same or different.

The term "alkanoylamino" refers to alkyl, alkenyl or alkynyl groups containing the group —C(=O)— followed by —N(H)—, for example acetylamino, propanoylamino and butanoylamino and the like.

The term "carbonylamino" refers to the group —NR'—CO—CH$_2$—R', wherein R' may be independently selected from hydrogen or (C$_1$-C$_4$) alkyl.

The term "carbamoyl" as used herein refers to —O—C(O)NH$_2$.

The term "carbamyl" as used herein refers to a functional group in which a nitrogen atom is directly bonded to a carbonyl, i.e., as in —NR"C(=O)R" or —C(=O)NR"R", wherein R" can be independently hydrogen, alkyl, substituted alkyl, alkenyl, substituted alkenyl, alkoxy, cycloalkyl, aryl, heterocyclo, or heteroaryl.

The term "alkylsulfonylamino" refers to the group —NHS(O)$_2$R$^{12}$, wherein R$^{12}$ is alkyl.

The term "halogen" as used herein refers to bromine, chlorine, fluorine or iodine. In one embodiment, the halogen is fluorine. In another embodiment, the halogen is chlorine.

The term "heterocyclo" refers to an optionally substituted, unsaturated, partially saturated, or fully saturated, aromatic or nonaromatic cyclic group that is a 4 to 7 membered monocyclic, or 7 to 11 membered bicyclic ring system that has at least one heteroatom in at least one carbon atom-containing ring. The substituents on the heterocyclo rings may be selected from those given above for the aryl groups. Each ring of the heterocyclo group containing a heteroatom may have 1, 2, or 3 heteroatoms selected from nitrogen, oxygen or sulfur. Plural heteroatoms in a given heterocyclo ring may be the same or different.

Exemplary monocyclic heterocyclo groups include pyrrolidinyl, pyrrolyl, indolyl, pyrazolyl, imidazolyl, oxazolyl, isoxazolyl, thiazolyl, furyl, tetrahydrofuryl, thienyl, piperidinyl, piperazinyl, azepinyl, pyrimidinyl, pyridazinyl, tetrahydropyranyl, morpholinyl, dioxanyl, triazinyl and triazolyl. Preferred bicyclic heterocyclo groups include benzothiazolyl, benzoxazolyl, benzothienyl, quinolinyl, tetrahydroisoquinolinyl, benzimidazolyl, benzofuryl, indazolyl, benzisothiazolyl, isoindolinyl and tetrahydroquinolinyl. In more detailed embodiments heterocyclo groups may include indolyl, imidazolyl, furyl, thienyl, thiazolyl, pyrrolidyl, pyridyl and pyrimidyl.

The "percent identity" between two or more nucleic acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., BLASTN, see Altschul et al., *J. Mol. Biol.* 215:403-410, 1990).

"Aptamer" or "nucleic acid aptamer" as used herein is meant a nucleic acid molecule that binds specifically to a target molecule wherein the nucleic acid molecule has sequence that comprises a sequence recognized by the target molecule in its natural setting. Alternately, an aptamer can be a nucleic acid molecule that binds to a target molecule wherein the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art (see, e.g., Gold et al., *Annu. Rev. Biochem.* 64:763, 1995; Brody and Gold, *J. Biotechnol.* 74:5, 2000; Sun, *Curr. Opin. Mol. Ther.* 2:100, 2000; Kusser, *J. Biotechnol.* 74:27, 2000; Hermann and Patel, *Science* 287:820, 2000; and Jayasena, *Clinical Chem.* 45:1628, 1999).

The term "substituted" as used herein refers to an atom having one or more substitutions or substituents which can be the same or different and may include a hydrogen substituent. Thus, the terms alkyl, cycloalkyl, alkenyl, alkynyl, alkoxy, alkanoyl, alkanoyloxy, alkylamino, alkylaminoalkyl, aryl, heteroaryl, heterocycle, aroyl, and aralkyl as used herein refer to groups which include substituted variations. Substituted variations include linear, branched, and cyclic variations, and groups having a substituent or substituents replacing one or more hydrogens attached to any carbon atom of the group. Substituents that may be attached to a carbon atom of the group include alkyl, cycloalkyl, alkenyl, alkynyl, alkoxy, alkanoyl, alkanoyloxy, alkylamino, alkylaminoalkyl, aryl, heteroaryl, heterocycle, aroyl, aralkyl, acyl, hydroxyl, cyano, halo, haloalkyl, amino, aminoacyl, alkylaminoacyl, acyloxy, aryloxy, aryloxyalkyl, mercapto, nitro, carbamyl, carbamoyl, and heterocycle. For example, the term ethyl includes without limitation —CH$_2$CH$_3$, —CHFCH$_3$, —CF$_2$CH$_3$, —CHFCH$_2$F, —CHFCHF$_2$, —CHFCF$_3$, —CF$_2$CH$_2$F, —CF$_2$CHF$_2$, —CF$_2$CF$_3$, and other variations as described above. Representative substituents include —X, —R$^6$, —O—, =O, —OR, —SR$^6$, —S—, =S, —NR$^6$R$^6$, =NR$^6$, —CX$_3$, —CF$_3$, —CN, —OCN, —SCN, —NO, —NO$_2$, =N$_2$, —N$_3$, —S(=O)$_2$O—, —S(=O)$_2$OH, —S(=O)$_2$R$^6$, —OS(=O)$_2$O—, —OS(=O)$_2$OH, —OS(=O)$_2$R$^6$, —P(=O)(O$^-$)$_2$, —P(=O)(OH)(O$^-$), —OP(=O)$_2$(O), —C(=O)R$^6$, —C(=S)R$^6$, —C(=O)OR$^6$, —C(=O)O$^-$, —C(=S)OR$^6$, —NR$^6$—C(=O)—N(R$^6$)$_2$, —NR$^6$—C(=S)—N(R$^6$)$_2$, and —C(=NR$^6$)NR$^6$R$^6$, wherein each X is independently a halogen; and each R$^6$ is independently hydrogen, halogen, alkyl, aryl, arylalkyl, arylaryl, arylheteroalkyl, heteroaryl, heteroarylalkyl, NR$^7$R$^7$, —C(=O)R$^7$, and —S(=O)$_2$R$^7$; and each R$^7$ is independently hydrogen, alkyl, alkanyl, alkynyl, aryl, arylalkyl, arylheteralkyl, arylaryl, heteroaryl or heteroarylalkyl. Aryl containing substituents, whether or not having one or more substitutions, may be attached in a para (p-), meta (m-) or ortho (o-) conformation, or any combination thereof. In general, substituents may be further substituted with any atom or group of atoms.

For example purposes only, the position of a nucleomonomer in a strand may be described as follows where X represents any type of nucleomonomer (e.g., nucleoside, modified nucleotide, RNA, DNA, hydroxymethyl substituted nucleomonomer or conformationally restricted nucleomonomer) and the number represents the position of that nucleomonomer in the strand. For example, X1 represents position one of the strand below counting from the 5'-end of the strand; X7 represents position seven of the strand below counting from the 5'-end of the strand. Alternatively, X1, X2, and X3 represent the last three positions at the 5'-end of the strand below, and X1 to X10 represent the last ten positions at the 5'-end of the strand. The $X_n$ may represent positions 11 to 60 (or n=1 to 60), thus when n is 20 (or X20), this indicates position 20 of the strand counting from the 5'-end of the strand.

5' X1-X2-X3-X4-X5-X6-X7-X8-X9-X10-$X_n$ 3'

The same approach may be taken by counting from the 3'-end of a strand in order to identify the position of a nucleomonomer in the strand (example strand shown below). For the strand below, the position of a nucleomonomer in the strand may be described as follows where X represents any type of nucleomonomer (e.g., nucleoside, modified nucleotide, RNA, DNA, hydroxymethyl substituted nucleomonomer or conformationally restricted nucleomonomer) and the number represents the position of that nucleomonomer in the strand. For example, X1 represents position one of the strand below counting from the 3'-end of the strand; X7 represents position seven of the strand below counting from the 3'-end of the strand. Alternatively, X1, X2, and X3 represent the last three positions at the 3'-end of the strand below, and X1 to X10 represent the last ten positions at the 3'-end of the strand. The $X_n$ may represent positions 11 to 60 (or n=1 to 60), thus when n is 20 (or X20), this indicates position 20 of the strand counting from the 3'-end of the strand.

5' $X_n$-X10-X9-X8-X7-X6-X5-X4-X3-X2-X1 3'

All publications, non-patent publications, references, patents, patent publications, patent applications and other literature cited herein are each hereby specifically incorporated by reference in entirety.

While this disclosure has been described in relation to certain embodiments, and many details have been set forth for purposes of illustration, it will be apparent to those skilled in the art that this disclosure includes additional embodiments, and that some of the details described herein may be varied considerably without departing from this disclosure. This disclosure includes such additional embodiments, modifications and equivalents. In particular, this disclosure includes any combination of the features, terms, or elements of the various illustrative components and examples.

The use herein of the terms "a," "an," "the" and similar terms in describing the disclosure, and in the claims, are to be construed to include both the singular and the plural.

The terms "comprising," "having," "including" and "containing" are to be construed as open-ended terms which mean, for example, "including, but not limited to." Thus, terms such as "comprising," "having," "including" and "containing" are to be construed as being inclusive, not exclusive.

Recitation of a range of values herein refers individually to each and any separate value falling within the range as if it were individually recited herein, whether or not some of the values within the range are expressly recited. For example, the range "4 to 12" includes without limitation the values 5, 5.1, 5.35 and any other whole, integer, fractional, or rational value greater than or equal to 4 and less than or equal to 12. Specific values employed herein will be understood as exemplary and not to limit the scope of the disclosure.

Recitation of a range of number of carbon atoms herein refers individually to each and any separate value falling within the range as if it were individually recited herein, whether or not some of the values within the range are expressly recited. For example, the term "C1-24" includes without limitation the species C1, C2, C3, C4, C5, C6, C7, C8, C9, C10, C11, C12, C13, C14, C15, C16, C17, C18, C19, C20, C21, C22, C23, and C24.

Definitions of technical terms provided herein should be construed to include without recitation those meanings associated with these terms known to those skilled in the art, and are not intended to limit the scope of the disclosure. Definitions of technical terms provided herein shall be construed to dominate over alternative definitions in the art or definitions, which become incorporated herein by reference to the extent that the alternative definitions conflict with the definition provided herein.

The examples given herein, and the exemplary language used herein are solely for the purpose of illustration, and are not intended to limit the scope of the disclosure.

When a list of examples is given, such as a list of compounds or molecules suitable for this disclosure, it will be apparent to those skilled in the art that mixtures of the listed compounds or molecules are also suitable.

EXAMPLES

Example 1

RNA Targeting Survivin (BIRC5)

Sequence specific RNAs targeting Survivin (BIRC5) are shown in Tables 1 and 2. CRN monomers in the sequences of Tables 1 and 2 are identified as "crnX" where X is the one letter code for the nucleotide: A, U, C or G. For example, "crnC" indicates a cytidine CRN. The CRN in Tables 1 and 2 is based on Monomer R, Monomer Q, or a combination of Monomers R and Q. Each one of sense sequences SEQ ID NOs:1-80 will complex with one of the antisense sequences SEQ ID NOs:81-160, respectively, in other words, SEQ ID NO:1 will complex with SEQ ID NO:81, SEQ ID NO:2 will complex with SEQ ID NO:82, and so forth.

TABLE 1

RNA Targeting Survivin

| SEQ ID NO: | Sense Sequence (5' to 3' left to right) |
|---|---|
| 1 | CUGCCUGGCAGCCCUUUCcrnU |
| 2 | CcrnUGCCUGGCAGCCCUUUCUUcrnU |
| 3 | crnUcrnCUGCCUGGCAGCCCUUUCUUcrnU |
| 4 | CcrnUcrnGCCUGGCAGCCCUUUCUUcrnU |

TABLE 1-continued

RNA Targeting Survivin

| SEQ ID NO: | Sense Sequence (5' to 3' left to right) |
|---|---|
| 5 | CUGCCUGGCAGCCCUUUCcrnUUU |
| 6 | CcrnUGCCUGGCAGCCCUUUCcrnUUU |
| 7 | crnCcrnUGCCUGGCAGCCCUUUCcrnUUU |
| 8 | UcrnCcrnUGCCUGGCAGCCCUUUCcrnUUU |
| 9 | GACCACCGCAUCUCUAcrnCAcrnU |
| 10 | GcrnACCACCGCAUCUCUACAcrnUUcrnU |
| 11 | crnUcrnGACCACCGCAUCUCUACAcrnUUcrnU |
| 12 | GcrnAcrnCCACCGCAUCUCUACAcrnUUcrnU |
| 13 | GACCACCGCAUCUCUACAcrnUcrnUcrnU |
| 14 | GcrnACCACCGCAUCUCUACAcrnUcrnUcrnU |
| 15 | crnGcrnACCACCGCAUCUCUACAcrnUcrnUcrnU |
| 16 | UcrnGcrnACCACCGCAUCUCUACAcrnUcrnUcrnU |
| 17 | CGCAUCUCUACAUUCAAGA |
| 18 | CGCAUCUCUACAUUCAAGAUU |
| 19 | UCGCAUCUCUACAUUCAAGAUU |
| 20 | CGCAUCUCUACAUUCAAGAUU |
| 21 | CGCAUCUCUACAUUCAAGAUU |
| 22 | CGCAUCUCUACAUUCAAGAUU |
| 23 | CGCAUCUCUACAUUCAAGAUU |
| 24 | UCGCAUCUCUACAUUCAAGAUU |
| 25 | GCCCAGUGUUUCUUCUGCU |
| 26 | GCCCAGUGUUUCUUCUGCUUU |
| 27 | UGCCCAGUGUUUCUUCUGCUUU |
| 28 | GCCCAGUGUUUCUUCUGCUUU |
| 29 | GCCCAGUGUUUCUUCUGCUUU |
| 30 | GCCCAGUGUUUCUUCUGCUUU |
| 31 | GCCCAGUGUUUCUUCUGCUUU |
| 32 | UGCCCAGUGUUUCUUCUGCUUU |
| 33 | CcrnCCcrnAGcrnUGcrnUUcrnUCcrnUUcrnUCcrnGCcrnUU |
| 34 | CCcrnCAGcrnUGcrnUUcrnUUCcrnUUCcrnUGCcrnUUUcrnU |
| 35 | UCCcrnCAGUcrnGUUUcrnCUUCcrnUGCUcrnUUU |
| 36 | CCCAcrnGUGUUcrnUCUUCcrnUGCUUCcrnUU |
| 37 | CCCAGcrnUGUUUCcrnUUCUGCcrnUUUU |
| 38 | CCCAGUcrnGUUUCUUcrnUCUGCUUUcrnU |
| 39 | CCCAGUGcrnUUUCUUCUcrnGCUUUU |
| 40 | UCCCAGUGcrnUUUCUUCUGcrnCUUUU |
| 41 | CCAGUGUUUCrnCUUCUGCUUC |
| 42 | CCAGUGUUUCrnCcrnUUCUGCUUCUU |
| 43 | UCCAGUGUUCrnUCUcrnUCUGCUUCUU |
| 44 | CCAGUGCrnUCrnUCrnUCUUCUGCUUCUU |
| 45 | CCAGUGUCrnUCrnUCUUCUGCUUCUU |
| 46 | CCAGUGUUCrnUCrnUCUUCUGCUUCUU |
| 47 | CCAGUGUCrnUUCrnUCUUCUGCUUCUU |
| 48 | UCCAGUGUCrnUUCcrnUUCUGCUUCUU |
| 49 | CAGUGUUUCUUCUGCUcrnUCA |
| 50 | CcrnAGUGUUUCUUCUGCUUCAUcrnU |
| 51 | crnUcrnCAGUGUUUCUUCUGCUUCcrnAUcrnU |
| 52 | CcrnAcrnGUGUUUCUUCUGCUUCcrnAcrnUcrnU |
| 53 | crnCAGUGUUUCUUCUGCUUCAUU |
| 54 | CAcrnGUGUUUCUUCUGCUUCAcrnUU |
| 55 | crnCAcrnGUGUUUCUUCUGCUUCcrnAcrnUU |
| 56 | crnUcrnCcrnAGUGUUUCUUCUGCUUCAcrnUcrnU |
| 57 | AGUGUUUCcrnUcrnUCUGCUUCAA |
| 58 | AGUGUUUCcrnUcrnUCUGCUUCAUU |
| 59 | UAGUGUUUCcrnUcrnUCUGCUUCAAUU |
| 60 | AGUGUUUcrnCUcrnUCrnUCcrnUGCUUCAAUU |
| 61 | AGUGUUUCcrnUUCcrnUGCUUCAAUU |
| 62 | AGUGUUUCUcrnUCUGcrnCUUCAAUU |
| 63 | AGUGUUUCUUcrnCUGcrnCUUcrnCAAUU |
| 64 | UAGUGUUUcrnCUUcrnCUGcrnCUUCAAUU |
| 65 | GAAGAcrnAAGAAUUUcrnGAGGAA |
| 66 | GAAGAAAGAAUUUGAGGAAUU |
| 67 | UGcrnAAGAAAGAAUUUGAGGcrnAAUU |
| 68 | GAcrnAGAAcrnAGAAUUUGAGGAAUcrnU |
| 69 | GAAGcrnAAAGAAUUcrnUGAGGAAUcrnU |
| 70 | GAAGAAAGAAUUUGAGGAAcrnUcrnU |
| 71 | crnGcrnAcrnAcrnGcrnAAAGAAUUUGAGGAAUU |
| 72 | UGAAcrnGAAAcrnGAAUUUGAGGAAUU |
| 73 | AGUGGCcrnACCAGcrnAGGUGCUcrnU |
| 74 | crnAGUGGCACCAGAGGUGCUUUcrnU |
| 75 | crnUAGUGGCACCAGAGGUGCUcrnUUcrnU |
| 76 | AGUGGCACCAGAGGUGCUUcrnUcrnU |
| 77 | crnAGUGGcrnCACCAGAGGUGCUUUU |
| 78 | AGUGGCACCAGAGGUGCcrnUUUU |

TABLE 1-continued

RNA Targeting Survivin

| SEQ ID NO: | Sense Sequence (5' to 3' left to right) |
|---|---|
| 79 | AGUGGCACCAGAGGUGCUUcrnUU |
| 80 | UAGUGGCACCAGAGGUGCUUUcrnU |

TABLE 2

RNA Targeting Survivin

| SEQ ID NO: | Antisense Sequence (5' to 3') |
|---|---|
| 81 | AGAAAGGGCUGCCAGGCAG |
| 82 | AGAAAGGGCUGCCAGGCAGUU |
| 83 | AGAAAGGGCUGCCAGGCAGUU |
| 84 | AGAAAGGGCUGCCAGGCAGUU |
| 85 | AGAAAGGGCUGCCAGGCAGUU |
| 86 | AGAAAGGGCUGCCAGGCAGUU |
| 87 | AGAAAGGGCUGCCAGGCAGUU |
| 88 | AGAAAGGGCUGCCAGGCAGUU |
| 89 | AUGUAGAGAUGCGGUGGUC |
| 90 | AUGUAGAGAUGCGGUGGUCUU |
| 91 | AUGUAGAGAUGCGGUGGUCUU |
| 92 | AUGUAGAGAUGCGGUGGUCUU |
| 93 | AUGUAGAGAUGCGGUGGUCUU |
| 94 | AUGUAGAGAUGCGGUGGUCUU |
| 95 | AUGUAGAGAUGCGGUGGUCUU |
| 96 | AUGUAGAGAUGCGGUGGUCUU |
| 97 | crnUCUUGAAUGUAGAGAUGCG |
| 98 | UCCrnUUGAAUGUAGAGAUGCGUU |
| 99 | crnUCcrnUUGAAUGUAGAGAUGCGUU |
| 100 | crnUcrnCcrnUUGAAUGUAGAGAUGCGUU |
| 101 | crnUCUUGAAUGUAGAGAUGCGcrnUU |
| 102 | UCCrnUUGAAUGUAGAGAUGCGcrnUU |
| 103 | crnUCcrnUUGAAUGUAGAGAUGCGcrnUU |
| 104 | crnUcrnCcrnUUGAAUGUAGAGAUGCGcrnUU |
| 105 | crnAGCAGAAGAAACACUGcrnGcrnGC |
| 106 | AGcrnCAGAAGAAACACUGGGcrnCcrnUU |
| 107 | crnAGcrnCAGAAGAAACACUGGGcrnCcrnUU |
| 108 | crnAcrnGcrnCAGAAGAAACACUGGGcrnCcrnUU |
| 109 | crnAGCAGAAGAAACACUGGGGcrnUcrnU |
| 110 | AGcrnCAGAAGAAACACUGGGCcrnUcrnU |

TABLE 2-continued

RNA Targeting Survivin

| SEQ ID NO: | Antisense Sequence (5' to 3') |
|---|---|
| 111 | crnAGcrnCAGAAGAAACACUGGGCcrnUcrnU |
| 112 | crnAcrnGcrnCAGAAGAAACACUGGGCcrnUcrnU |
| 113 | AAGCAGAAGAAACACUGGG |
| 114 | AAGCAGAAGAAACACUGGGUU |
| 115 | AAGCAGAAGAAACACUGGGUU |
| 116 | AAGCAGAAGAAACACUGGGUU |
| 117 | AAGCAGAAGAAACACUGGGUU |
| 118 | AAGCAGAAGAAACACUGGGUU |
| 119 | AAGCAGAAGAAACACUGGGUU |
| 120 | AAGCAGAAGAAACACUGGGUU |
| 121 | GAAGCAGAAGAAACACUGG |
| 122 | GAAGCAGAAGAAACACUGGUU |
| 123 | GAAGCAGAAGAAACACUGGUU |
| 124 | GAAGCAGAAGAAACACUGGUU |
| 125 | GAAGCAGAAGAAACACUGGUU |
| 126 | GAAGCAGAAGAAACACUGGUU |
| 127 | GAAGCAGAAGAAACACUGGUU |
| 128 | GAAGCAGAAGAAACACUGGUU |
| 129 | UGAAGCAGAAGAAACAcrnCUG |
| 130 | UcrnGAAGCAGAAGAAACACUGUcrnU |
| 131 | crnUcrnGAAGCAGAAGAAACACUcrnGUcrnU |
| 132 | UcrnGcrnAAGCAGAAGAAACACUcrnGcrnUcrnU |
| 133 | crnUGAAGCAGAAGAAACACUGUU |
| 134 | UGcrnAAGCAGAAGAAACACUGcrnUU |
| 135 | crnUGcrnAAGCAGAAGAAACACUcrnGcrnUU |
| 136 | crnUcrnGcrnAAGCAGAAGAAACACUGcrnUcrnU |
| 137 | UUGAAGCcrnAcrnGcrnAAGAAACACU |
| 138 | UUGAAGCAcrnGcrnAcrnAGAAACACUUU |
| 139 | UUGAAGCAcrnGcrnAAGAAACACUUU |
| 140 | UUGAAGCcrnAGcrnAAcrnGAAACACUUU |
| 141 | UUGAAGCAcrnGAAcrnGAAcrnACACUUU |
| 142 | UUGAAGCcrnAGAAcrnGAAACACUUU |
| 143 | UUGAAGCAcrnGAAcrnGAAcrnACACUUU |
| 144 | UUGAAGCAGcrnAAGAAACACUUU |
| 145 | UUCCUCAAAUUCUUUCUUC |
| 146 | UUCCUCAAAUUCUUUCUUCUU |
| 147 | UUCCUCAAAUUCUUUCUUCUU |

TABLE 2-continued

RNA Targeting Survivin

| SEQ ID NO: | Antisense Sequence (5' to 3') |
|---|---|
| 148 | UUCCUCAAAUUCUUUCUUCUU |
| 149 | UUCCUCAAAUUCUUUCUUCUU |
| 150 | UUCCUCAAAUUCUUUCUUCUU |
| 151 | UUCCUCAAAUUCUUUCUUCUU |
| 152 | UUCCUCAAAUUCUUUCUUCUU |
| 153 | AAGCACCUCUGGUGCCACU |
| 154 | AAGCACCUCUGGUGCCACUUU |
| 155 | AAGCACCUCUGGUGCCACUUU |
| 156 | AAGCACCUCUGGUGCCACUUU |
| 157 | AAGCACCUCUGGUGCCACUUU |
| 158 | AAGCACCUCUGGUGCCACUUU |
| 159 | AAGCACCUCUGGUGCCACUUU |
| 160 | AAGCACCUCUGGUGCCACUUU |

Example 2

RNA Targeting PLK

Sequence specific RNAs targeting PLK1 are shown in Tables 3 and 4. CRN monomers in the sequences of Tables 3 and 4 are identified as "crnX" where X is the one letter code for the nucleobase: A, U, C or G. For example, "crnC" indicates a cytosine CRN. The CRN in Tables 3 and 4 is based on Monomer Q, Monomer R, or a combination of Monomers R and Q. In some embodiments, The CRN in Tables 3 and 4 is based on Monomer R. Each one of sense sequences SEQ ID NOs:161-190 will complex with one of the antisense sequences SEQ ID NOs:191-220, respectively, in other words, SEQ ID NO:161 will complex with SEQ ID NO:191, SEQ ID NO:162 will complex with SEQ ID NO:192, and so forth. "d" refers to "deoxy."

TABLE 3

RNA Targeting PLK1

| SEQ ID NO: | Sense Sequence (5' to 3') |
|---|---|
| 161 | GAGGUCCUAGUGGACCCACGCAcrnGCC |
| 162 | AcrnGGUCCUAGUGGACCCACGCAGCCcrnG |
| 163 | crnCcrnCUAGUGGACCCACGCAGCCGGcrnCGcrnG |
| 164 | GcrnUcrnGGACCCACGCAGCCGGCGGCcrnCcrnU |
| 165 | CUCCUGGAGCUGCACAAGAGGAGcrnGcrnA |
| 166 | CCcrnUGGAGCUGCACAAGAGGAGGAcrnAA |
| 167 | crnGGCUGCCAGUACCUGCACCGAAcrnAcrnCC |
| 168 | GACCUCAAGCUGGGCAACCUUUUcrnCcrnC |
| 169 | GCCUAAAAGAGACCUACCUCCGGAU |
| 170 | ACCUACCUCCGGAUCAAGAAGAAUG |
| 171 | AUACAGUAUUCCCAAGCACAUCAAC |
| 172 | GCCUCCCUCAUCCAGAAGAUGCUUC |
| 173 | AGAAGAUGCUUCAGACAGAUCCCAC |
| 174 | UCUUCUGGGUCAGCAAGUGGGUGGA |
| 175 | CAGCCUGCAGUACAUAGAGCGUGAC |
| 176 | CUGCAGUACAUAGAGCGUGACGGCA |
| 177 | CCcrnUUcrnGAcrnUGcrnAAcrnGAcrnAGcrnAUcrnCAcrnCCcrnCUcrnCCU |
| 178 | UAUcrnUUCcrnCGCcrnAAUcrnUACcrnAUGcrnAGCcrnGAGcrnC |
| 179 | GCCCcrnGGCUcrnGCCCcrnUACCcrnUACGcrnGACCcrnU |
| 180 | GCCAUcrnCAUCCcrnUGCACcrnUCUCAGcrnCAACG |
| 181 | crnCcrnCUUGAUGAAGAAGAUCACdTdT |
| 182 | UUACAGUcrnAcrnUcrnUCCCAAGCACAUU |
| 183 | UACAGUAUcrnUCcrnUCCAAGCACAUUU |
| 184 | UACCUCAAGcrnCcrnUGcrnUGGCAACCUUU |
| 185 | UCCcrnUCAAcrnGCUcrnGGGCAACCUUUU |
| 186 | UAAUACAGUAUUCCCAAGcrnCAcrnUcrnU |
| 187 | UAGcrnAcrnAGAUGCUUCAGACAGAUU |
| 188 | crnUcrnUcrnCCUUGAUGAAGAAGAUCAUU |
| 189 | crnUcrnCCUUGAUGAAGAAGAUCACcrnUcrnU |
| 190 | crnUAUUCCGCAAUUACAUGAGUcrnU |

TABLE 4

RNA Targeting PLK1

| SEQ ID NO: | Antisense Sequence (5' to 3') |
|---|---|
| 191 | GGCUGCGUGGGUCCACUAGGACCUCCG |
| 192 | CGGCUGCGUGGGUCCACUAGGACCUCC |

TABLE 4-continued

RNA Targeting PLK1

| SEQ ID NO: | Antisense Sequence (5' to 3') |
|---|---|
| 193 | CCGCCGGCUGCGUGGGUCCACUAGGAC |
| 194 | AGCGCCGCCGGCUGCGUGGGUCCACUA |
| 195 | UCCUCCUCUUGUGCAGCUCCAGGAGAG |
| 196 | UUUCCUCCUCUUGUGCAGCUCCAGGAG |
| 197 | GGUUUCGGUGCAGGUACUGGCAGCCAA |
| 198 | GGAAAAGGUUGCCCAGCUUGAGGUCUC |
| 199 | AUCCGGAGGUAGGUCUCUUUUAGGcrnCAA |
| 200 | CcrnAUUCUUCUUGAUCCGGAGGUAGGUCcrnU |
| 201 | crnGcrnUUGAUGUGCUUGGGAAUACUGUAcrnUUcrnC |
| 202 | GcrnAcrnAGCAUCUUCUGGAUGAGGGAGGcrnCcrnGcrnG |
| 203 | crnGUGGGAUCUGUCUGAAGCAUCUUCUGG |
| 204 | UCcrnCACCCACUUGCUGACCCAGAAGAcrnUG |
| 205 | crnGUcrnCACGCUCUAUGUACUGCAGGCUcrnGcrnUC |
| 206 | crnUcrnGcrnCCGUCACGCUCUAUGUACUGCAGcrnGcrnC |
| 207 | AGGAGGGUGAUCUUCUUCAUCAAGGAG |
| 208 | GCUCGCUCAUGUAAUUGCGGAAAUAUU |
| 209 | AGGUCCGUAGGUAGGGCAGCCGGGCGA |
| 210 | CGUUGCUGAGGUGCAGGAUGAUGGCGC |
| 211 | GUGAUCUUCUUCAUCAAGGdTdT |
| 212 | UGUGCUUGGGAAUACUGUAUU |
| 213 | AUGUGCUUGGGAAUACUGUUU |
| 214 | AGGUUGCCCAGCUUGAGGUUU |
| 215 | AAGGUUGCCCAGCUUGAGGUU |
| 216 | UGCUUGGGAAUACUGUAUUUU |
| 217 | UCUGUCUGAAGCAUCUUCUUU |
| 218 | UGAUCUUCUUCAUCAAGGAUU |
| 219 | crnGcrnUcrnGAUCUUCUUCAUCAAGGUU |
| 220 | CUCAUGUAAUUGCGGAAAcrnUcrnUcrnU |

Example 3

RNA Targeting AKT1-1

Sequence specific RNAs targeting AKT1-1 are shown in Tables 5 and 6. The CRN in Tables 5 and 6 is based on Monomer R, Monomer Q, or a combination of Monomers R and Q. In some embodiments, the CRN in Tables 5 and 6 is based on Monomer Q. Each one of sense sequences SEQ ID NOs:221-225 will complex with one of the antisense sequences SEQ ID NOs:226-230, respectively, in other words, SEQ ID NO:221 will complex with SEQ ID NO:226, SEQ ID NO:222 will complex with SEQ ID NO:227, and so forth.

TABLE 5

RNA Targeting AKT1-1

| SEQ ID NO: | Sense Sequence (5' to 3') |
|---|---|
| 221 | GUAUUUUGAUGAGGAGUUCACGGcrnCC |
| 222 | GGCCCAGAUGAUCACCAUCACAcrnCA |
| 223 | GGGAAGAAAACUAUCCUGCGGGUcrnUU |
| 224 | GUUUUAAUUUAUUUCAUCCAGUUcrnUcrnG |
| 225 | ACGUAGGGAAAUGUUAAGGACUUcrnCcrnU |

TABLE 6

RNA Targeting AKT1-1

| SEQ ID NO: | Antisense Sequence(5' to 3') |
|---|---|
| 226 | GGCCGUGAACUCCUCAUCAAAAUACCU |
| 227 | UGGUGUGAUGGUGAUCAUCUGGGCCGU |
| 228 | AAACCCGCAGGAUAGUUUUCUUCCCUA |
| 229 | CAAACUGGAUGAAAUAAAUUAAAACCC |
| 230 | AGAAGUCCUUAACAUUUCCCUACGUGA |

Sequence specific sense strands for an mdRNAs targeting AKT1-1 are shown in Tables 7, 8 and 9. The CRN in Tables 7, 8 and 9 is based on Monomer R, Monomer Q, or a combination of Monomers R and Q.

In a nicked mdRNA, each one of sequences SEQ ID NOs:231-235 is attached with a nicked bond to one of the nick sequences SEQ ID NOs:236-240, respectively, in other words, SEQ ID NO:231 is attached to SEQ ID NO:236, SEQ ID NO:232 is attached to SEQ ID NO:237, and so forth, to form a nicked sense strand. The corresponding antisense strand is shown in Table 6.

In a gapped mdRNA, each one of sequences SEQ ID NOs:231-235 is strand S1 while one of the gap sequences SEQ ID NOs:236-240 is strand S2, respectively, in other words, SEQ ID NO:231 is strand S1 and SEQ ID NO:236 is strand S2, SEQ ID NO:232 is strand S1 and SEQ ID NO:237 is strand S2, and so forth. Strands S1 and S2 complex with the corresponding antisense strand of Table 6 to form a gapped structure.

TABLE 7

RNA Targeting AKT1-1

| SEQ ID NO: | Nick position | Sequence (5' to 3') |
|---|---|---|
| 231 | 14 | crnGUAUUUUGAUGAGG |
| 232 | 12 | GGCCCAGAUGAcrnU |
| 233 | 14 | GGGAAGAAAACUAU |
| 234 | 15 | crnGUUUUAAUUUAUUUcrnC |
| 235 | 12 | crnAcrnCGUAGGGAAAU |

TABLE 8

RNA Targeting AKT1-1

| SEQ ID NO: | Nick Sequence 1 (5' to 3') |
|---|---|
| 236 | AGUUCACGGCcrnC |
| 237 | CACCAUCACACCcrnA |
| 238 | CCUGCGGGUcrnUcrnU |
| 239 | AUCCAGUUUG |
| 240 | GUUAAGGACUUcrnCcrnU |

TABLE 9

RNA Targeting AKT1-1

| SEQ ID NO: | Gap Sequence 2 (5' to 3') |
|---|---|
| 241 | GUUCACGGCcrnC |
| 242 | ACCAUCACACCcrnA |
| 243 | CUGCGGGUcrnUcrnU |
| 244 | UCCAGUUUcrnG |
| 245 | UUAAGGACUUCcrnU |

Example 4

RNA Targeting b2a2

Sequence specific RNAs targeting b2a2 are shown in Tables 10 and 11. The CRN in Tables 10 and 11 is based on Monomer R, Monomer Q, or a combination of Monomers R and Q. Each one of sense sequences SEQ ID NOs:246-250 will complex with one of the antisense sequences SEQ ID NOs:251-255, respectively, in other words, SEQ ID NO:246 will complex with SEQ ID NO:251, SEQ ID NO:247 will complex with SEQ ID NO:252, and so forth.

TABLE 10

RNA Targeting b2a2

| SEQ ID NO: | Sense Sequence (5' to 3') |
|---|---|
| 246 | crnGCUGCUUAUGUCUCCCAGCAUGGcrnCcrnC |
| 247 | AAGUGUUUCAGAAGCUUCUCCCUcrnGcrnA |
| 248 | GACCAUCAAUAAGGAAGAAGCCCcrnUcrnU |
| 249 | crnCcrnCAUCAAUAAGGAAGAAGCCCUUCA |
| 250 | crnUcrnCAAUAAGGAAGAAGCCCUUCAGCG |

TABLE 11

RNA Targeting b2a2

| SEQ ID NO: | Antisense Sequence (5' to 3') |
|---|---|
| 251 | GGCCAUGCUGGGAGACAUAAGCAGCAG |
| 252 | UCAGGGAGAAGCUUCUGAAACACUUCU |
| 253 | AAGGGCUUCUUCCUUAUUGAUGGUCAG |
| 254 | UGAAGGGCUUCUUCCUUAUUGAUGGUC |
| 255 | CGCUGAAGGGCUUCUUCCUUAUUGAUG |

Example 5

RNA Targeting b3a2

Sequence specific RNAs targeting b3a2 are shown in Tables 12 and 13. The CRN in Tables 12 and 13 is based on Monomer R, Monomer Q, or a combination of Monomers R and Q. Each one of sense sequences SEQ ID NOs:256-260 will complex with one of the antisense sequences SEQ ID NOs:261-265, respectively, in other words, SEQ ID NO:256 will complex with SEQ ID NO:261, SEQ ID NO:257 will complex with SEQ ID NO:262, and so forth.

TABLE 12

RNA Targeting b3a2

| SEQ ID NO: | Sense Sequence (5' to 3') |
|---|---|
| 256 | ACUGGAUUUAAGCAGAGUUCAAAAcrnG |
| 257 | CUGGAUUUAAGCAGAGUUCAAAAGcrnC |
| 258 | GAUUUAAGCAGAGUUCAAAAGCCCcrnU |
| 259 | AUUUAAGCAGAGUUCAAAAGCCCUcrnU |
| 260 | UUUAAGCAGAGUUCAAAAGCCCUUCcrnA |

TABLE 13

RNA Targeting b3a2

| SEQ ID NO: | Antisense Sequence (5' to 3') |
|---|---|
| 261 | CUUUUGAACUCUGCUUAAAUCCAGUGG |
| 262 | GCUUUUGAACUCUGCUUAAAUCCAGUG |
| 263 | AGGGCUUUUGAACUCUGCUUAAAUCCA |
| 264 | AAGGGCUUUUGAACUCUGCUUAAAUCC |
| 265 | UGAAGGGCUUUUGAACUCUGCUUAAAU |

Example 6

RNA Targeting EGFR-1

Sequence specific RNAs targeting EGFR-1 are shown in Tables 14 and 15. The CRN in Tables 14 and 15 is based on Monomer R, Monomer Q, or a combination of Monomers R and Q. Each one of sense sequences SEQ ID NOs:266-270 will complex with one of the antisense sequences SEQ ID NOs:271-275, respectively, in other words, SEQ ID NO:266 will complex with SEQ ID NO:271, SEQ ID NO:267 will complex with SEQ ID NO:272, and so forth.

TABLE 14

RNA Targeting EGFR-1

| SEQID NO: | Sense Sequence (5' to 3') |
|---|---|
| 266 | UUCCAGCCCACAUUGGAUUCAUcrnCAG |
| 267 | CAGCUGAGAAUGUGGAAUACCUcrnAAG |
| 268 | AACGUAUCUCCUAAUUUGAGGCcrnUCA |
| 269 | CCUAAAAUAAUUUCUCUACAAUcrnUGG |
| 270 | UGGAAGAUUCAGCUAGUUAGGAcrnGCC |

TABLE 15

RNA Targeting EGFR-1

| SEQ ID NO: | Antisense Sequence (5' to 3') |
|---|---|
| 271 | CUGAUGAAUCCAAUGUGGGCUGGAAUC |
| 272 | CUUAGGUAUUCCACAUUCUCAGCUGUG |
| 273 | UGAGCCUCAAAUUAGGAGAUACGUUUU |
| 274 | CCAAUUGUAGAGAAAUUAUUUUAGGAA |
| 275 | GGCUCCUAACUAGCUGAAUCUUCCAAU |

Example 7

RNA Targeting FLT-1

Sequence specific RNAs targeting FLT-1 are shown in Tables 16 and 17. The CRN in Tables 16 and 17 is based on Monomer R, Monomer Q, or a combination of Monomers R and Q. Each one of sense sequences SEQ ID NOs:276-280 will complex with one of the antisense sequences SEQ ID NOs:281-285, respectively, in other words, SEQ ID NO:276 will complex with SEQ ID NO:281, SEQ ID NO:277 will complex with SEQ ID NO:282, and so forth.

TABLE 16

RNA Targeting FLT-1

| SEQ ID NO: | Sense Sequence (5' to 3') |
|---|---|
| 276 | crnUGACCUGUGAAGCAACAGUCAAUGcrnG |
| 277 | crnCUAUCUCACACAUCGACAAACCAcrnAU |
| 278 | crnUGUCCUCAAUUGUACUGCUACCACcrnU |
| 279 | AcrnAACCGUAGCUGGCAAGCGGUCUcrnUA |
| 280 | UAcrnGCUGGCAAGCGGUCUUACCGGcrnCU |

TABLE 17

RNA Targeting FLT-1

| SEQ ID NO: | Antisense Sequence (5' to 3') |
|---|---|
| 281 | CCAUUGACUGUUGCUUCACAGGUCAGA |
| 282 | AUUGGUUUGUCGAUGUGUGAGAUAGUU |
| 283 | AGUGGUAGCAGUACAAUUGAGGACAAG |
| 284 | UAAGACCGCUUGCCAGCUACGGUUUCA |
| 285 | AGCCGGUAAGACCGCUUGCCAGCUACG |

Example 8

RNA Targeting FRAP1

Sequence specific RNAs targeting FRAP1 are shown in Tables 18 and 19. The CRN in Tables 18 and 19 is based on Monomer R, Monomer Q, or a combination of Monomers R and Q. Each one of sense sequences SEQ ID NOs:286-290 will complex with one of the antisense sequences SEQ ID NOs:291-295, respectively, in other words, SEQ ID NO:286 will complex with SEQ ID NO:291, SEQ ID NO:287 will complex with SEQ ID NO:292, and so forth.

TABLE 18

RNA Targeting FRAP1

| SEQ ID NO: | Sense Sequence (5' to 3') |
|---|---|
| 286 | ACUUUGGAUGUUCCAACGCAAGUcrnUcrnG |
| 287 | AAUGCUUCCACUAAACUGAAACCcrnAcrnU |
| 288 | GAGAAAGUUUGACUUUGUUAAAUAcrnU |
| 289 | AAAGAACUACUGUAUAUUAAAAGUcrnU |
| 290 | UUAGAAAUACGGGUUUUGACUUAAcrnC |

TABLE 19

RNA Targeting FRAP1

| SEQ ID NO: | Antisense Sequence (5' to 3') |
|---|---|
| 291 | CAACUUGCGUUGGAACAUCCAAAGUGU |
| 292 | AUGGUUUCAGUUUAGUGGAAGCAUUUA |
| 293 | AUAUUUAACAAAGUCAAACUUUCUCAC |
| 294 | AACUUUUAAUAUACAGUAGUUCUUUUC |
| 295 | GUUAAGUCAAAACCCGUAUUUCUAAAG |

Example 9

RNA Targeting HIF1A-1

Sequence specific RNAs targeting HIF1A-1 are shown in Tables 20 and 21. The CRN in Tables 20 and 21 is based on Monomer R, Monomer Q, or a combination of Monomers R and Q. Each one of sense sequences SEQ ID NOs:296-300 will complex with one of the antisense sequences SEQ ID NOs:301-305, respectively, in other words, SEQ ID NO:296 will complex with SEQ ID NO:301, SEQ ID NO:297 will complex with SEQ ID NO:302, and so forth.

TABLE 20

RNA Targeting HIF1A-1

| SEQ ID NO: | Sense Sequence (5' to 3') |
|---|---|
| 296 | CUAGUCCUUCCGAUGGAAcrnGCACUAG |
| 297 | CCAGUGAAUAUUGUUUUcrnUAUGUGGA |
| 298 | AUGAAUUCAAGUUGGAcrnAUUGGUAGA |
| 299 | CAGGACACAGAUUUAcrnGACUUGGAGA |
| 300 | CUCAAAGCACAGUUcrnACAGUAUUCCA |

TABLE 21

RNA Targeting HIF1A-1

| SEQ ID NO: | Antisense Sequence (5' to 3') |
|---|---|
| 301 | CUAGUGCUUCCAUCGGAAGGACUAGGU |
| 302 | UCCACAUAAAAACAAUAUUCACUGGGA |
| 303 | UCUACCAAUUCCAACUUGAAUUCAUUG |
| 304 | UCUCCAAGUCUAAAUCUGUGUCCUGAG |
| 305 | UGGAAUACUGUAACUGUGCUUUGAGGA |

Example 10

RNA Targeting IL17A

Sequence specific RNAs targeting IL17A are shown in Tables 22 and 23. The CRN in Tables 22 and 23 is based on Monomer R, Monomer Q, or a combination of Monomers R and Q. Each one of sense sequences SEQ ID NOs:306-310 will complex with one of the antisense sequences SEQ ID NOs:311-315, respectively, in other words, SEQ ID NO:306 will complex with SEQ ID NO:311, SEQ ID NO:307 will complex with SEQ ID NO:312, and so forth.

TABLE 22

RNA Targeting IL17A

| SEQ ID NO: | Sense Sequence (5' to 3') |
|---|---|
| 306 | UGAGCUAUUUAAGGAUCUAUUUAUG |
| 307 | AAAAGGUGAAAAAGCACUAUUAUCA |
| 308 | GAAAAAGCACUAUUAUCAGUUCUGC |
| 309 | GGCUGAAAAGAAAGAUUAAACCUAC |
| 310 | UAAACCCUUAUAAUAAAAUCCUUCU |

TABLE 23

RNA Targeting IL17A

| SEQ ID NO: | Antisense Sequence (5' to 3') |
|---|---|
| 311 | CAUAAAUAGAUCCUUAAAUAGCUCAcrnA |
| 312 | UGAUAAUAGUGCUUUUUCACCUUUUUcrnC |
| 313 | GCAGAACUGAUAAUAGUGCUUUUUCAcrnC |
| 314 | GUAGGUUUAAUCUUUCUUUUCAGCCAcrnU |
| 315 | AGAAGGAUUUUAUUAUAAGGGUUUAAcrnU |

Example 11

RNA Targeting IL18

Sequence specific RNAs targeting IL18 are shown in Tables 24 and 25. The CRN in Tables 24 and 25 is based on Monomer R, Monomer Q, or a combination of Monomers R and Q. Each one of sense sequences SEQ ID NOs:316-320 will complex with one of the antisense sequences SEQ ID NOs:321-325, respectively, in other words, SEQ ID NO:316 will complex with SEQ ID NO:321, SEQ ID NO:317 will complex with SEQ ID NO:322, and so forth.

TABLE 24

RNA Targeting IL18

| SEQ ID NO: | Sense Sequence (5' to 3') |
|---|---|
| 316 | CAGGAAUAAAGAUGGCUGCUGAACcrnC |
| 317 | AAUUUGAAUGACCAAGUUCUCUUCcrnA |
| 318 | AUGUAUAAAGAUAGCCAGCCUAGAcrnG |
| 319 | GGCUGUAACUAUCUCUGUGAAGUGcrnU |
| 320 | UCUGUGAAGUGUGAGAAAAUUUCAcrnA |

TABLE 25

RNA Targeting IL18

| SEQ ID NO: | Antisense Sequence (5' to 3') |
|---|---|
| 321 | GGUUCAGCAGCCAUCUUUAUUCCUGCG |
| 322 | UGAAGAGAACUUGGUCAUUCAAAUUUC |
| 323 | CUCUAGGCUGGCUAUCUUUAUACAUAC |
| 324 | ACACUUCACAGAGAUAGUUACAGCCAU |
| 325 | UUGAAAUUUUCUCACACUUCACAGAGA |

Example 12

RNA Targeting IL6

Sequence specific RNAs targeting IL6 are shown in Tables 26 and 27. The CRN in Tables 26 and 27 is based on Monomer R, Monomer Q, or a combination of Monomers R and Q. Each one of sense sequences SEQ ID NOs:326-330 will complex with one of the antisense sequences SEQ ID NOs:331-335, respectively, in other words, SEQ ID NO:326 will complex with SEQ ID NO:331, SEQ ID NO:327 will complex with SEQ ID NO:332, and so forth.

TABLE 26

RNA Targeting IL6

| SEQ ID NO: | Sense Sequence (5' to 3') |
|---|---|
| 326 | ACGAAAGAAGCUCUAUCUcrnCGCCU |
| 327 | CUCCACAAGCGCCUUCGGUCCcrnAGUU |
| 328 | GAGAAGAUUCCAAAGAUGUAGCcrnCGC |
| 329 | AAUCUGGAUUCAAUGAGGAGACUcrnUG |
| 330 | AGAACAGAUUUGAGAGUAGUGAGGcrnA |

TABLE 27

RNA Targeting IL6

| SEQ ID NO: | Antisense Sequence (5' to 3') |
|---|---|
| 331 | AGGCGAGAUAGAGCUUCUCUUUCGUUC |
| 332 | AACUGGACCGAAGGCGCUUGUGGAGAA |
| 333 | GCGGCUACAUCUUUGGAAUCUUCUCCU |
| 334 | CAAGUCUCCUCAUUGAAUCCAGAUUGG |
| 335 | UCCUCACUACUCUCAAAUCUGUUCUGG |

Example 13

RNA Targeting MAP2K1

Sequence specific RNAs targeting MAP2K1 are shown in Tables 28 and 29. The CRN in Tables 28 and 29 is based on Monomer R, Monomer Q, or a combination of Monomers R and Q. Each one of sense sequences SEQ ID NOs:336-340 will complex with one of the antisense sequences SEQ ID NOs:341-345, respectively, in other words, SEQ ID NO:336 will complex with SEQ ID NO:341, SEQ ID NO:337 will complex with SEQ ID NO:342, and so forth.

TABLE 28

RNA Targeting MAP2K1

| SEQ ID NO: | Sense Sequence (5' to 3') |
|---|---|
| 336 | crnCcrnAcrnUcrnGcrnCcrnUcrnGcrnCcrnUcrnGGCGUCUAAGUGUUUG |
| 337 | crnAcrnGcrnAcrnUcrnGUGCAUUUCACCUGUGACAAA |
| 338 | crnUcrnCcrnAAAACCUGUGCCAGGCUGAAUUA |
| 339 | crnGcrnAAUGUGGGUAGUCAUUCUUACAAU |
| 340 | crnAUGUGGGUAGUCAUUCUUACAAUUG |

TABLE 29

RNA Targeting MAP2K1

| SEQ ID NO: | Antisense Sequence (5' to 3') |
|---|---|
| 341 | CAAACACUUAGACGCCAGCAGCAUGGG |
| 342 | UUUGUCACAGGUGAAAUGCACAUCUGA |
| 343 | UAAUUCAGCCUGGCACAGGUUUUGAUC |
| 344 | AUUGUAAGAAUGACUACCCACAUUCAC |
| 345 | CAAUUGUAAGAAUGACUACCCACAUUC |

Example 14

RNA Targeting MAPK1

Sequence specific RNAs targeting MAPK1 are shown in Tables 30 and 31. The CRN in Tables 30 and 31 is based on Monomer R, Monomer Q, or a combination of Monomers R and Q. Each one of sense sequences SEQ ID NOs:346-350 will complex with one of the antisense sequences SEQ ID NOs:351-355, respectively, in other words, SEQ ID NO:346 will complex with SEQ ID NO:351, SEQ ID NO:347 will complex with SEQ ID NO:352, and so forth.

TABLE 30

RNA Targeting MAPK1

| SEQ ID NO: | Sense Sequence (5' to 3') |
|---|---|
| 346 | CAcrnUAcrnUCcrnCUcrnUGcrnGCcrnUAcrnUcrnAAcrnCAcrnUCcrnUGcrnG |
| 347 | UACcrnUAAcrnCAUcrnCUGcrnGAGcrnACUcrnGUGcrnAGCcrnU |
| 348 | CAUAcrnAGUUcrnGUGUcrnGCUUcrnUUUAcrnUUAAcrnU |
| 349 | GCAUCcrnAUUUUcrnGGCUCcrnUUCUUcrnACAUU |
| 350 | GCUCUUcrnCUUACAcrnUUUGUAcrnAAAAUGcrnU |

TABLE 31

RNA Targeting MAPK1

| SEQ ID NO: | Antisense Sequence (5' to 3') |
|---|---|
| 351 | CCAGAUGUUAGUAGCCAAGGAUAUGGU |
| 352 | AGCUCACAGUCUCCAGAUGUUAGUAGC |
| 353 | AUUAAUAAAAAGCACACAACUUAUGGC |
| 354 | AAUGUAAGAAGAGCCAAAAUGAUGCAU |
| 355 | ACAUUUUUACAAAUGUAAGAAGAGCCA |

Example 15

RNA Targeting MAPK14-1

Sequence specific RNAs targeting MAPK14-1 are shown in Tables 32 and 33. The CRN in Tables 32 and 33 is based on Monomer R, Monomer Q, or a combination of Monomers R and Q. Each one of sense sequences SEQ ID NOs:356-360 will complex with one of the antisense sequences SEQ ID NOs:361-365, respectively, in other words, SEQ ID NO:356 will complex with SEQ ID NO:361, SEQ ID NO:357 will complex with SEQ ID NO:362, and so forth.

TABLE 32

RNA Targeting MAPK14-1

| SEQ ID NO: | Sense Sequence (5' to 3') |
|---|---|
| 356 | UCGGAAAcrnCAAGUUAUUCUCUUCACU |
| 357 | ACUCCCAAcrnUAACUAAAUGCUAAGAAA |
| 358 | AAUGCUAAGcrnAAAAUGCUGAAAAUCAA |
| 359 | crnGUCUUUCUCUAAAUAUGAUUACUUU |
| 360 | crnUGAAUUUCAGGCAUUUUGUUCUACA |

TABLE 33

RNA Targeting MAPK14-1

| SEQ ID NO: | Antisense Sequence (5' to 3') |
|---|---|
| 361 | AGUGAAGAGAAUAACUUGUUUCCGAAG |
| 362 | UUUCUUAGCAUUAGUUAUUGGGAGUGA |
| 363 | UUGAUUUUCAGCAUUUCUUAGCAUUAG |
| 364 | AAAGUAAUCAUAUUUAGAGAAAGACAG |
| 365 | UGUAGAACAAAAUGCCUGAAAUUCAGC |

Example 16

RNA Targeting PDGFA

Sequence specific RNAs targeting PDGFA are shown in Tables 34 and 35. The CRN in Tables 34 and 35 is based on Monomer R, Monomer Q, or a combination of Monomers R and Q. Each one of sense sequences SEQ ID NOs:366-370 will complex with one of the antisense sequences SEQ ID NOs:371-375, respectively, in other words, SEQ ID NO:366 will complex with SEQ ID NO:371, SEQ ID NO:367 will complex with SEQ ID NO:372, and so forth.

TABLE 34

RNA Targeting PDGFA

| SEQ ID NO: | Sense Sequence (5' to 3') |
|---|---|
| 366 | AAUGUGACAUCAAAGCAAGUAUUGcrnU |
| 367 | CAUCAAAGCAAGUAUUGUAGCACUcrnC |
| 368 | AGAGAGAGAAAACAAAACCACAAAcrnU |
| 369 | UCGCUGUAGUAUUUAAGCCCAUACcrnA |
| 370 | CGCUGUAGUAUUUAAGCCCAUACAcrnG |

TABLE 35

RNA Targeting PDGFA

| SEQ ID NO: | Antisense Sequence (5' to 3') |
|---|---|
| 371 | ACAAUACUUGCUUUGAUGUCACAUUAA |
| 372 | GAGUGCUACAAUACUUGCUUUGAUGUC |
| 373 | AUUUGUGGUUUUGUUUUCUCUCUCUCU |
| 374 | UGUAUGGGCUUAAAUACUACAGCGAGG |
| 375 | CUGUAUGGGCUUAAAUACUACAGCGAG |

Example 17

RNA Targeting PDGFRA

Sequence specific RNAs targeting PDGFRA are shown in Tables 36 and 37. The CRN in Tables 36 and 37 is based on Monomer R, Monomer Q, or a combination of Monomers R and Q. Each one of sense sequences SEQ ID NOs:376-380 will complex with one of the antisense sequences SEQ ID NOs:381-385, respectively, in other words, SEQ ID NO:376 will complex with SEQ ID NO:381, SEQ ID NO:377 will complex with SEQ ID NO:382, and so forth.

TABLE 36

RNA Targeting PDGFRA

| SEQ ID NO: | Sense Sequence (5' to 3') |
|---|---|
| 376 | crnCcrnUcrnGUUCUGAUCGGCCAGUUUUCGGA |
| 377 | crnAcrnAcrnAUAAUUUGAACUUUGGAACAGGG |
| 378 | crnUGCGACCUUAAUUUAACUUUCCAGU |
| 379 | crnCUGAGAAAGCUAAAGUUUGGUUUUG |
| 380 | crnAGUAAAGAUGCUACUUCCCACUGUA |

TABLE 37

RNA Targeting PDGFRA

| SEQ ID NO: | Antisense Sequence (5' to 3') |
|---|---|
| 381 | UCCGAAAACUGGCCGAUCAGAACAGCC |
| 382 | CCCUGUUCCAAAGUUCAAAUUAUUUGU |
| 383 | ACUGGAAAGUUAAAUUAAGGUCGCAAU |
| 384 | CAAAACCAAACUUUAGCUUUCUCAGCC |
| 385 | UACAGUGGGAAGUAGCAUCUUUACUUU |

Example 18

RNA Targeting PDGFRA

Sequence specific RNAs targeting PDGFRA are shown in Tables 38 and 39. The CRN in Tables 38 and 39 is based on Monomer R, Monomer Q, or a combination of Monomers R and Q. Each one of sense sequences SEQ ID NOs:386-390 will complex with one of the antisense sequences SEQ ID NOs:391-395, respectively, in other words, SEQ ID NO:386 will complex with SEQ ID NO:391, SEQ ID NO:387 will complex with SEQ ID NO:392, and so forth.

TABLE 38

RNA Targeting PDGFRA

| SEQ ID NO: | Sense Sequence (5' to 3') |
|---|---|
| 386 | CUGUUCUGAUCGGCCAGUUUUCcrnGGA |
| 387 | AAAUAAUUUGAACUUUGGAACAGcrnGG |
| 388 | UGCGACCUUAAUUUAACUUUCCAGcrnU |
| 389 | crnCUGAGAAAcrnGCUAAAGUUUGGUUUUcrnG |
| 390 | crnAGUAAAGAUcrnGCUACUUCCCACUGcrnUA |

TABLE 39

RNA Targeting PDGFRA

| SEQ ID NO: | Antisense Sequence (5' to 3') |
|---|---|
| 391 | UCCGAAAACUGGCCGAUCAGAACAGCC |
| 392 | CCCUGUUCCAAAGUUCAAAUUAUUUGU |
| 393 | ACUGGAAAGUUAAAUUAAGGUCGCAAU |
| 394 | CAAAACCAAACUUUAGCUUUCUCAGCC |
| 395 | UACAGUGGGAAGUAGCAUCUUUACUUU |

Example 19

RNA Targeting PIK3CA

Sequence specific RNAs targeting PIK3CA are shown in Tables 40 and 41. The CRN in Tables 40 and 41 is based on Monomer R, Monomer Q, or a combination of Monomers R and Q. Each one of sense sequences SEQ ID NOs:396-400 will complex with one of the antisense sequences SEQ ID NOs:401-405, respectively, in other words, SEQ ID NO:396 will complex with SEQ ID NO:401, SEQ ID NO:397 will complex with SEQ ID NO:402, and so forth.

TABLE 40

RNA Targeting PIK3CA

| SEQ ID NO: | Sense Sequence (5' to 3') |
|---|---|
| 396 | crnGAAUCCUAGUAGAAUGUUUACUACC |
| 397 | GAAAGGGcrnAAGAAUUUUUUGAUGAAA |
| 398 | UAUCGGCAcrnUGCCAGUGUGAAUUU |
| 399 | CACCUCAUcrnAcrnGUAGAGCAAUGUAUGU |
| 400 | CCAGAAUcrnUcrnGcrnCCAAAGCACAUAUAUA |

TABLE 41

RNA Targeting PIK3CA

| SEQ ID NO: | Antisense Sequence (5' to 3') |
|---|---|
| 401 | GGUAGUAAACAUUCUACUAGGAUUCUU |
| 402 | UUUCAUCAAAAAAUUCUUCCCUUUCUG |
| 403 | AAAUUCACACACUGGCAUGCCGAUAGC |
| 404 | ACAUACAUUGCUCUACUAUGAGGUGAA |
| 405 | UAUAUAUGUGCUUUGGCAAUUCUGGUG |

Example 20

RNA Targeting PKN3

Sequence specific RNAs targeting PKN3 are shown in Tables 42 and 43. The CRN in Tables 42 and 43 is based on Monomer R, Monomer Q, or a combination of Monomers R and Q. Each one of sense sequences SEQ ID NOs:406-410 will complex with one of the antisense sequences SEQ ID NOs:411-415, respectively, in other words, SEQ ID NO:406 will complex with SEQ ID NO:411, SEQ ID NO:407 will complex with SEQ ID NO:412, and so forth.

TABLE 42

RNA Targeting PKN3

| SEQ ID NO: | Sense Sequence (5' to 3') |
|---|---|
| 406 | UGCAGUUCUUACACGAGAAGAAGAcrnU |
| 407 | ACGAGAAGAAGAUCAUUUACAGcrnGGA |
| 408 | CGAcrnGAAGAAGAUCAUUUACAGGGAC |
| 409 | AAGAAGAUcrnCAUUUACAGGGACCUGA |
| 410 | AGAGGAAGAGGUGUUUGACUGCAUC |

TABLE 43

RNA Targeting PKN3

| SEQ ID NO: | Antisense Sequence (5' to 3') |
|---|---|
| 411 | AUCUUCUUCUCGUGUAAGAACUGCAGC |
| 412 | UCCCUGUAAAUGAUCUUCUUCUCGUGU |
| 413 | GUCCCUGUAAAUGAUCUUCUUCUCGUG |
| 414 | UCAGGUCCCUGUAAAUGAUCUUCUUCU |
| 415 | GAUGCAGUCAAACACCUCUUCCUCUGU |

Example 21

RNA Targeting RAF1

Sequence specific RNAs targeting RAF1 are shown in Tables 44 and 45. The CRN in Tables 44 and 45 is based on Monomer R, Monomer Q, or a combination of Monomers R and Q. Each one of sense sequences SEQ ID NOs:416-420 will complex with one of the antisense sequences SEQ ID NOs:421-425, respectively, in other words, SEQ ID NO:416 will complex with SEQ ID NO:421, SEQ ID NO:417 will complex with SEQ ID NO:422, and so forth.

TABLE 44

RNA Targeting RAF1

| SEQ ID NO: | Sense Sequence (5' to 3') |
|---|---|
| 416 | UGCAGUAAAcrnGAUCCUAAAGGUUGUC |
| 417 | AGUAAAGAcrnUCCUAAAGGUUGUCGAC |
| 418 | UGACAAAGGAcrnCAACCUGGCAAUUGU |
| 419 | GCAAUUGUGACCCAGUGGUGCGAGcrnG |
| 420 | crnAACAUCAUCCAUAGAGACAUGAAAU |

TABLE 45

RNA Targeting RAF1

| SEQ ID NO: | Antisense Sequence (5' to 3') |
|---|---|
| 421 | GACAACCUUUAGGAUCUUUACUGCAAC |
| 422 | GUCGACAACCUUUAGGAUCUUUACUGC |
| 423 | ACAAUUGCCAGGUUGUCCUUUGUCAUG |
| 424 | CCUCGCACCACUGGGUCACAAUUGCCA |
| 425 | AUUUCAUGUCUCUAUGGAUGAUGUUCU |

Example 22

RNA Targeting SRD5A1

Sequence specific RNAs targeting SRD5A1 are shown in Tables 46 and 47. The CRN in Tables 46 and 47 is based on Monomer R, Monomer Q, or a combination of Monomers R and Q. Each one of sense sequences SEQ ID NOs:426-430 will complex with one of the antisense sequences SEQ ID NOs:431-435, respectively, in other words, SEQ ID NO:426 will complex with SEQ ID NO:431, SEQ ID NO:427 will complex with SEQ ID NO:432, and so forth.

TABLE 46

RNA Targeting SRD5A1

| SEQ ID NO: | Sense Sequence (5' to 3') |
|---|---|
| 426 | AAUGGAGGUUGAAUAUCCUACUGUcrnG |
| 427 | GGAGGUUGAAUAUCCUACUGUGUcrnAA |
| 428 | AUUUUGAGUUUUCCCUUGUAGUcrnGUA |
| 429 | crnUAUCCUGUUUGUUCUUUGUUGAUUG |
| 430 | CcrnCUGUUUGUUCUUUGUUGAUUGAAA |

TABLE 47

RNA Targeting SRD5A1

| SEQ ID NO: | Antisense Sequence (5' to 3') |
|---|---|
| 431 | CACAGUAGGAUAUUCAACCUCCAUUUC |
| 432 | UUACACAGUAGGAUAUUCAACCUCCAU |
| 433 | UACACUACAAGGGAAAACUCAAAAUCU |
| 434 | CAAUCAACAAAGAACAAACAGGAUAAA |
| 435 | UUUCAAUCAACAAAGAACAAACAGGAU |

Example 23

RNA Targeting TNF

Sequence specific RNAs targeting TNF are shown in Tables 48 and 49. The CRN in Tables 48 and 49 is based on Monomer R, Monomer Q, or a combination of Monomers R and Q. Each one of sense sequences SEQ ID NOs:436-440 will complex with one of the antisense sequences SEQ ID NOs:441-445, respectively, in other words, SEQ ID NO:436 will complex with SEQ ID NO:441, SEQ ID NO:437 will complex with SEQ ID NO:442, and so forth.

TABLE 48

| RNA Targeting TNF | |
|---|---|
| SEQ ID NO: | Sense Sequence (5' to 3') |
| 436 | crnAAGAGGGAGAGAAGCAACUACAGAC |
| 437 | CGUCUCCUACCAGACCAAGGUCAcrnAC |
| 438 | GAUCAAUCGcrnGCCCGACUAUCUCGAC |
| 439 | GGACGAACAcrnUCCAACCUUCCCAAAC |
| 440 | AGGGUCGGAcrnACCCAAGCUUAGAACU |

TABLE 49

| RNA Targeting TNF | |
|---|---|
| SEQ ID NO: | Antisense Sequence (5' to 3') |
| 441 | GUCUGUAGUUGCUUCUCUCCCUCUUAG |
| 442 | GUUGACCUUGGUCUGGUAGGAGACGGC |
| 443 | GUCGAGAUAGUCGGGCCGAUUGAUCUC |
| 444 | GUUUGGGAAGGUUGGAUGUUCGUCCUC |
| 445 | AGUUCUAAGCUUGGGUUCCGACCCUAA |

Example 24

RNA Targeting TNFSF13B

Sequence specific RNAs targeting TNFSF13B are shown in Tables 50 and 51. The CRN in Tables 50 and 51 is based on Monomer R, Monomer Q, or a combination of Monomers R and Q. Each one of sense sequences SEQ ID NOs:446-450 will complex with one of the antisense sequences SEQ ID NOs:451-455, respectively, in other words, SEQ ID NO:446 will complex with SEQ ID NO:451, SEQ ID NO:447 will complex with SEQ ID NO:452, and so forth.

TABLE 50

| RNA Targeting TNFSF13B | |
|---|---|
| SEQ ID NO: | Sense Sequence (5' to 3') |
| 446 | AAACACAGAUAACAGGAAAUGAUCC |
| 447 | CUUAAGAAAAGAGAAGAAAUGAAAC |
| 448 | CUGAAGGAGUGUGUUUCCAUCCUCC |
| 449 | UCACCGCGGGACUGAAAAUCUUUGA |
| 450 | AGCAGAAAUAAGCGUGCCGUUCAGG |

TABLE 51

| RNA Targeting TNFSF13B | |
|---|---|
| SEQ ID NO: | Antisense Sequence (5' to 3') |
| 451 | crnGGAUCAUUUCCUGUUAUCUGUGUUUGU |
| 452 | crnGUUUCAUUUCUUCUCUUUUCUUAAGGC |
| 453 | GcrnGAGGAUGGAAACACACUCCUUCAGUU |
| 454 | UcrnCAAAGAUUUUCAGUCCCGCGGUGACA |
| 455 | CCcrnUGAACGGCACGCUUAUUUCUGCUGU |

Example 25

RNA Targeting VEGFA-1

Sequence specific RNAs targeting VEGFA-1 are shown in Tables 52 and 53. The CRN in Tables 52 and 53 is based on Monomer R, Monomer Q, or a combination of Monomers R and Q. Each one of sense sequences SEQ ID NOs:456-460 will complex with one of the antisense sequences SEQ ID NOs:461-465, respectively, in other words, SEQ ID NO:456 will complex with SEQ ID NO:461, SEQ ID NO:457 will complex with SEQ ID NO:462, and so forth.

TABLE 52

| RNA Targeting VEGFA-1 | |
|---|---|
| SEQ ID NO: | Sense Sequence (5' to 3') |
| 456 | CAAAGAAAGAUAGAGCAAGACAAGcrnA |
| 457 | AAGAAAGAUAGAGCAAGACAAGAcrnAA |
| 458 | GAAAGCAUUUGUUUGUACAAGAcrnUCC |
| 459 | UGAGUUAAACGAACGUACUUGCcrnAcrnGA |
| 460 | ACUGAUACAGAACGAUCGAUACcrnAcrnGcrnA |

TABLE 53

| RNA Targeting VEGFA-1 | |
|---|---|
| SEQ ID NO: | Antisense Sequence(5'to 3') |
| 461 | UCUUGUCUUGCUCUAUCUUUCUUUGGU |
| 462 | UUUCUUGUCUUGCUCUAUCUUUCUUUG |
| 463 | GGAUCUUGUACAAACAAAUGCUUUCUC |
| 464 | UCUGCAAGUACGUUCGUUUAACUCAAG |
| 465 | UCUGUAUCGAUCGUUCUGUAUCAGUCU |

Example 26

Increased Melting Temperature of a CRN-Containing Duplex

A CRN-containing RNA duplex targeted to ApoB (SEQ ID NOs:468-469) was prepared and its melting temperature was compared to the same RNA duplex targeted to ApoB that did not contain the CRN (SEQ ID NOs:466-467). The CRN used in this experiment was cmU.

ApoB

```
                           (SEQ ID NO: 466)
Passenger Strand:   5'-CAUCACACUGAAUACCAAUTT (SEQ ID NO: 467)
Guide Strand:       5'-AUUGGUAUUCAGUGUGAUGTT
```

CRN-ApoB

```
                           (SEQ ID NO: 468)
Passenger Strand:   5'-CAUCACACcrnUGAAUACCAAUTT (SEQ ID NO: 469)
Guide Strand:       5'-AUUGGUAUUCAGUGUGAUGTT
```

The CRN-containing RNA duplex targeted to ApoB (SEQ ID NOs:468-469) had a melting temperature of 68.5° C., while the same RNA duplex targeted to ApoB that did not contain the CRN had a melting temperature of 67.1° C. Thus, the use of a single conformationally restricted nucleomonomer crnU increased the melting temperature of the duplex by 1.4° C.

A CRN-containing RNA duplex test sequence (SEQ ID NOs:472-473) was prepared and its melting temperature was compared to the same RNA duplex test sequence that did not contain the CRN (SEQ ID NOs:470-471). The CRN used in this experiment was crnU.

```
Test Sequence
                           (SEQ ID NO: 470)
Passenger Strand:   5'-UUGUUGUUGUUGUUGUUGU (SEQ ID NO: 471)
Guide Strand:       5'-ACAACAACAACAACAACAA CRN-Test Sequence
                           (SEQ ID NO: 472)
Passenger Strand:   5'-UUGUUGUcrnUGUUGUUGUUGU (SEQ ID NO: 473)
Guide Strand:       5'-ACAACAACAACAACAACAA
```

The CRN-containing RNA duplex test sequence had a melting temperature of 63.6° C., while the same RNA duplex test sequence that did not contain the CRN had a melting temperature of 59.8° C. Thus, the use of a single conformationally restricted nucleomonomer crnU increased the melting temperature of the test sequence RNA duplex by 3.8° C.

Example 27

RNA Targeting Factor VII

Sequence specific RNAs targeting Factor VII are shown in Tables 54 and 55. The CRN in Tables 54 and 55 is based on Monomer R, Monomer Q, or a combination of Monomers R and Q. Each one of sense sequences SEQ ID NOs:474-484 will complex with one of the antisense sequences SEQ ID NOs:485-495, respectively, in other words, SEQ ID NO:474 will complex with SEQ ID NO:485, SEQ ID NO:475 will complex with SEQ ID NO:486, and so forth. The designation "unaU" refers to an hydroxymethyl substituted nucleomonomer (unlocked nucleomonomer, UNA) having a U nucleobase. The designation "mU" refers to modified nucleotide "um" which is 2'-O-methyluridine.

TABLE 54

RNA Targeting Factor VII

| SEQ ID NO: | Sense Sequence (5' to 3') |
|---|---|
| 474 | CCAUGUGGAAAAAUACCUAcrnUmU |
| 475 | CUGGAUUUCUUACAGUGAUmUcrnU |
| 476 | AGUGGCUGCAAAAGCUCAUcrnUcrnU |
| 477 | crnGGCAGGUCCUGUUGUUGGUmUmU |
| 478 | CcrnCAGGGUCUCCCAGUACAUmUmU |
| 479 | crnUcrnCGAGUGGCUGCAAAAGCUmUmU |
| 480 | crnGCcrnGGCUGUGAGCAGUACUGmUmU |
| 481 | crnAGGAUGAcrnCCAGCUGAUCUGmUmU |
| 482 | crnCGAUGCUGACUCCAUGUGUmUmU |
| 483 | crnGGCGGUUGUUUAGCUCUCAmUmU |
| 484 | crnUGUCUUGGUUUCAAUUAAAunaUunaU |

TABLE 55

RNA Targeting Factor VII

| SEQ ID NO: | Antisense Sequence (5' to 3') |
|---|---|
| 485 | UAGGUAUUUUUCCACAUGGmUmU |
| 486 | AUCACUGUAAGAAAUCCAGmUmU |
| 487 | AUGAGCUUUUGCAGCCACUmUmU |
| 488 | ACCAACAACAGGACCUGCCmUmU |
| 489 | AUGUACUGGGAGACCCUGGmUmU |
| 490 | AGCUUUUGCAGCCACUCGAmUmU |
| 491 | CAGUACUGCUCACAGCCGCmUmU |
| 492 | CAGAUCAGCUGGUCAUCCUmUmU |
| 493 | ACACAUGGAGUCAGCAUCGmUmU |
| 494 | UGAGAGCUAAACAACCGCCmUmU |
| 495 | UUUAAUUGAAACCAAGACAunaUunaU |

Example 28

RNA Targeting ApoB

Sequence specific RNAs targeting ApoB are shown in Tables 56 and 57. The CRN in Tables 56 and 57 is based on Monomer R, Monomer Q, or a combination of Monomers R and Q. Each one of sense sequences SEQ ID NOs:496-501 will complex with one of the antisense sequences SEQ ID NOs:502-507, respectively, in other words, SEQ ID NO:496 will complex with SEQ ID NO:502, SEQ ID NO:497 will complex with SEQ ID NO:503, and so forth.

TABLE 56

RNA Targeting ApoB

| SEQ ID NO: | Sense Sequence (5' to 3') |
|---|---|
| 496 | GGACAUUCAGAACAAGAAAUcrnU |
| 497 | ACAGAGUCCCUCAAACAGAcrnUU |
| 498 | CAUCACACUGAAUACCAAUcrnUcrnU |
| 499 | AAGGGAAUCUUAUAUUUGAUCCAcrnAcrnA |
| 500 | crnACAGAGUCCCUCAAACAGACAUGAC |
| 501 | GcrnUCUCAAAAGGUUUACUAAUAUUCcrnG |

TABLE 57

RNA Targeting ApoB

| SEQ ID NO: | Antisense Sequence (5' to 3') |
|---|---|
| 502 | UUUCUUGUUCUGAAUGUCCUU |
| 503 | UCUGUUUGAGGGACUCUGUUU |
| 504 | AUUGGUAUUCAGUGUGAUGUU |
| 505 | UUUGGAUCAAAUAUAAGAUUCCCUUCU |
| 506 | GUCAUGUCUGUUUGAGGGACUCUGUGA |
| 507 | CGAAUAUUAGUAAACCUUUUGAGACUG |

Example 29

RNA Targeting TTR

Sequence specific RNAs targeting TTR are shown in Tables 58 and 59. The CRN in Tables 58 and 59 is based on Monomer R, Monomer Q, or a combination of Monomers R and Q. Each one of sense sequences SEQ ID NOs:508-512 will complex with one of the antisense sequences SEQ ID NOs:513-517, respectively, in other words, SEQ ID NO:508 will complex with SEQ ID NO:513, SEQ ID NO:509 will complex with SEQ ID NO:514, and so forth.

TABLE 58

RNA Targeting TTR

| SEQ ID NO: | Sense Sequence (5' to 3') |
|---|---|
| 508 | GUCCUCUGAUGGUCAAAGUUcrnU |
| 509 | GACUGGUAUUUGUGUCUGAUcrnU |
| 510 | UGGACUGGUAUUUGUGUCUUcrnU |
| 511 | CACUCAUUCUUGGCAGGAUUcrnU |
| 512 | CCUUGCUGGACUGGUAUUUUU |

TABLE 59

RNA Targeting TTR

| SEQ ID NO: | Antisense Sequence (5' to 3') |
|---|---|
| 513 | ACUUUGACCAUCAGAGGACUU |
| 514 | UCAGACACAAAUACCAGUCUU |
| 515 | AGACACAAAUACCAGUCCAUU |
| 516 | AUCCUGCCAAGAAUGAGUGUU |
| 517 | AAAUACCAGUCCAGCAAGGUU |

Example 30

RNA Targeting DGAT2

Sequence specific RNAs targeting DGAT2 are shown in Tables 60 and 61. The CRN in Tables 60 and 61 is based on Monomer R, Monomer Q, or a combination of Monomers R and Q. Each one of sense sequences SEQ ID NOs:518-522 will complex with one of the antisense sequences SEQ ID NOs:523-527, respectively, in other words, SEQ ID NO:518 will complex with SEQ ID NO:523, SEQ ID NO:519 will complex with SEQ ID NO:524, and so forth.

TABLE 60

RNA Targeting DGAT2

| SEQ ID NO: | Sense Sequence (5' to 3') |
|---|---|
| 518 | crnUCUCUGUCACCUGGCUCAAUAGGdTdC |
| 519 | CcrnGAGACUACUUUCCCAUCCAGCUdGdG |
| 520 | GAcrnAGACACACAACCUGCUGACCAdCdC |
| 521 | UGAcrnCCACCAGGAACUAUAUCUUUdGdG |
| 522 | GACcrnCACcrnCAGcrnGAACUAUAUCUUUGdGdA |

TABLE 61

RNA Targeting DGAT2

| SEQ ID NO: | Antisense Sequence (5' to 3') |
|---|---|
| 523 | GACCUAUUGAGCCAGGUGACAGAGAAG |
| 524 | CCAGCUGGAUGGGAAAGUAGUCUCGAA |
| 525 | GGUGGUCAGCAGGUUGUGUGUCUUCAC |
| 526 | CCAAAGAUAUAGUUCCUGGUGGUCAGC |
| 527 | UCCAAAGAUAUAGUUCCUGGUGGUCAG |

What is claimed is:

1. An oligomer comprising one or more nucleotide monomers and one or more conformationally restricted Monomers R having the formula

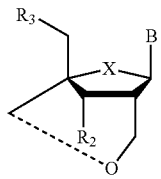

wherein X is independently selected for each occurrence from O, S, $CH_2$, C=O, C=S, C=$CH_2$, CHF and $CF_2$; $R_2$ and $R_3$ are linkages of the monomer to flanking monomers in the oligomer; and
B is a nucleobase or nucleobase analog;
wherein the oligomer has a 5' end and a 3' end, a center position, and a length of from 10 to 40 monomers;
 wherein the oligomer comprises a sequence for PLK1 selected from SEQ ID NOs:161-170;
 wherein the oligomer comprises a Monomer R in one or more of the four positions flanking the center position of the oligomer;
 wherein each nucleobase or nucleobase analog of the oligomer is independently selected from adenine, cytosine, guanine, uracil, hypoxanthine, thymine, 7-deazaadenine, inosine, C-phenyl, C-naphthyl, inosine, an azole carboxamide, nebularine, a nitropyrrole, a nitroindole, 2-aminopurine, 2,6-diaminopurine, hypoxanthine, pseudouridine, 5-methyluridine, 5-propynylcytidine, isocytidine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 2-thioribothymidine, 5,6-dihydrouracil, 4-methylindole, ethenoadenine, deoxyuridine, and deoxy analogs of any of the foregoing.

2. The oligomer of claim 1, wherein the nucleotide monomers are ribonucleotide monomers.

3. The oligomer of claim 1, wherein the nucleotide monomers are deoxyribonucleotide monomers and ribonucleotide monomers.

4. The oligomer of claim 1, wherein the oligomer acts as an antisense, microRNA or antagomir.

5. A duplex oligomer comprising a first strand and a second strand, each strand comprising from 10 to 40 monomers, wherein each strand comprises one or more nucleotide monomers and one or more conformationally restricted Monomers R having the formula

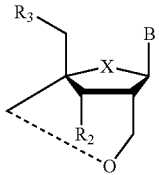

wherein X is independently selected for each occurrence from O, S, $CH_2$, C=O, C=S, C=$CH_2$, CHF and $CF_2$;
$R_2$ and $R_3$ are linkages of the monomer to flanking monomers in the oligomer; and
B is a nucleobase or nucleobase analog;
wherein the oligomer has a 5' end and a 3' end, and a center position;
wherein the duplex oligomer comprises a sequence for PLK1 selected from SEQ ID NOs:161-170;
wherein the duplex oligomer comprises a Monomer R in one or more of the four positions flanking the center position of the duplex oligomer, in either the first strand or the second strand;
wherein each nucleobase or nucleobase analog of the oligomer is independently selected from adenine, cytosine, guanine, uracil, hypoxanthine, thymine, 7-deazaadenine, inosine, C-phenyl, C-naphthyl, inosine, an azole carboxamide, nebularine, a nitropyrrole, a nitroindole, 2-aminopurine, 2,6-diaminopurine, hypoxanthine, pseudouridine, 5-methyluridine, 5-propynyl-cytidine, isocytidine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 2-thioribothymidine, 5,6-dihydrouracil, 4-methylindole, ethenoadenine, deoxyuridine, and deoxy analogs of any of the foregoing; and
wherein the first strand and the second strand form a single double-stranded region of the duplex oligomer.

6. The duplex oligomer of claim 5, wherein the nucleotide monomers are ribonucleotide monomers.

7. The duplex oligomer of claim 5, wherein the nucleotide monomers are deoxyribonucleotide monomers and ribonucleotide monomers.

8. The duplex oligomer of claim 5, wherein the duplex oligomer has a blunt end.

9. The duplex oligomer of claim 5, wherein the duplex oligomer has a 3'-end overhang.

10. A method for decreasing expression of a target mRNA in a cell or an organism comprising administering to the cell or organism the duplex oligomer of claim 5.

* * * * *